US012611173B2

(12) United States Patent
Xu et al.

(10) Patent No.: US 12,611,173 B2
(45) Date of Patent: Apr. 28, 2026

(54) WEARABLE ULTRASOUND IMAGING DEVICE FOR IMAGING THE HEART AND OTHER INTERNAL TISSUE

(71) Applicant: THE REGENTS OF THE UNIVERSITY OF CALIFORNIA, Oakland, CA (US)

(72) Inventors: Sheng Xu, La Jolla, CA (US); Hongjie Hu, La Jolla, CA (US); Hao Huang, La Jolla, CA (US); Mohan Li, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/288,364

(22) PCT Filed: May 10, 2022

(86) PCT No.: PCT/US2022/028541
§ 371 (c)(1),
(2) Date: Oct. 25, 2023

(87) PCT Pub. No.: WO2022/240843
PCT Pub. Date: Nov. 17, 2022

(65) Prior Publication Data
US 2024/0206848 A1 Jun. 27, 2024

Related U.S. Application Data

(60) Provisional application No. 63/186,908, filed on May 11, 2021.

(51) Int. Cl.
*A61B 8/00* (2006.01)
*A61B 8/08* (2006.01)

(52) U.S. Cl.
CPC .......... *A61B 8/4281* (2013.01); *A61B 8/0883* (2013.01); *A61B 8/4236* (2013.01); *A61B 8/4427* (2013.01); *A61B 8/4494* (2013.01); *A61B 8/483* (2013.01); *A61B 8/5207* (2013.01)

(58) Field of Classification Search
CPC ............................. A61B 8/4236; A61B 8/0883
See application file for complete search history.

(56) References Cited

U.S. PATENT DOCUMENTS 6,915,696 B2 * 7/2005 Dufait ................. G01S 15/8925
600/459
2003/0055308 A1 * 3/2003 Friemel ................... A61B 8/14
600/15

(Continued)

FOREIGN PATENT DOCUMENTS

WO 2020/176830 A1 9/2020
WO 2020/215075 A1 10/2020

OTHER PUBLICATIONS

Park et al, "Liquid Metal-Based Soft Electronics for Wearable Healthcare", Advanced Healthcare Materials, vol. 10, pp. 1-20, Mar. 2021 (Year: 2021).*

*Primary Examiner* — Nyrobi Celestine
(74) *Attorney, Agent, or Firm* — Kaplan Breyer Schwarz LLP

(57) ABSTRACT
A stretchable and flexible imaging device that conforms to a shape of patient tissue to which it is attached includes a stretchable and flexible encapsulation substrate and superstrate that is removably attachable to patient tissue. An ultrasound transducer array is disposed between the substrate and superstrate for transmitting and receiving ultrasound waves. The transducer elements are arranged so that data from the received ultrasound waves is processable into an ultrasound image of specified patient tissue. A stretchable and flexible electrical interconnect layered structure is disposed between the superstrate or substrate and the trans-
(Continued)

ducer array and is operatively coupled to the transducer elements such that the electrical interconnect layered structure is configured to address the transducer elements. A controller is configured to implement a beamforming algorithm. The controller is in operative communication with the electrical interconnect layered structure for generating the ultrasound images of the specified patient tissue.

31 Claims, 74 Drawing Sheets

(56) References Cited

U.S. PATENT DOCUMENTS

| | | | |
|---|---|---|---|
| 2004/0168517 A1 | 9/2004 | Dufait | |
| 2005/0283078 A1* | 12/2005 | Steen | A61B 8/463 |
| | | | 600/447 |
| 2011/0319787 A1 | 12/2011 | Lamoise | |
| 2012/0288114 A1 | 11/2012 | Duraiswami | |
| 2016/0038121 A1 | 2/2016 | Waechter-Stehle et al. | |
| 2018/0078970 A1 | 3/2018 | Ono et al. | |
| 2019/0047240 A1 | 2/2019 | Sorin et al. | |
| 2019/0328354 A1* | 10/2019 | Xu | H10N 30/073 |
| 2019/0343484 A1* | 11/2019 | Rothberg | A61B 8/4427 |
| 2019/0366127 A1 | 12/2019 | Emery | |
| 2020/0187916 A1 | 6/2020 | Koptenko et al. | |
| 2021/0015456 A1* | 1/2021 | Chiang | A61B 8/0883 |
| 2021/0236083 A1* | 8/2021 | Lee | A61B 8/5269 |
| 2022/0117503 A1* | 4/2022 | Wang | A61B 5/14521 |
| 2022/0152654 A1* | 5/2022 | Cheyns | B06B 1/0685 |

* cited by examiner

WEARABLE IMAGER

VERTICAL INTERCONNECT ACCESS

TRIBLOCK COPOLYMER SUPERSTRATE

LIQUID METAL SHIELDING LAYER

FOUR-LAYERED LIQUID METAL ELECTRODES 1-3 PIEZOELECTRIC COMPOSITE

BACKING LAYER

LIQUID METAL GROUND ELECTRODE

TRIBLOCK COPOLYMER SUBSTRATE

2$^{nd}$ LAYER

1$^{st}$ LAYER

GROUND ELECTRODE 5 mm

SHIELDING LAYER

4<sup>th</sup> LAYER

3<sup>rd</sup> LAYER

BEFORE STRETCHING

AFTER STRETCHING

PARASTERNAL LONG AXIS VIEW          1 cm

PARASTERNAL SHORT AXIS VIEW          1 cm

APICAL FOUR-CHAMBER VIEW          1 cm

APICAL TWO-CHAMBER VIEW          1 cm

PARASTERNAL LONG & SHORT AXIS VIEWS          1 cm

APICAL FOUR- & TWO-CHANBER VIEWS          1 cm

*FIG. 26D*
*FIG. 26E*
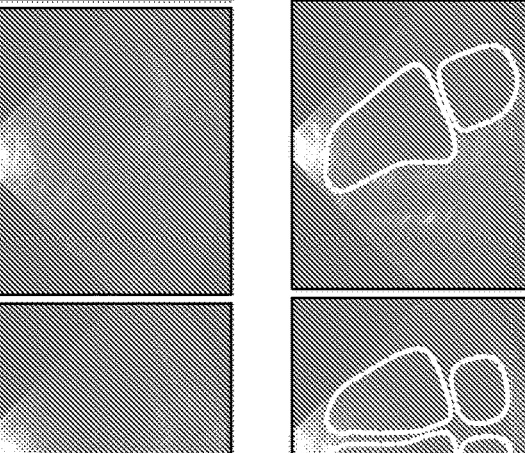

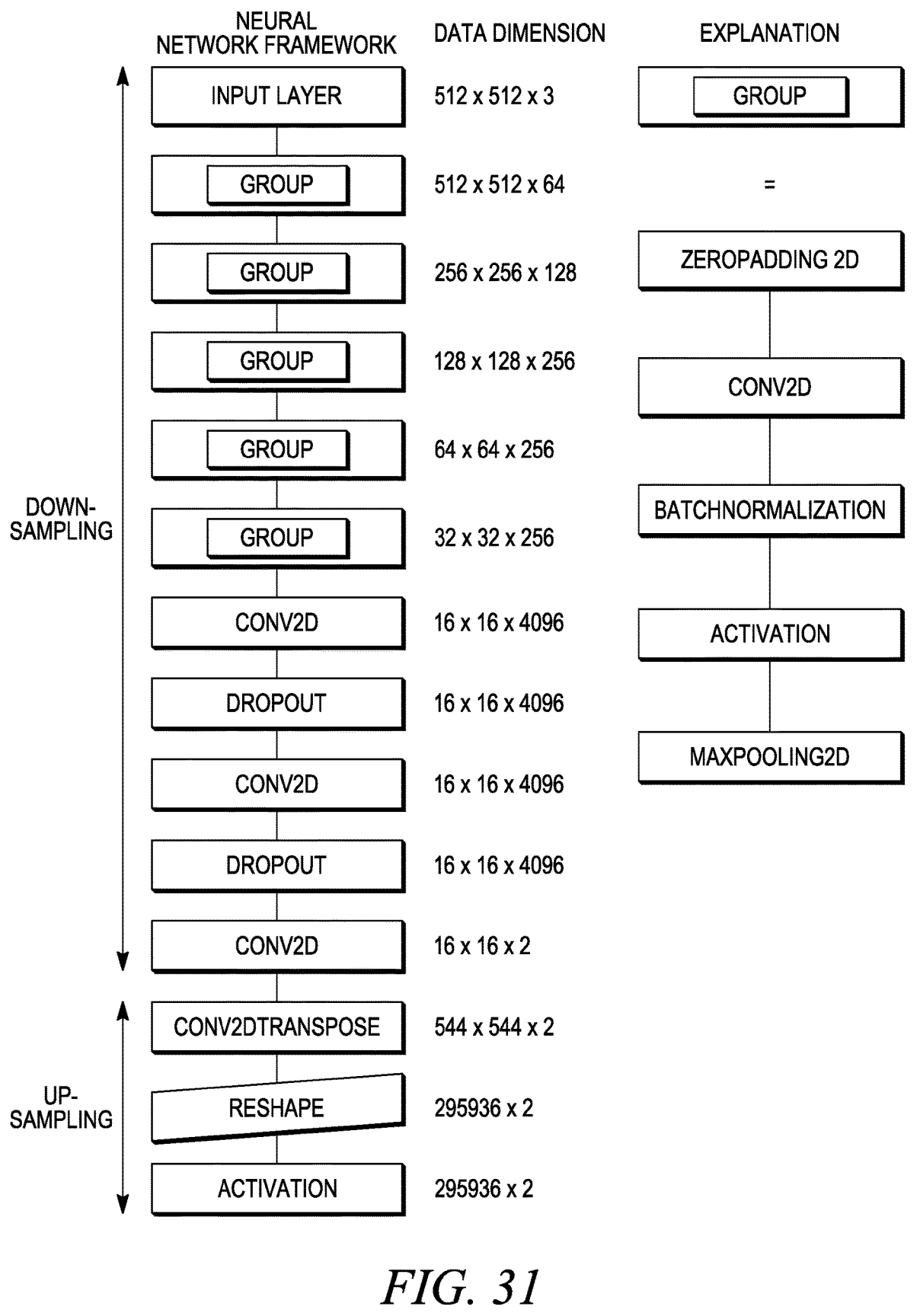

| NEURAL NETWORK FRAMEWORK | DATA DIMENSION | EXPLANATION |
|---|---|---|
| INPUT LAYER | 512 x 512 x 3 | GROUP |
| GROUP | 512 x 512 x 64 | = |
| GROUP | 256 x 256 x 128 | ZEROPADDING 2D |
| GROUP | 128 x 128 x 256 | CONV2D |
| GROUP | 64 x 64 x 256 | BATCHNORMALIZATION |
| GROUP | 32 x 32 x 256 | ACTIVATION |
| CONV2D | 16 x 16 x 4096 | MAXPOOLING2D |
| DROPOUT | 16 x 16 x 4096 | |
| CONV2D | 16 x 16 x 4096 | |
| DROPOUT | 16 x 16 x 4096 | |
| CONV2D | 16 x 16 x 2 | |
| CONV2DTRANSPOSE | 544 x 544 x 2 | |
| RESHAPE | 295936 x 2 | |
| ACTIVATION | 295936 x 2 | |

DOWN-SAMPLING

UP-SAMPLING

*FIG. 31*

STATIC

AFTER EXERCISE

ECN-32

ROTATE TO RIGHT (5 DEGREES)       ROTATE TO LEFT (5 DEGREES)

ADD GAUSSIAN NOISE            RESCALE

MEAN INTERSECTION OVER UNION

ORIGINAL        WITH DATA AUGMENTATION

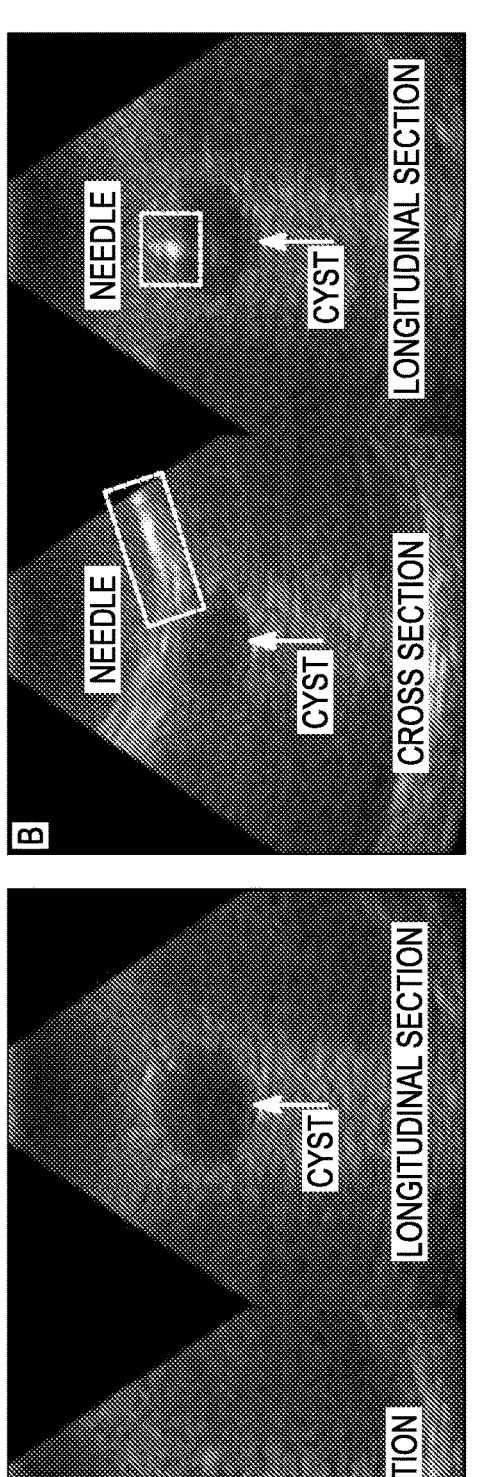
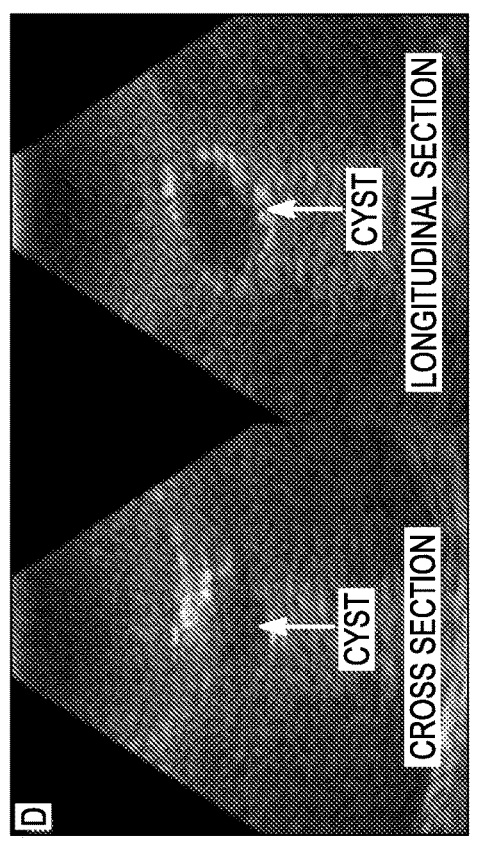
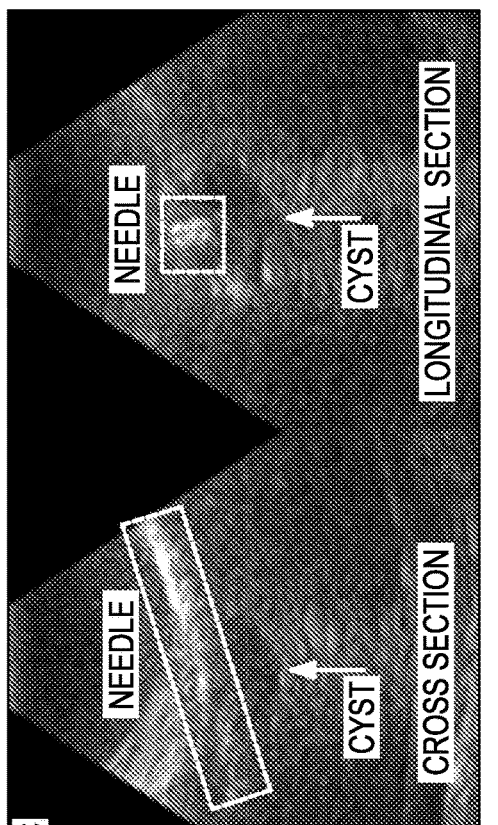
*FIG. 39A*
*FIG. 39B*
*FIG. 39C*
*FIG. 39D*

WEARABLE ULTRASOUND IMAGING DEVICE FOR IMAGING THE HEART AND OTHER INTERNAL TISSUE

CROSS REFERENCE TO RELATED APPLICATION

This application is a 371 National Phase of PCT/US2022/028541, filed May 10, 2022, which claims the benefit of U.S. Provisional Application No. 63/186,908, filed May 11, 2021, the contents of which are incorporated herein by reference.

GOVERNMENT FUNDING

This invention was made with government support under EB025521 and EB027303, awarded by the National Institutes of Health. The government has certain rights in the invention.

BACKGROUND

Normal cardiac function is essential for maintaining systemic perfusion to tissues throughout the body. Cardiovascular diseases, especially in elderlies, impose a huge burden in terms of mortality, morbidity, and disability (Materials and Methods). Because the cardiac function is everchanging, continuous monitoring over a long period is essential for providing reliable and accurate diagnosis. Insufficient sampling would potentially miss critical transient signals (Materials and Methods). Conventional methods for evaluating cardiac functions continuously based on electrocardiogram, ballistocardiogram, seismocardiogram, photoplethysmogram, and electrical impedance tomography only provide limited or indirect information (Materials and Methods). On the other hand, clinical imaging methods, such as magnetic resonance imaging, X-ray computed tomography, positron emission tomography, single photon emission computed tomography, optical voltage map, optical coherence tomography, and ultrasonography, are direct and accurate (Materials and Methods, table S1). However, existing clinical imaging methods are all for short-term use only, because of the cumbersome apparatus setup and the prohibiting cost. Catheter-based ultrasonic transducers can provide short-term continuous cardiac recording, but are invasive and often requires anesthesia that could influence the measurement results.

SUMMARY

In one aspect, a wearable ultrasonic device is provided to perform imaging, including, for example, for high-resolution, real-time, and long-term cardiac imaging. In some embodiments, material fabrication and imaging algorithms are chosen and designed to enable the wearable device to examine the four cardiac chambers in different views. Reliable mechanical coupling between the device and the human skin allows continuous echocardiographic recording during motion. A deep learning model automatically extracts the left ventricular volume from the continuous image recording, yielding waveforms of stroke volume, cardiac output, and ejection fraction simultaneously. These embodiments enable dynamic monitoring of cardiac performance with substantially improved accuracy in various environments.

In some embodiments, a stretchable and flexible imaging device that conforms to a shape of patient tissue to which it is attached includes a stretchable and flexible encapsulation substrate and superstrate. The substrate is removably attachable to patient tissue. An ultrasound transducer array is disposed between the substrate and superstrate for transmitting and receiving ultrasound waves. The transducer elements are arranged so that data from the received ultrasound waves is processable into an ultrasound image of specified patient tissue. A stretchable and flexible electrical interconnect layered structure is disposed between the superstrate or substrate and the transducer array and is operatively coupled to the transducer elements such that the electrical interconnect layered structure is configured to address the transducer elements. A controller is configured to implement a beamforming algorithm. The controller is in operative communication with the electrical interconnect layered structure for generating the ultrasound images of the specified patient tissue.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 26(A)-26(E) show B-mode images collected from a subject with different postures.

FIG. 31 shows the structure of the FCN-32 neural network.

FIGS. 39(A)-39(D) show B-mode images of biopsy tests on a commercial phantom (CIRS 052).

DETAILED DESCRIPTION

Described herein, in one aspect, is a wearable ultrasonic imager that provides continuous and direct cardiac function assessment. New material design in electrode fabrication and encapsulation enables a small form factor and skin-like mechanical properties. Advanced device engineering reduces the array pitch and raises the integration density. A wide-beam ultrasound transmit beamforming strategy for phased array imaging visualizes cardiac anatomic structures in multiple views. A fully convolutional network-32 (FCN-32) can automatically extract the left ventricular volume from the cardiac images, yielding frame-by-frame waveforms of stroke volume, cardiac output, and ejection fraction. This device represents the first example of wearable imaging technology for deep tissues, offering distinct advances for continuous, non-invasive and simultaneous monitoring of multiple cardiac indices.

Design and Characterizations of the Wearable Imager

Figure 1A:
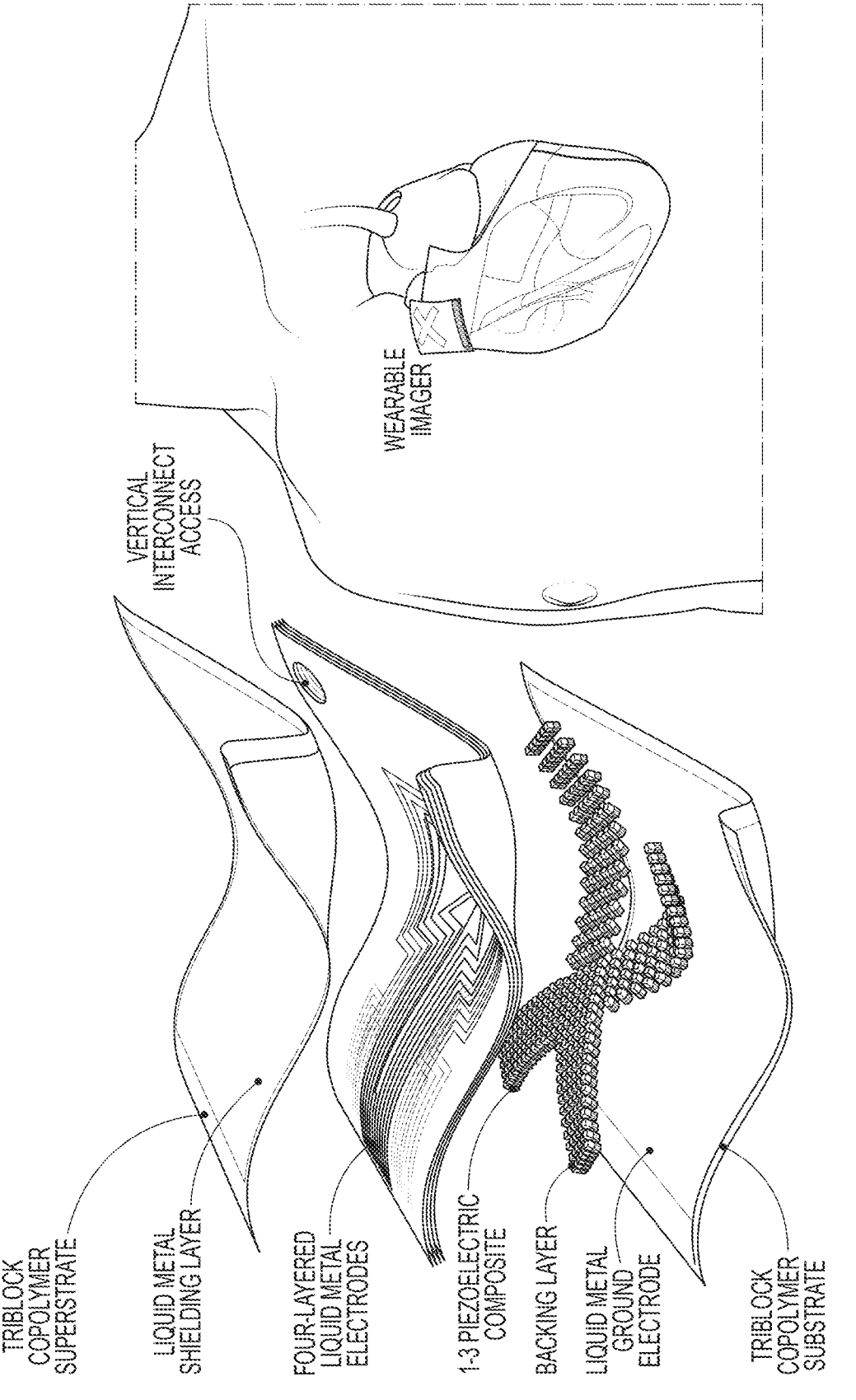
FIGS. 1(A)-1(F) show the design and characterization of the wearable imaging device.

In one particular embodiment, the wearable ultrasonic imager includes piezoelectric transducer arrays, liquid metal composite electrodes, and triblock copolymer encapsulation, as shown by the exploded schematics (see FIG. 1A left, which shows an exploded view of the wearable imager, and see FIG. 6, discussed below). The device is built on styrene-ethylene-butylene-styrene (SEBS). To provide a comprehensive view of the heart, standard clinical practice is to image it in two orthogonal orientations with the rotation of the ultrasound probe. To eliminate the need for a manual rotation, we designed a device with an orthogonal configuration for wearable use (see FIG. 1A right, which shows the device being worn by a subject). Each transducer element consisted of an anisotropic 1-3 piezoelectric composite and a silver-epoxy-based backing layer. To balance the penetration depth and spatial resolution, we chose a center resonant frequency of 3 MHz for deep tissue imaging (see FIG. 9, discussed below). The array pitch was 0.4 mm (i.e., 0.78 ultrasonic wavelength), which enhances lateral resolutions and reduces artifacts caused by grating lobes.

To individually address each element in such a compact array, we made high-density multilayered stretchable electrodes based on a composite of eutectic gallium-indium liquid metal and SEBS. The composite is highly conductive and easy to pattern (see FIG. 1B, which shows the resistance of the liquid metal composite electrode as a function of uniaxial tensile strain. The stretchability of the electrode is around 750%. The insets are the zoomed-in curve of the resistance change before failure and a scanning electron micrograph of the liquid metal composite electrodes with a ~30 μm width. See also FIG. 1C, which shows the cycling performance of the electrode between 0% and 100% uniaxial tensile strain, showing the robustness of the electrode. The inset shows zoomed-in features during cyclic stretching and relaxing of the electrode. See also FIGS. 8-10, discussed below).

Lap shear strength measurements show that the interfacial bonding strength between the transducer element and the SEBS substrate is ~250 kPa, and between the transducer element and the composite electrode ~236 kPa (see FIG. 1D, which shows the lap shear strength of the bonding between transducer elements and SEBS and liquid metal composite electrode.), stronger than typical commercial adhesives. The resulting electrode has a thickness of only ~8 μm (see FIGS. 11 and 12, discussed below). Electromagnetic shielding, also made of the composite, can mitigate the interference of ambient electromagnetic waves, which reduces the noise in the ultrasound radiofrequency signals and enhances image quality (see FIG. 13, discussed below).

The device has excellent electromechanical properties as determined by its high electromechanical coupling coefficient, low dielectric loss, wide bandwidth, and negligible crosstalk (see FIG. 7, discussed below). The entire device has a low Young's modulus of 921 kPa, comparable to the human skin modulus (see FIG. 14, discussed below). The device exhibits a high stretchability with up to ~110% maximum strain (see FIG. 1E, which shows finite element analysis of the entire device under 110% biaxial stretching. The maximum strain is along the long axis of the array; see also FIG. 15, discussed below) and can withstand various deformations (see FIG. 1F, which shows optical images showing mechanical compliance of the wearable imager when bent on a developable surface, wrapped around a non-developable surface, poked, and twisted.). Considering that the typical strain on the human skin is within 20%, these mechanical properties allow the wearable imager to maintain intimate contact with the skin various scenarios.

B-Mode Imaging Strategies and Characterizations

We evaluated the quality of the generated images based on five most crucial metrics for anatomical imaging: spatial resolution (axial, lateral, and elevational), signal-to-noise ratio, location accuracy, dynamic range, and contrast-to-noise-ratio.

Figure 2A:
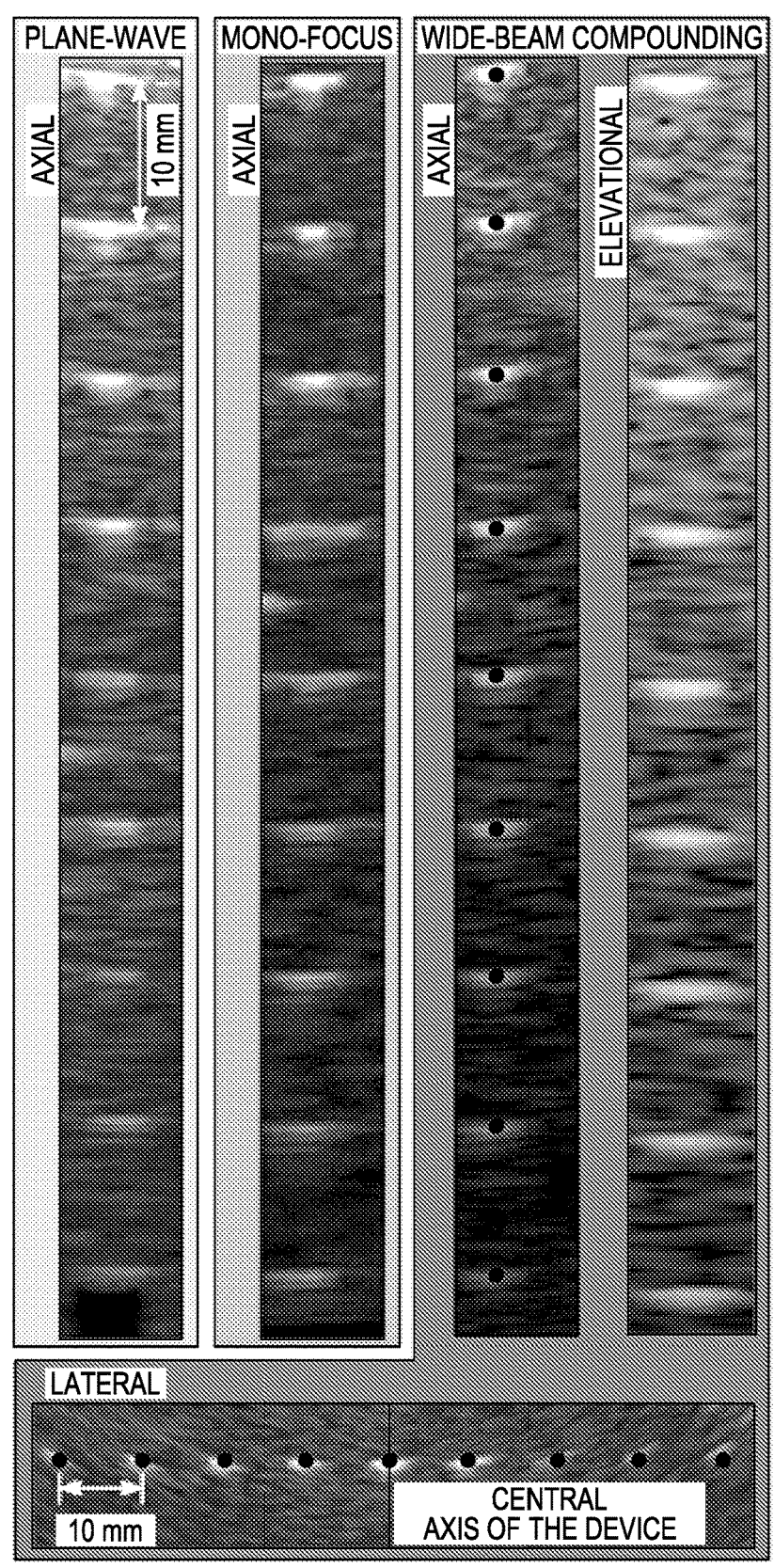
FIGS. 2(A)-2(H) show various B-mode imaging strategies and characterizations thereof.
Figure 2B:
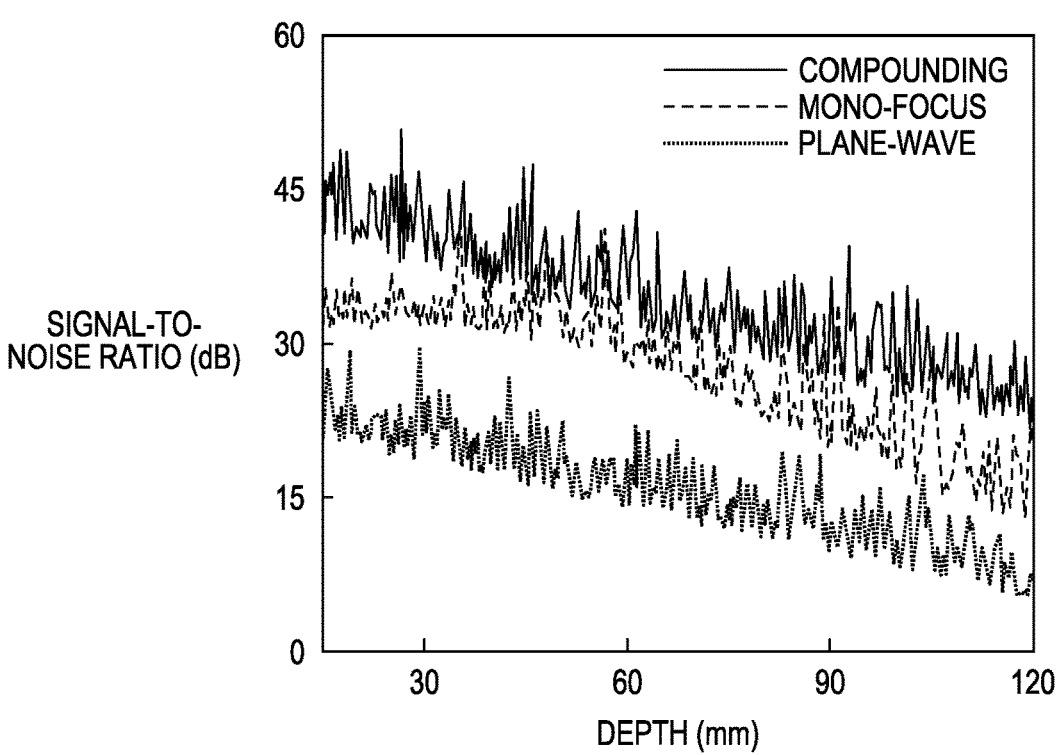
Figure 2C:
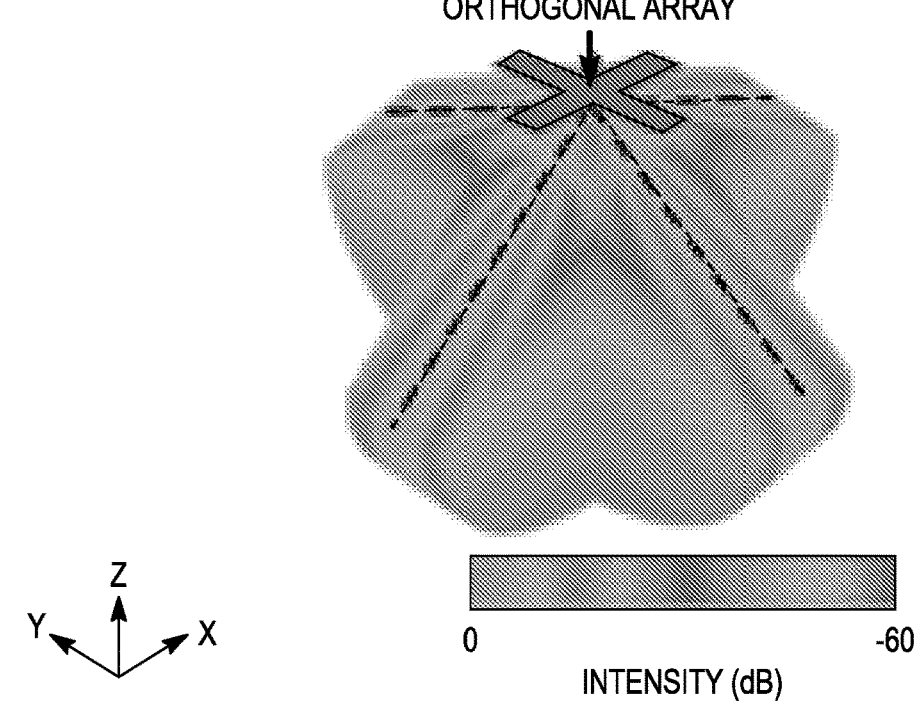

The transmit beamforming strategy is critical for the image quality. Therefore, we first compared three distinct strategies: plane-wave, mono-focus, and wide-beam compounding. Commercial phantoms containing monofilament wires were used for this comparison (see FIG. 16 position 1, discussed below). The plane-wave strategy produces a cross-sectional view with many artifacts along the lateral directions (see FIG. 2A first column, which shows imaging results on wire (100 μm in diameter) phantoms using images through plane-wave beamforming at different depths; see also FIG. 2B, which shows signal-to-noise ratios as a function of the imaging depth under different transmission approaches.). This is because this mode only transmits a single plane wave, resulting in a low echoic signal-to-noise ratio, and poor spatial resolutions (see FIG. 17, discussed below). The mono-focus strategy yields images with fewer artifacts, a greater signal-to-noise ratio, and better spatial resolutions (see FIG. 2A second column, which shows images through plane-wave beamforming at different depths; see also FIG. 17). However, the image quality deteriorates outside the focal zone. The wide-beam compounding strategy implements a sequence of divergent acoustic waves with a series of transmission angles, and the received signals are coherently combined to create a compounding image (see FIG. 17, discussed below). Compared with the conventional plane-wave compounding strategy, the wide-beam compounding in this study expands the sonographic window (see FIG. 18, discussed below). The performance of wide-beam compounding is largely dependent on the step size of the steering angle and the number of steps used (see FIG. 19, discussed below). We used 96 steering angles with a 1° step, which gives adequate penetration depth and spatial resolutions while maintaining an acceptable frame rate of 20-30 Hz. We also used a receive beamforming strategy to further improve the image quality (see FIG. 20, discussed below). The wide-beam compounding method achieves a synthetic focusing effect, and therefore a high acoustic intensity across the entire insonation area (see FIG. 2C, which shows simulated acoustic fields of wide-beam compounding transmit beamforming, with enhanced acoustic field across the entire insonation area.), which leads to the best signal-to-noise ratio and spatial resolutions (see FIG. 2A third column, which shows images through wide-beam compounding at different depths; see also FIG. 2B and FIG. 17, discussed below).

Figure 2D:
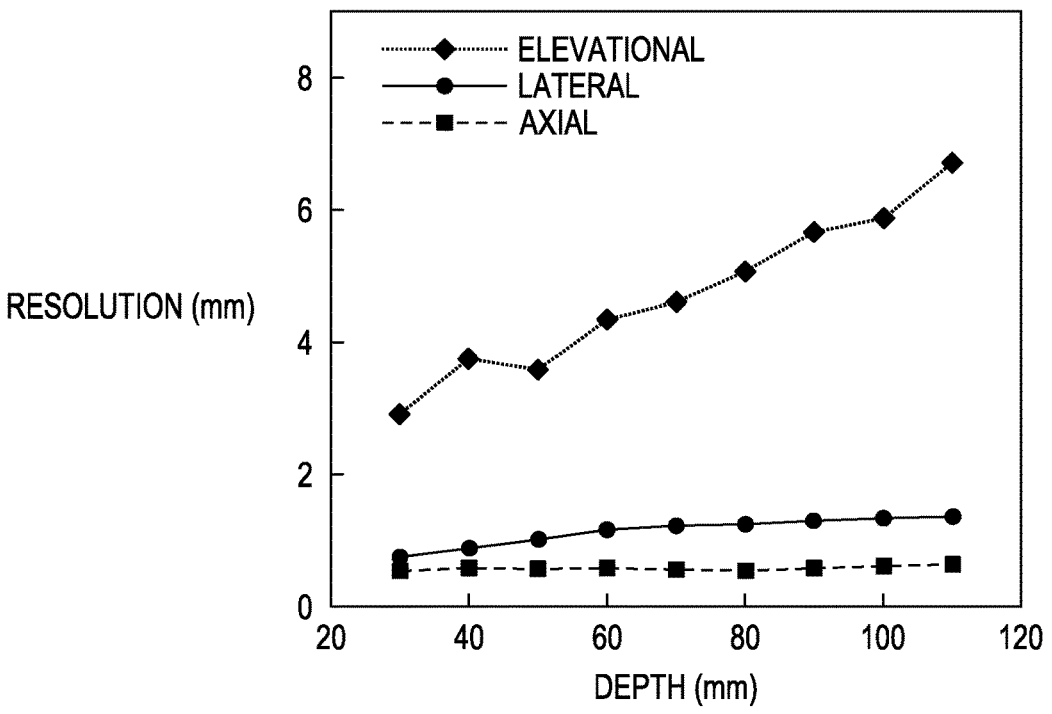
Figure 2E:
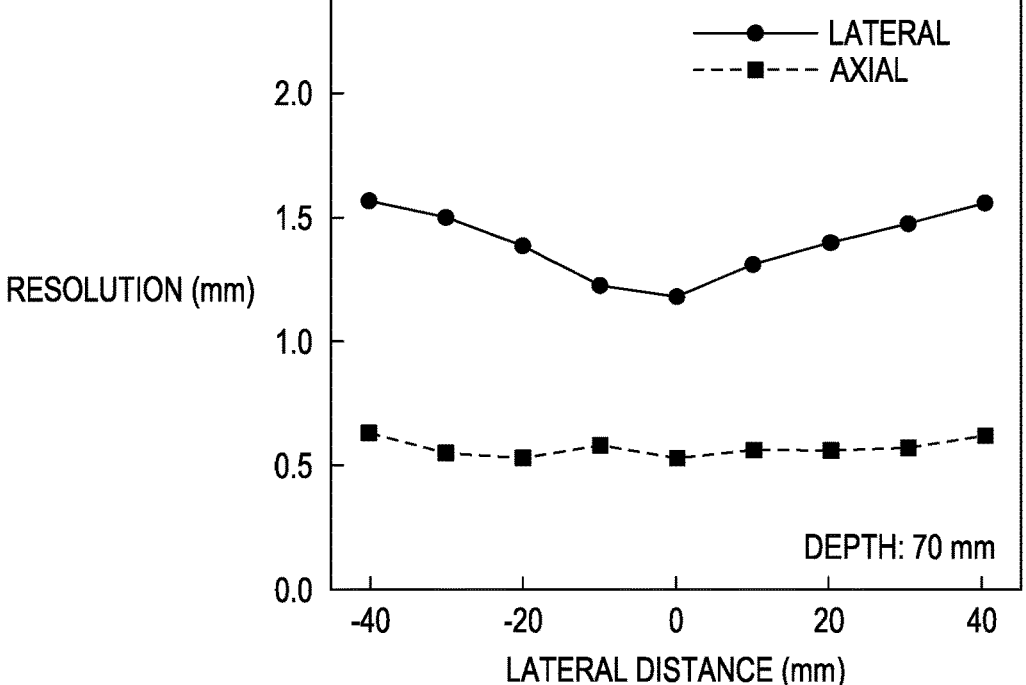

We further characterized the spatial resolution of the device using the wide-beam compounding strategy (see FIG. 16 positions 1 and 2, discussed below). To quantify the resolution, we measured full widths at half maximum from the point spread function curves extracted from the images (see FIG. 2A, third and fourth columns and the bottom row, which shows images of laterally distributed wires, from which the lateral accuracy and spatial resolutions for the wide-beam compounding at different lateral distances from the center can be obtained). As the depth increases, the elevational resolution deteriorates (see FIG. 2D, which shows elevational, lateral, and axial resolutions of the device using wide-beam compounding strategy at different depths), because the beam becomes more divergent in the elevational direction. A longer transducer element offers better acoustic beam convergence in the elevational direction and therefore better elevational resolution. Accordingly, we integrated six small elements into a long element, which improves the device's elevational resolution (see FIG. 6, discussed below). The lateral resolution deteriorates only slightly with depth (see FIG. 2D), due to the process of receive beamforming. The axial resolution remains almost constant with depth (see FIG. 2D), because it depends only on the frequency and bandwidth of the transducer array. Similarly, at the same depth, the axial resolution remains consistent with different lateral distances from the central axis of the device (see FIG. 2E, which shows lateral and axial resolutions of the device using wide-beam compounding strategy with different lateral distances from the center). On the other hand, at the same depth, the lateral resolution is the best at the center, where there is a high overlap of acoustic beams after compounding. Outside the center, the lateral resolution slightly drops.

Another critical metric for imaging is the location accuracy. The agreements between the imaging results and the ground truths (indicated by the dots in FIG. 2A) in the axial and lateral directions are 95.90% and 96.01%, respectively, indicating excellent location accuracy.

Figure 2F:
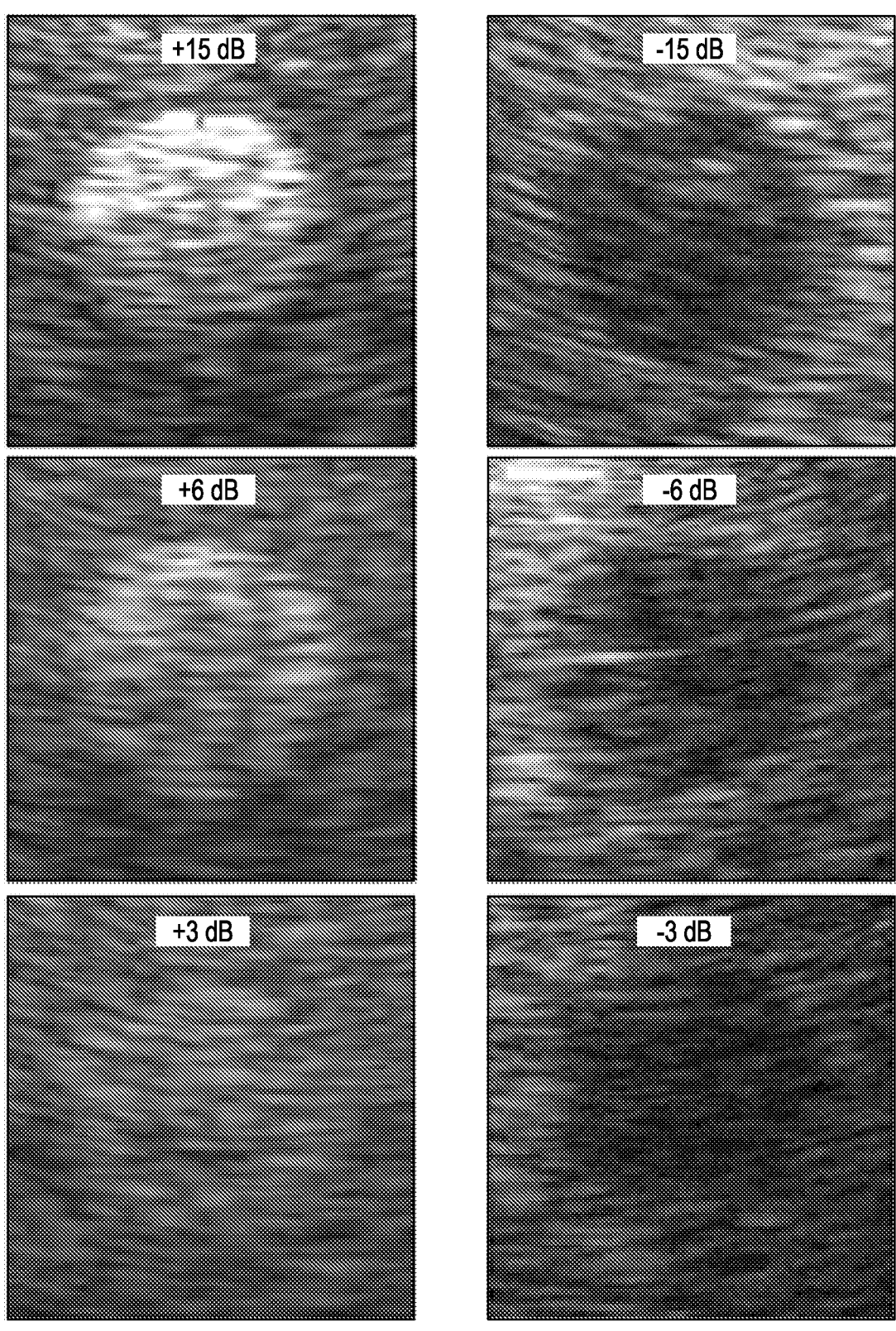
Figure 2G:
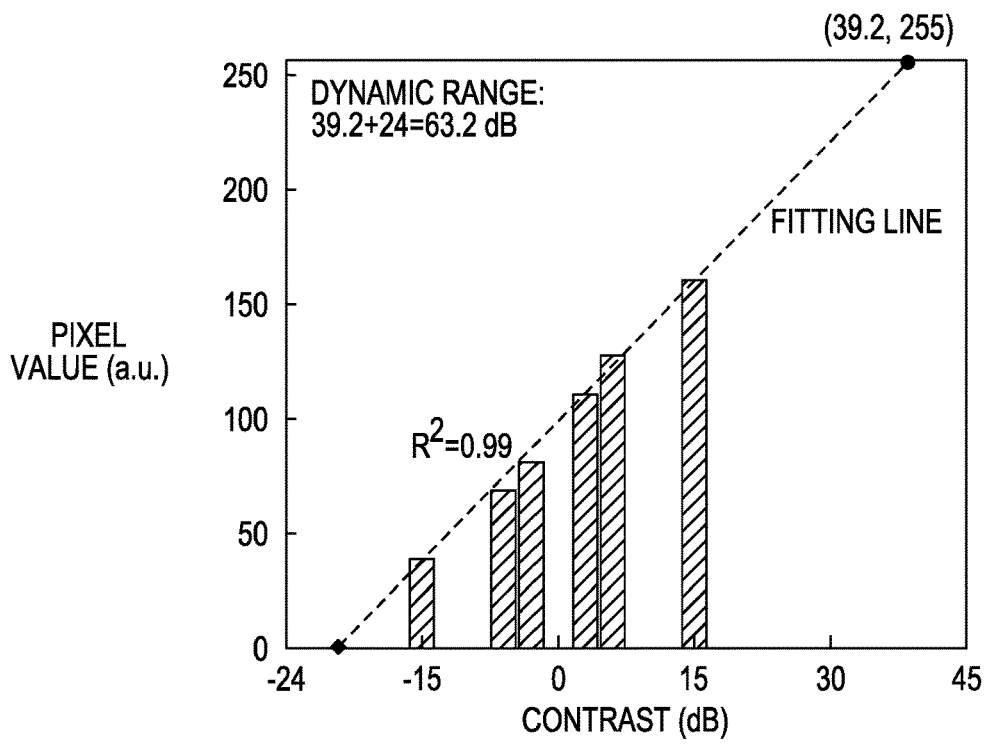

Finally, we evaluated the device's dynamic range and contrast-to-noise ratio using the wide-beam compounding strategy. Phantoms containing cylindrical inclusions with different acoustic impedances were used for the evaluation (see FIG. 16 position 3, discussed below). A high acoustic impedance mismatch results in images with a high contrast, and vice versa (see FIG. 2F, which shows imaging inclusions with different contrasts with respect to the matrix). We extracted the average gray values of the inclusion images and performed a linear regression, and determined the dynamic range to be 63.2 dB (FIG. 2G, which shows the dynamic range of the device; see also FIG. 21, discussed below), which is well above the 60 dB threshold typically used in medical diagnosis.

Figure 2H:
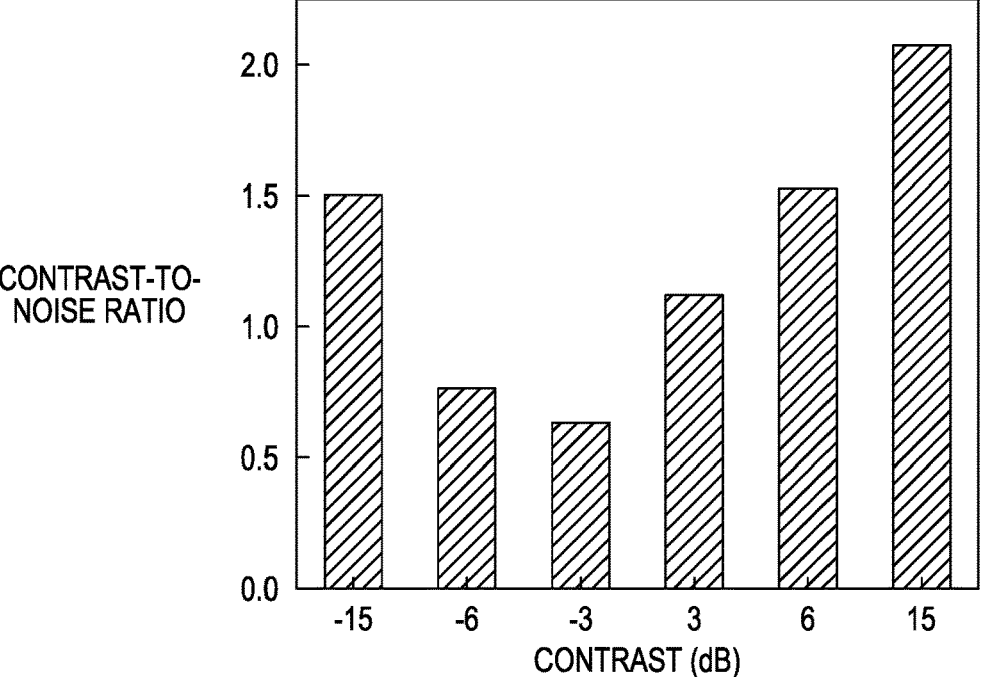

We selected two regions of interest, one inside and the other outside each inclusion area, to derive the contrast-to-noise ratios, which range from 0.63 to 2.07 (see FIG. 2H, which shows the contrast-to-noise ratio of the device). A higher inclusion contrast leads to a higher contrast-to-noise ratio of the image. The inclusions with the lowest contrast (+3 dB or −3 dB) can be clearly visualized, demonstrating the outstanding sensitivity of this device. The performance of the wearable imager is comparable to that of the commercial device (see FIG. 22, discussed below, and table 2).

Echocardiography from Multiple Standard Views

Echocardiography is a commonly used method to examine the structural integrity of the heart. Note that the human chest contours cause a non-planar distribution of the transducer elements, which leads to phase distortion, and therefore image artifacts. We used a three-dimensional scanner to collect the chest curvature to compensate for element position shifts, and thus correct phase distortion during transmit and receive beamforming (see FIGS. 23 and 24, discussed below).

Figure 3A:
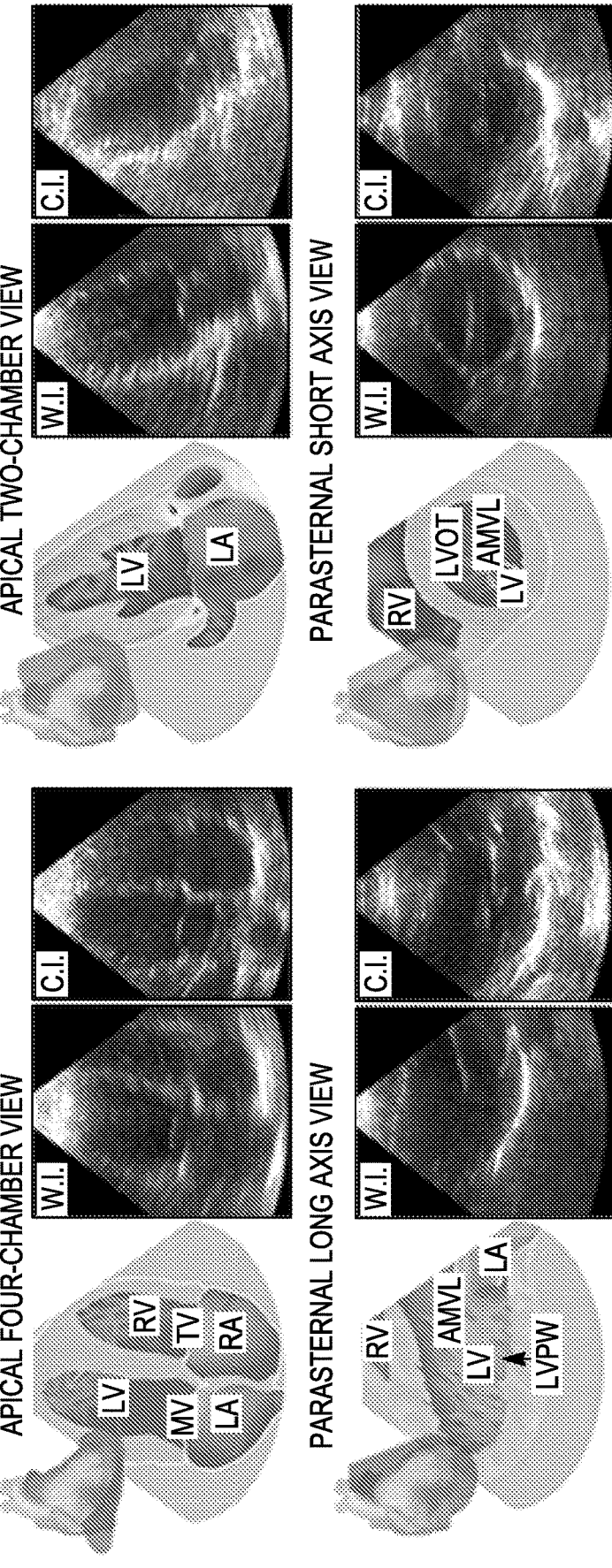
FIGS. 3(A)-3(D) show echocardiography images in various standard views.
Figure 3B:
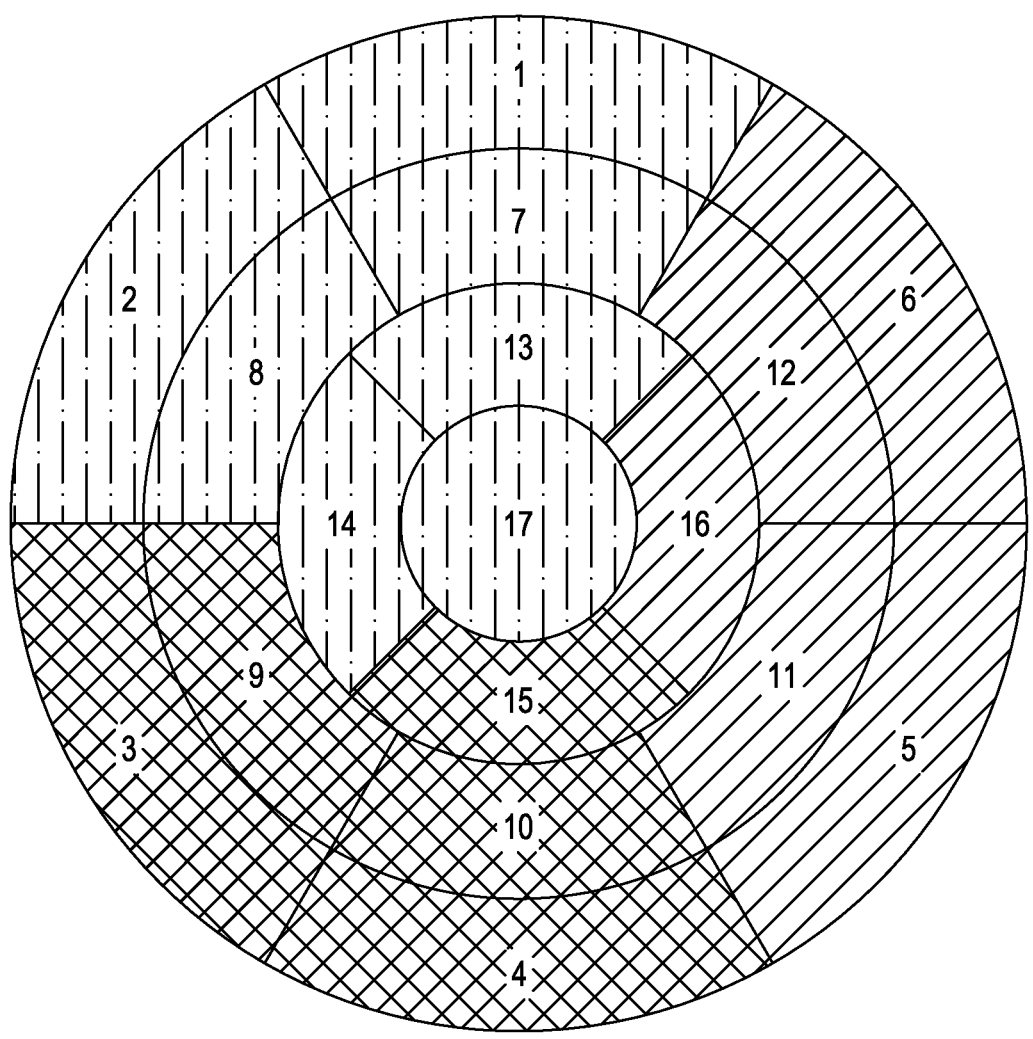
Figure 3C:
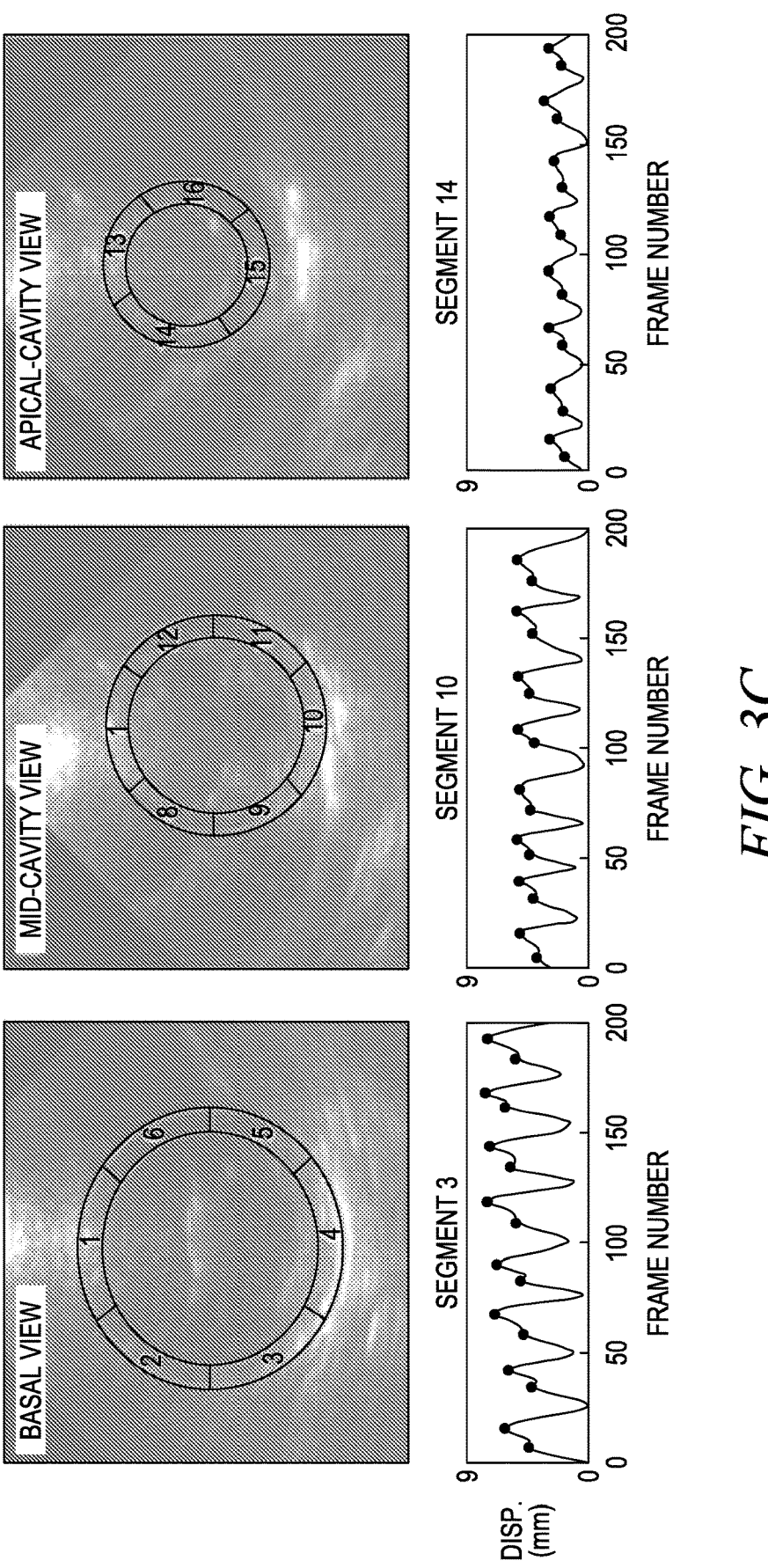

We compared the performance of the device with a commercial device in four primary views of echocardiography, where critical cardiac features can be identified (see FIG. 30, discussed below). FIG. 3A shows the schematics and corresponding B-mode images of these four views including apical four-chamber view, apical two-chamber view, parasternal long axis view, and parasternal short axis view. The difference between the results from the wearable and commercial device is negligible. To identify the specific segment of the left ventricular wall that is potentially pathological, we adopted the 17-segment model (see FIG. 3B, which shows schematics of the 17 segments that together form a full polar plot of the left ventricular wall). We took three different slices of the parasternal short axis view from the left ventricular wall: basal, mid-cavity, and apical-cavity, and recorded the displacement waveform of the myocardium (see FIG. 3C, which shows B-mode images of the left ventricle in basal, mid-cavity, and apical views (top row), and corresponding typical displacement for segments 3, 10, and 14, respectively (bottom row). The peaks are marked with dots.). The two peaks in each cardiac cycle in the displacement curves correspond to the two inflows into the left ventricle during diastole. The wall displacements as measured in the basal, mid-cavity, and apical views become sequentially smaller, consistent with the myocardium radius of the corresponding segments.

Figure 3D:
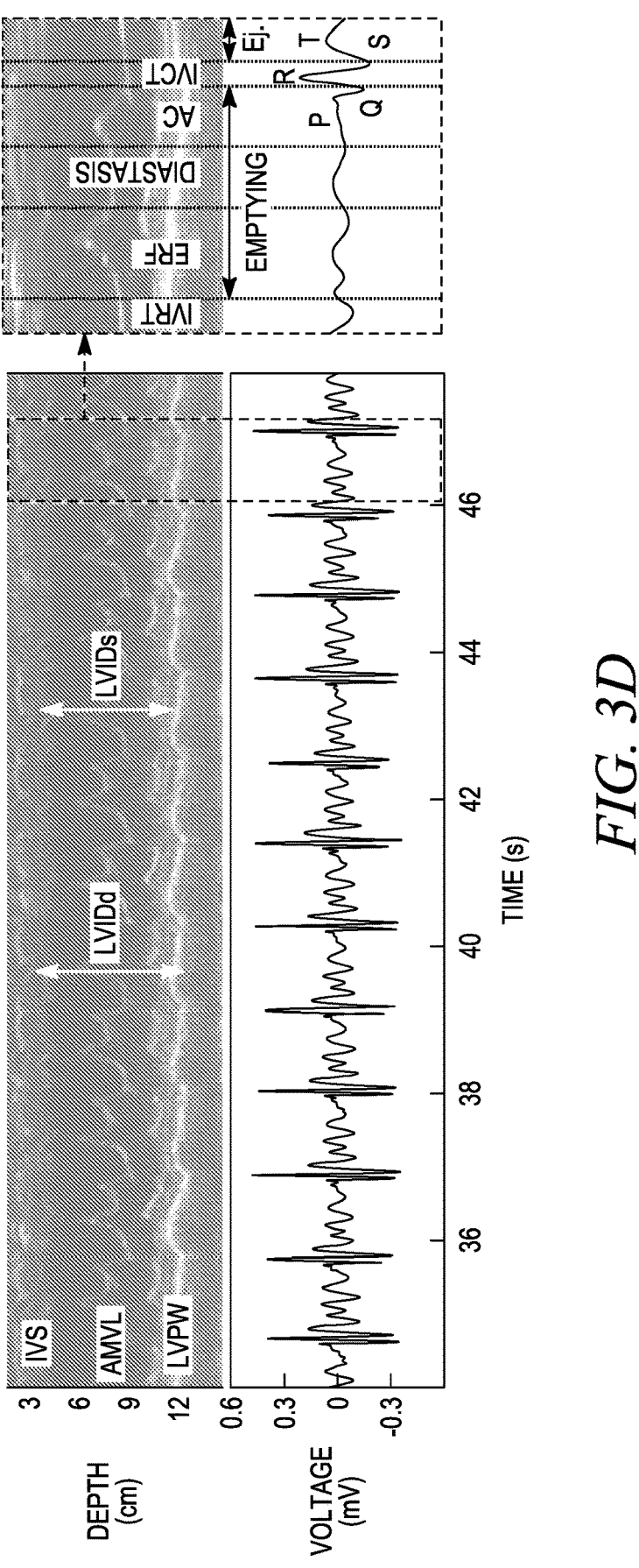

Motion-mode (M-mode) images track activities over time in a target region. We extracted M-mode images from B-mode parasternal long axis view images (see FIG. 3D, which shows M-mode images (upper left) extracted from parasternal long axis view and corresponding electrocardiogram signals (lower left). A zoomed-in plot shows the different phases of a representative cardiac cycle (right). Primary events include diastole and opening of the mitral valve during the P-wave of the electrocardiogram, opening of the aortic valve and systole during the QRS complex, and closure of the aortic valve during the T-wave. The following terminology is used in FIG. 3D: W.I.: wearable imager; C.I.: commercial imager; LV: left ventricle; RV: right ventricle; MV: mitral valve; TV: Tricuspid valve; LA: left atrium; RA: right atrium; LVPW: left ventricular posterior wall; AMVL: anterior mitral valve leaflet; LVOT: left ventricular outflow tract; LVIDd: left ventricular internal diameter end diastole; LVIDs: left ventricular internal diameter end systole; IVS: interventricular septum; IVRT: isovolumetric relaxation time; ERF: early rapid filling; Dias: diastasis; AC: atrial contraction; and IVCT: isovolumetric contraction time; Seg.: Segment.)

Primary targets include the left ventricular chamber, septum, and the mitral/aortic valves. Specifically, the thicknesses of the chamber walls and septum can be tracked. Valvular functions, e.g., their opening and closing velocities, can be evaluated based on the distance between the leaflet and septal wall. Moreover, we can correlate the mechanical activities in the M-mode images with the electrical activities in electrocardiogram measured simultaneously during different phases in a cardiac cycle (see FIG. 3D).
Monitoring During Motion Stress echocardiography assesses cardiac response to stress induced by exercise or pharmacologic agents, which may include new or worsened ischemia presenting as wall motion abnormalities, and is crucial in the diagnosis of coronary diseases. However, in current procedures, ultrasound images are obtained only before and after exercise. With the cumbersome apparatus, it is impossible to acquire data during exercise, which may contain invaluable real-time insights when new abnormalities initiates. Because images are traditionally obtained immediately after exercise, a quick recovery can mask the transient pathologic response during stress and lead to false negative examinations. In addition, the endpoint of the exercise is subjective, which may result in suboptimal testing.

The wearable imager is ideal for overcoming these challenges. The device can be attached to the chest wall with minimal constraint to the subjects' movement, providing continuous recording of cardiac activities before, during, and after exercise with negligible motion artifacts (see FIG. 26, discussed below). This not only captures the real-time response during the test, but also offers objective data to standardize the end-point and enhances patient safety throughout the test.

On human subjects, instead of water-based ultrasound gels that evaporate over time, we used silicone as the couplant, which produces images of similar quality (see FIG. 27, discussed below). The device did not induce any skin irritation or allergy after 24 h continuous wear (see FIG. 28, discussed below). The device temperature stayed at ~33° C., and the subject with reproducible results heart rate remained stable after the device continuously worked for 1 h (see FIG. 29, discussed below), indicating minimal influence of the device on the cardiac function. The device can be reused on different subjects (see FIG. 30, discussed below).

Figure 4A:
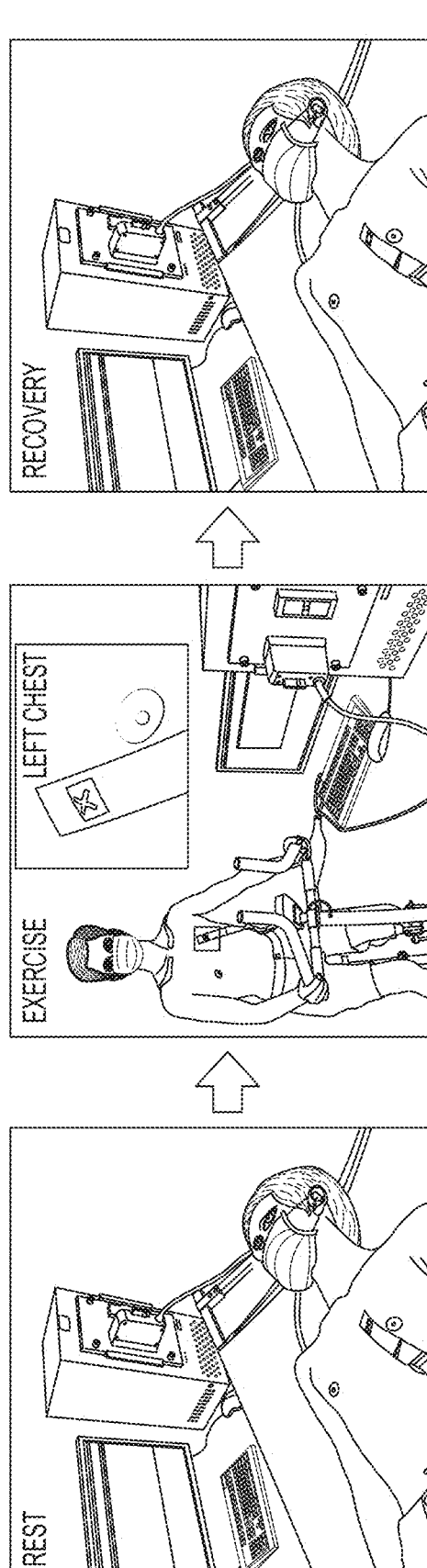
FIGS. 4(A)-4(F) schematically illustrate the stages of a stress echocardiography process and show the results of monitoring the subject during motion using the wearable imaging device described herein.

We performed stress echocardiography to demonstrate the device performance. The experiment is conducted with the device attached to the subject for continuous recording along the parasternal long axis during the entire process, which consisted of three main stages (see FIG. 4A, which shows three stages of stress echocardiography. In the rest stage, the subject lies supine for ~4 mins. In the exercise stage, the subject rides a stationary bike for ~15 mins with intervals for rest. In the recovery stage, the subject lies supine again for ~10 mins. The wearable imager is attached to the subject's chest throughout the entire test.).

In the rest stage, the subject laid in the supine position. In the exercise stage, the subject exercised on a stationary bike with several intervals until a possible maximal heart rate was reached. In the recovery stage, the subject was placed in the supine position again to recover. The results demonstrated uninterrupted tracking of the left ventricular activities, including the corresponding M-mode echocardiography and synchronized heart rate waveform (see FIGS. 4B, which shows continuous M-mode echocardiography extracted from the parasternal long axis view B-mode images of the entire process. Key features of the interventricular septum and left ventricular posterior wall are identified. The stages of rest, exercise, with intervals of rest, and recovery are labelled; and see also FIG. 4C, which shows variations in the heart rate extracted from the M-mode echocardiography).

Figure 4B:
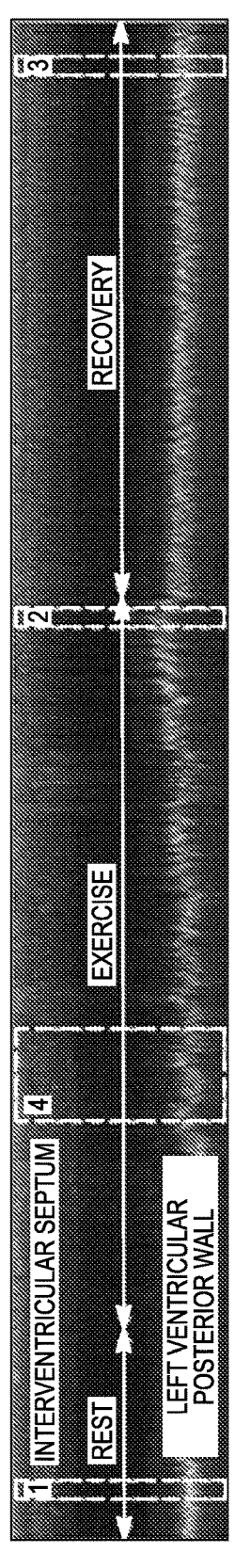
Figure 4C:
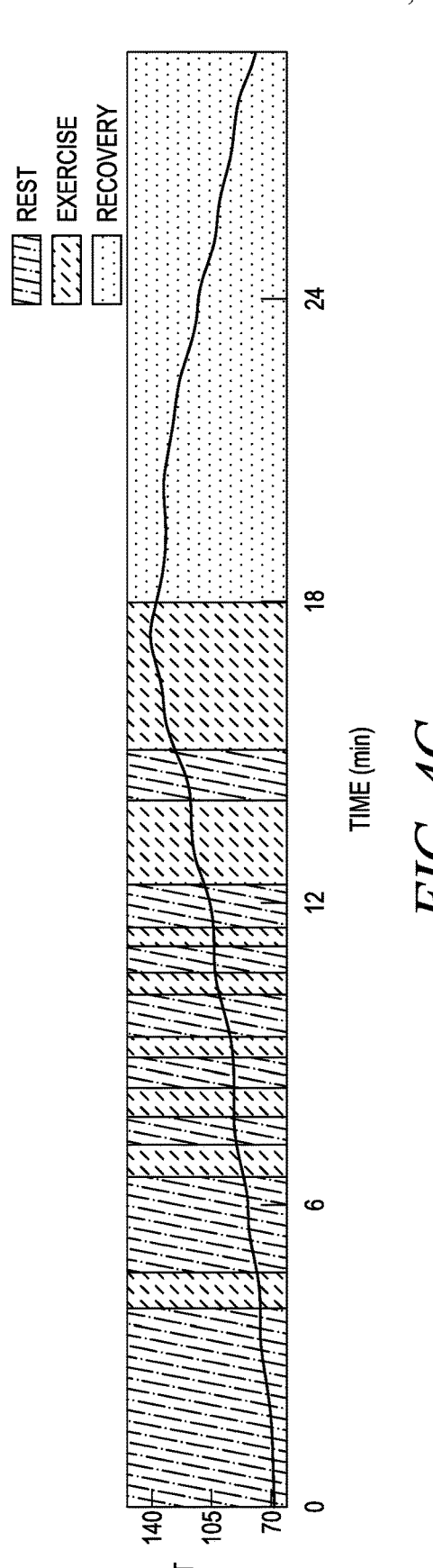
Figures 4D, 4E:
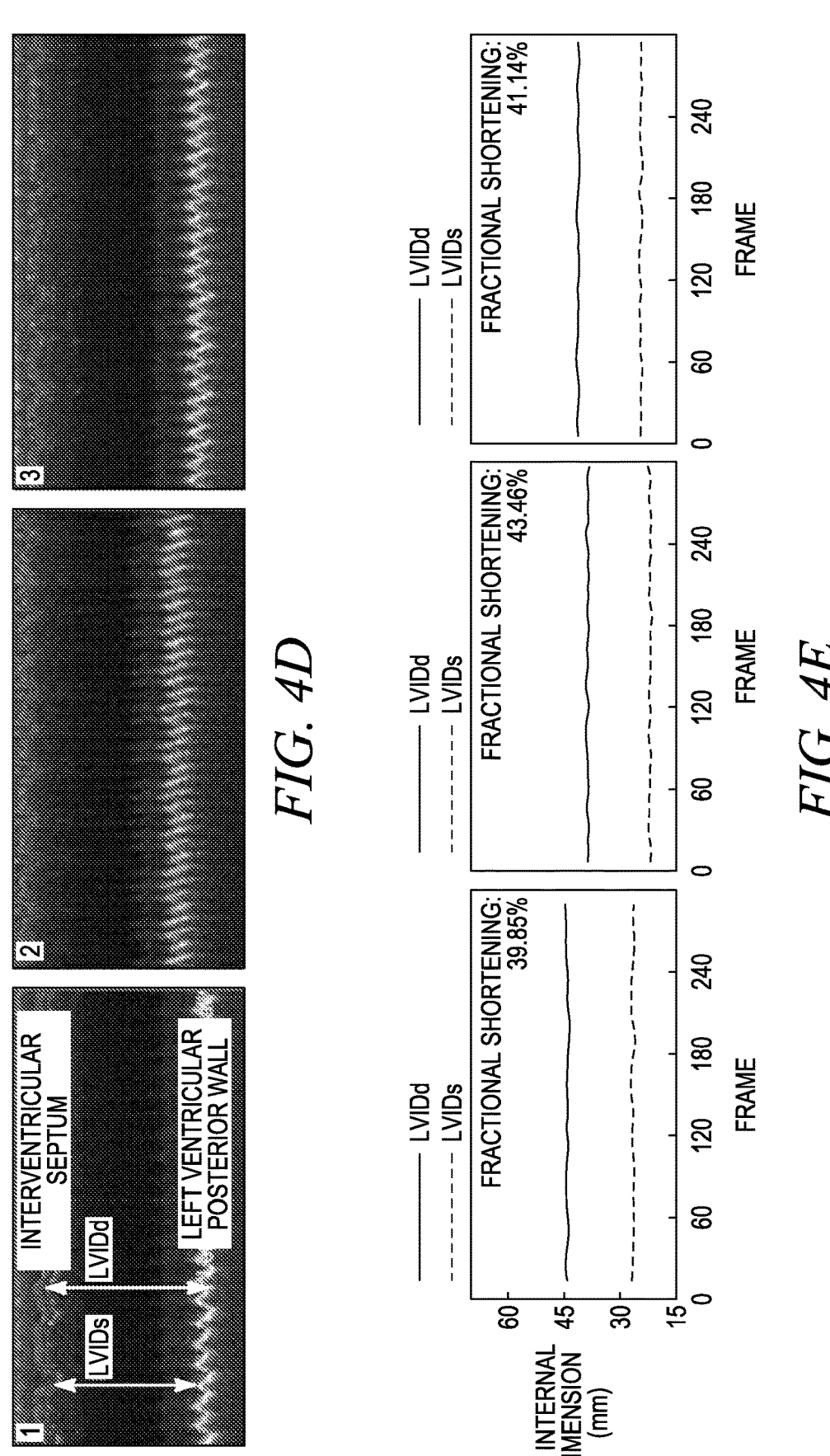
Figure 4F:
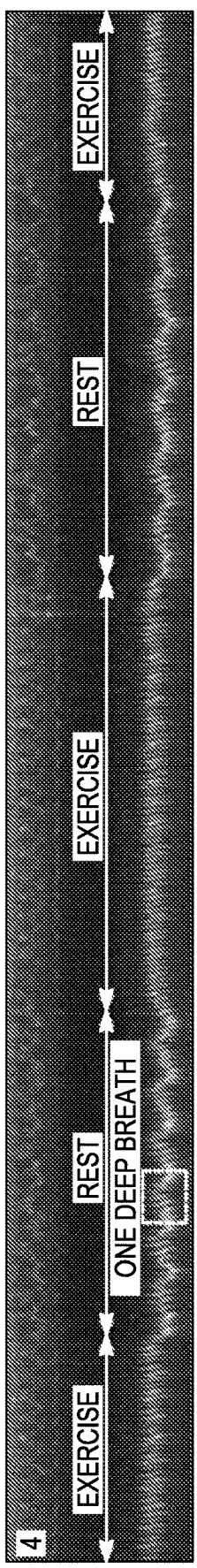

We examined a representative section of each test stage, and extracted the left ventricular internal diameter end systole (LVIDs) and left ventricular internal diameter end diastole (LVIDd) (see FIG. 4D, which shows zoomed-in images of sections #1 (rest), #2 (exercise), and #3 (recovery) (dashed boxes) in FIG. 4(B). LVIDd and LVIDs are labelled in the first section). The subject's LVIDs and LVIDd remained stable during the rest stage (see FIG. 4E, which shows LVIDd and LVIDs waveforms of the three different sections of the recording and corresponding average fractional shortening). In the exercise stage, the subject's interventricular septum and the left ventricular posterior wall moved closer to the skin surface, with the latter moving more than the former, resulting in a decrease in LVIDs and LVIDd. In the recovery stage, the LVIDs and LVIDd slowly returned to normal. The variation in fractional shortening, is a measure of the cardiac muscular contractility, reflects the changing demand for blood supply in different stages of stress echocardiography (see FIG. 4E). Particularly, section 4 in FIG. 4B includes periods of exercise and intervals for rest (see FIG. 4F, which shows zoomed-in images of section #4 (dashed box) during exercise with intervals of rest in FIG. 4(B). Periodic variations in M-mode signals of the left ventricular posterior wall indicate breathing pattern of the subject). In the first interval, the subject took rhythmic deep breath for six times, with each accompanied by 7-8 heart-beats. Whereas during exercise, there seem to be no obvious signs of deep breath, probably because the subject switched from diaphragmatic to thoracic breathing, which is shal-lower and usually takes less time.

Automatic Image Processing

Cardiovascular diseases are often associated with changes in the pumping capabilities of the heart, as measured by stroke volume, cardiac output, and ejection fraction. Therefore, non-invasive, continuous monitoring of these indices are attractive for the diagnosis and surveillance of cardiovascular conditions. Critical information embodied in these waveforms may help precisely determine potential risk factors. On the other hand, processing of the unprecedented image data streams, if done manually, can be overwhelming for clinicians.

Figure 5A:
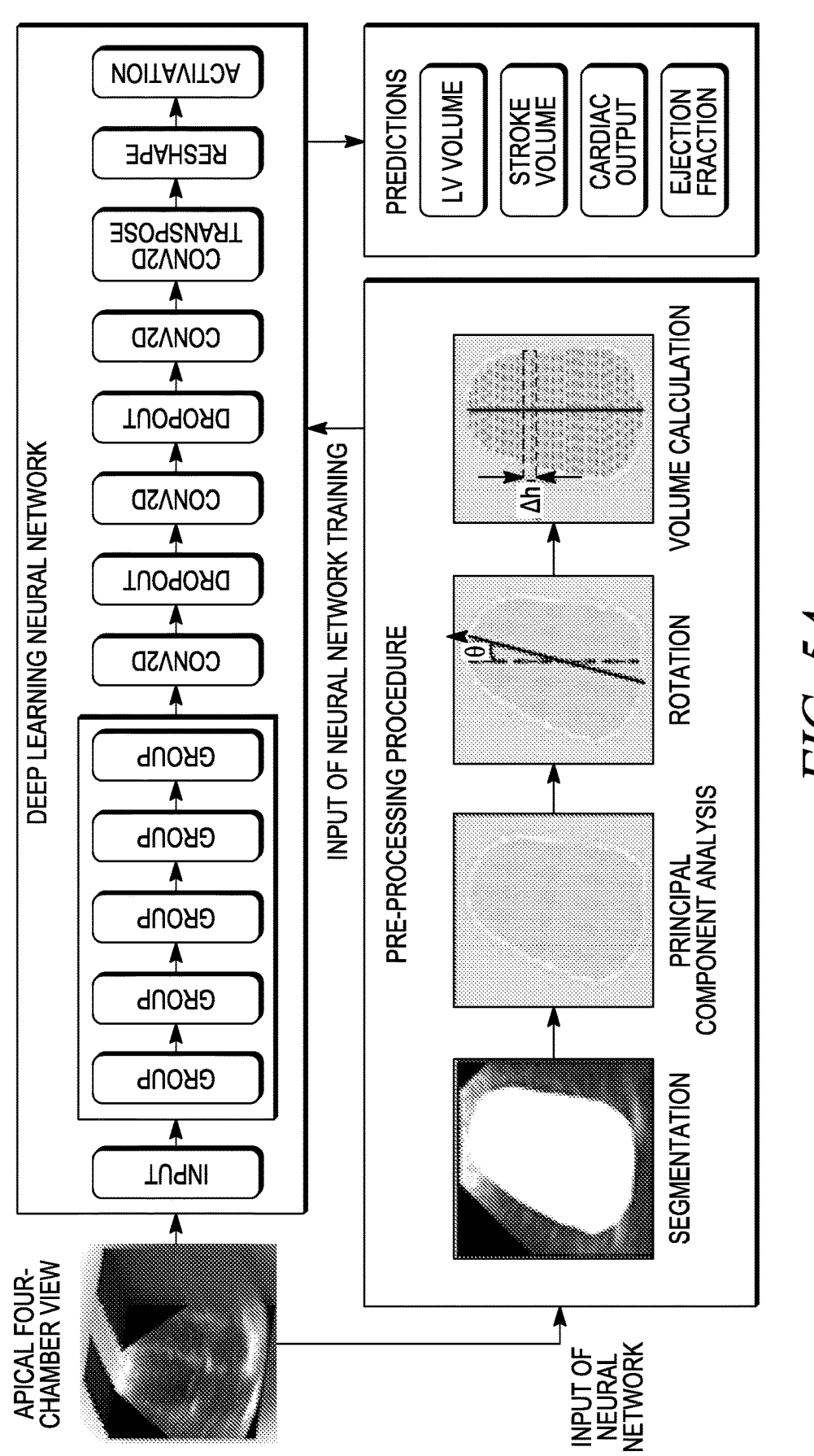
FIGS. 5(A)-5(H) illustrate the automatic image processing by deep learning.
Figure 36:
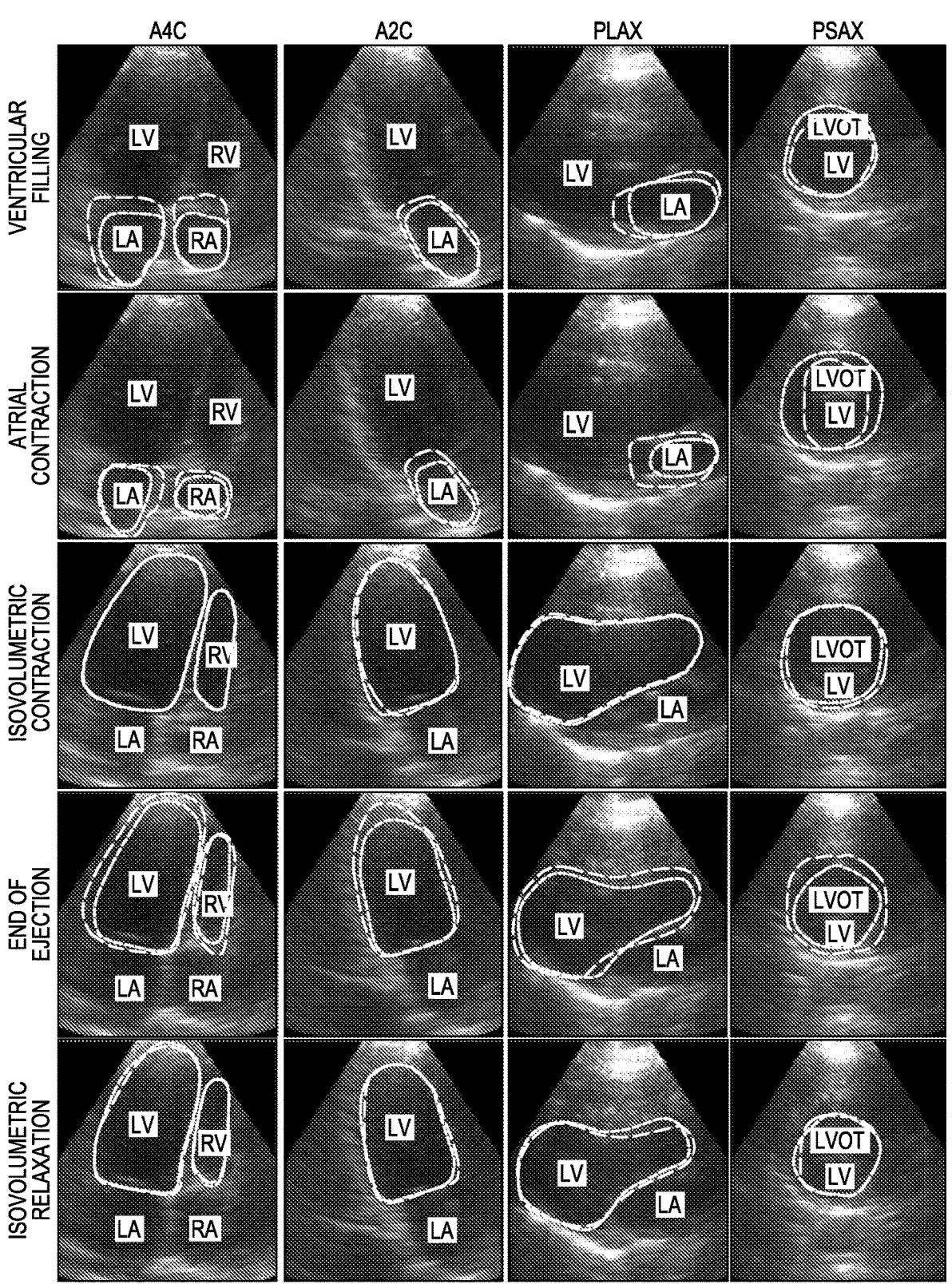
FIG. 36 shows different phases in a cardiac cycle obtained from B-mode imaging.
Figure 37A:
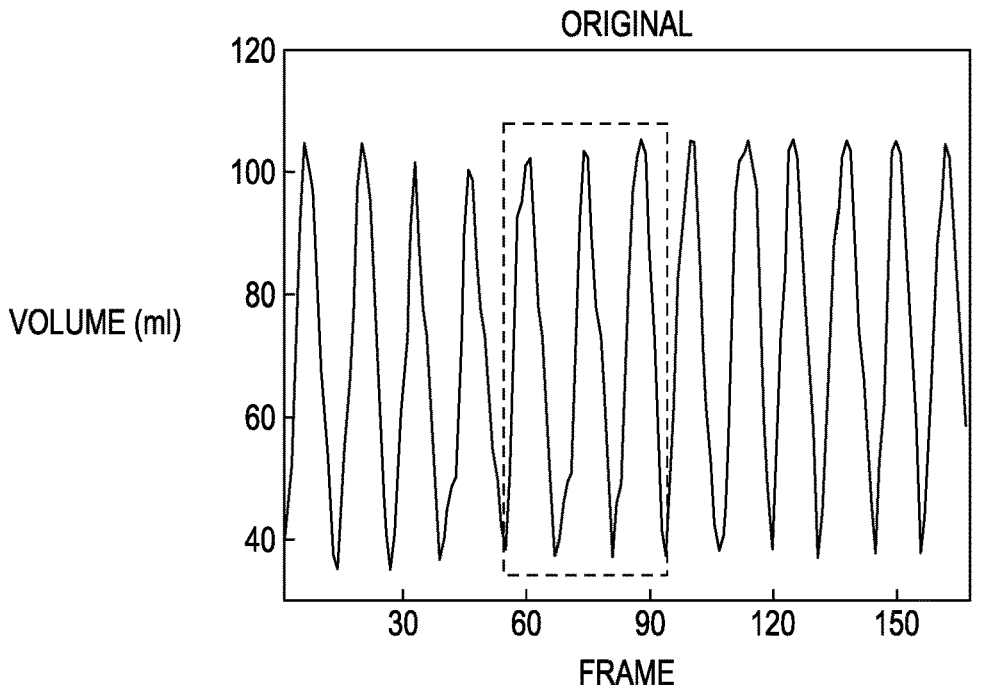
FIGS. 37(A)-37(F) present data representing validation of the imputation algorithm.
Figure 37B:
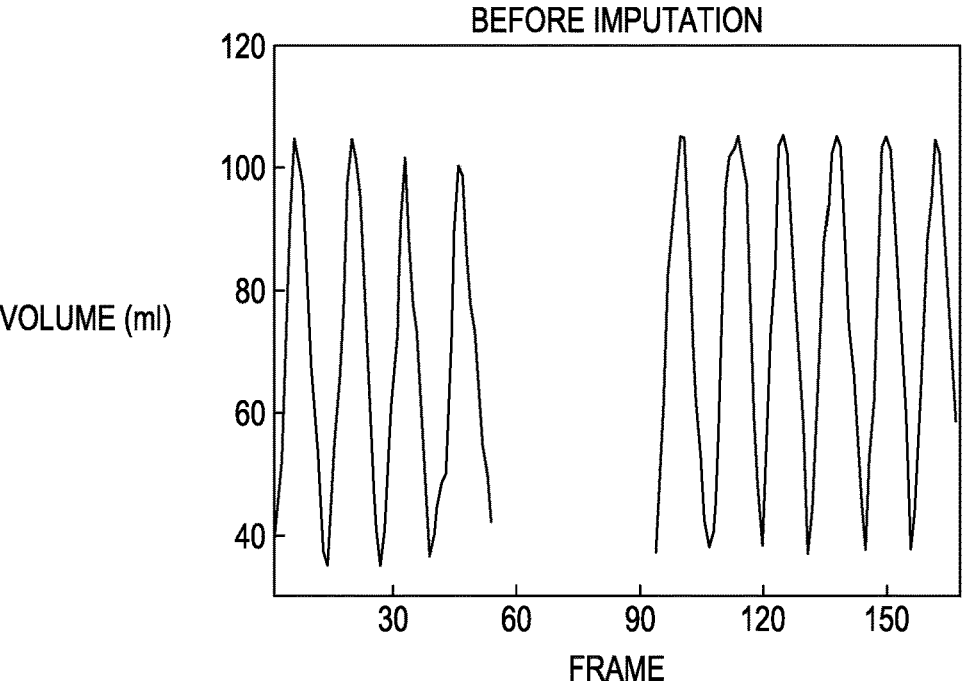
Figure 37C:
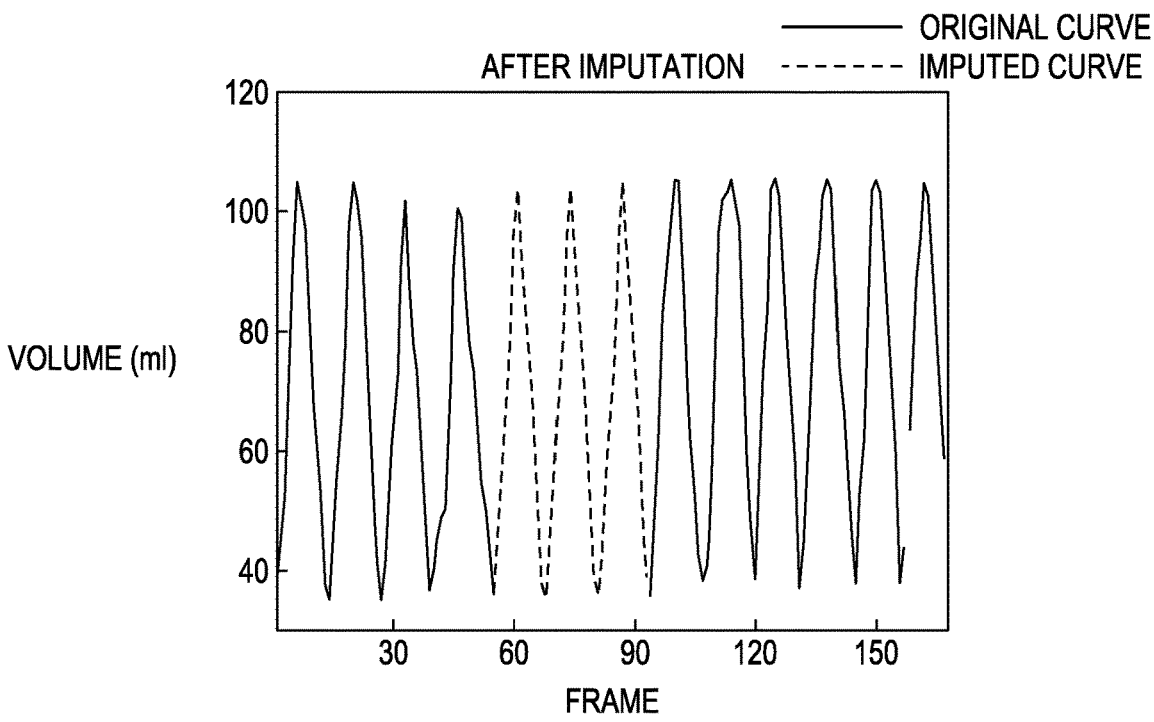
Figure 37D:
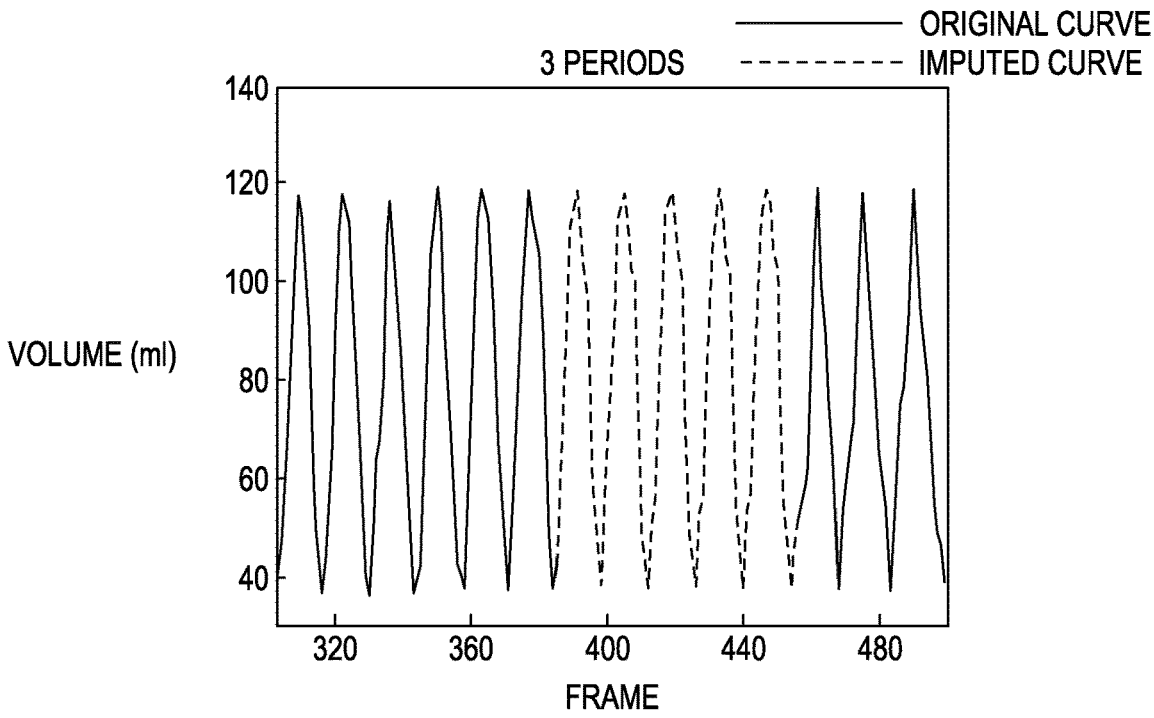
Figure 37E:
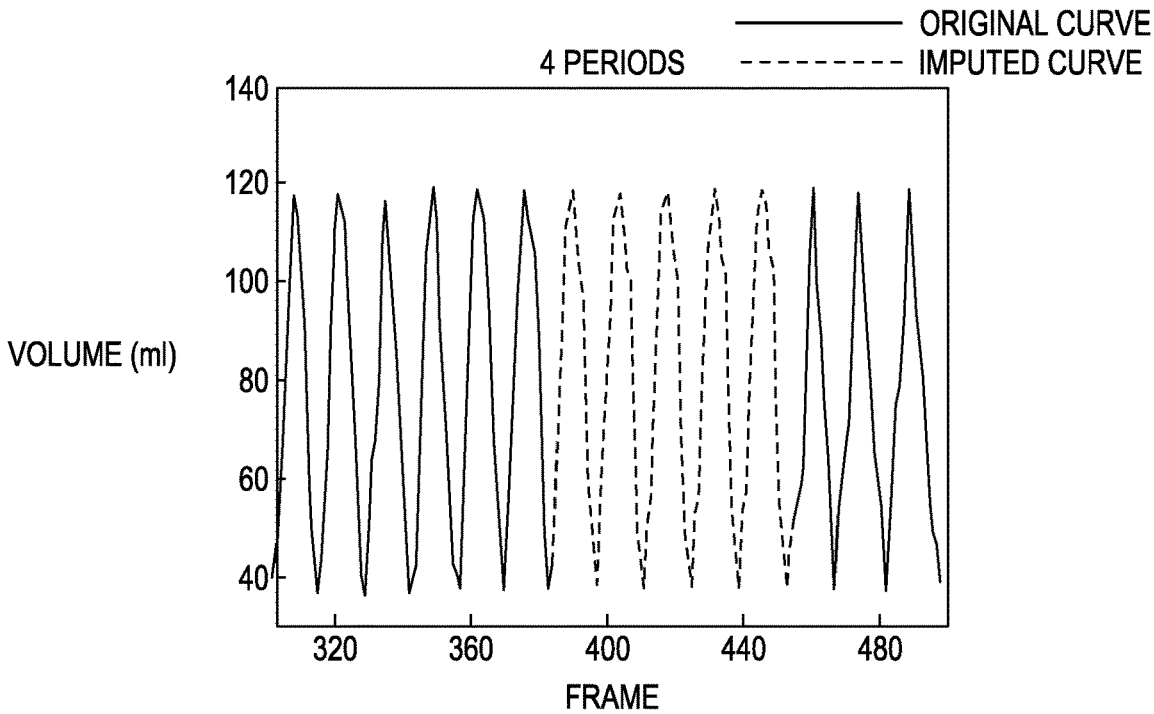
Figure 37F:
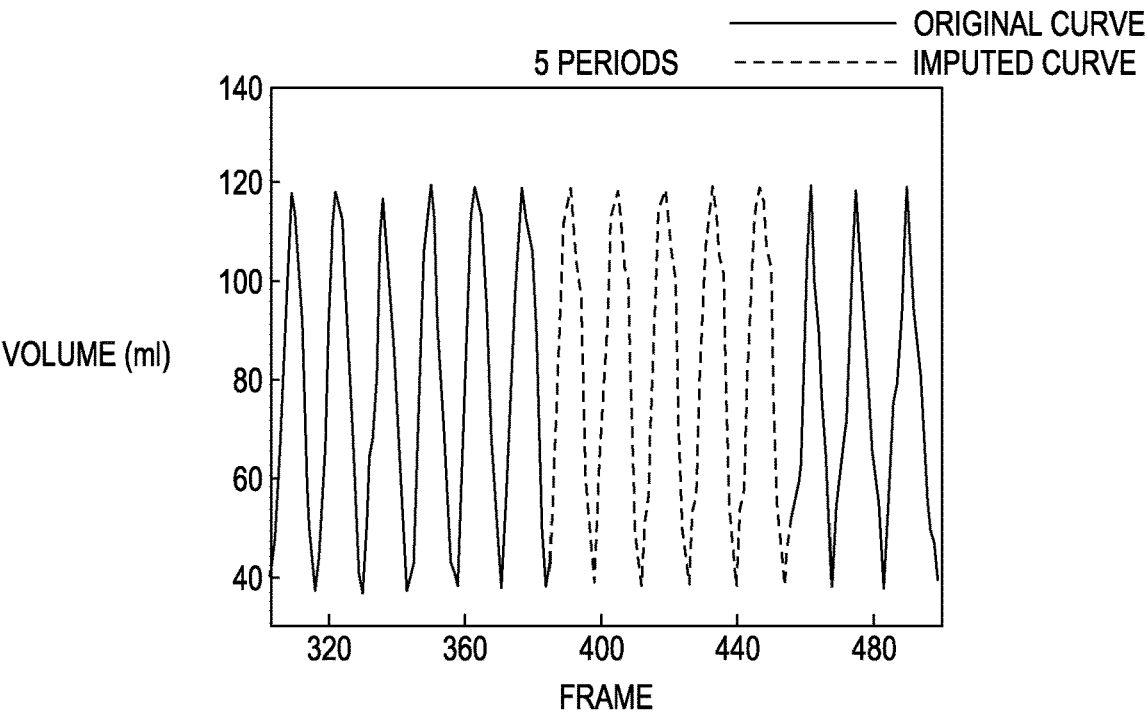

To automize the image processing process, we applied a deep learning neural network to extract key information (e.g., the left ventricular volume in apical four-chamber view B-mode images) from the continuous data stream (see FIG. 5A, which shows the schematic workflow. Some of the images go through pre-processing procedures including seg-mentation, principal component analysis, rotation, and vol-ume calculation as the input for training the FCN-32 model. The trained model accepts the rest of the images as input and automatically predicts the left ventricular volume, based on which stroke volume, cardiac output, and ejection fraction are derived. See also FIG. 31 discussed below). We evalu-ated different types of deep learning models based on Mean-Intersection-Over-Union, a critical metric in bench-marking object detection (see FIG. 32, discussed below), and the output waveforms of the left ventricular volume (see FIG. 33, discussed below). According to qualitative and quantitative analyses, FCN-32 outperforms all other models in this study (materials and methods, FIG. 34). We used data augmentation to expand the limited labelled dataset to further improve the FCN-32 performance (FIG. 36, materi-als and methods). (see FIG. 34, described below).

Figure 5B:
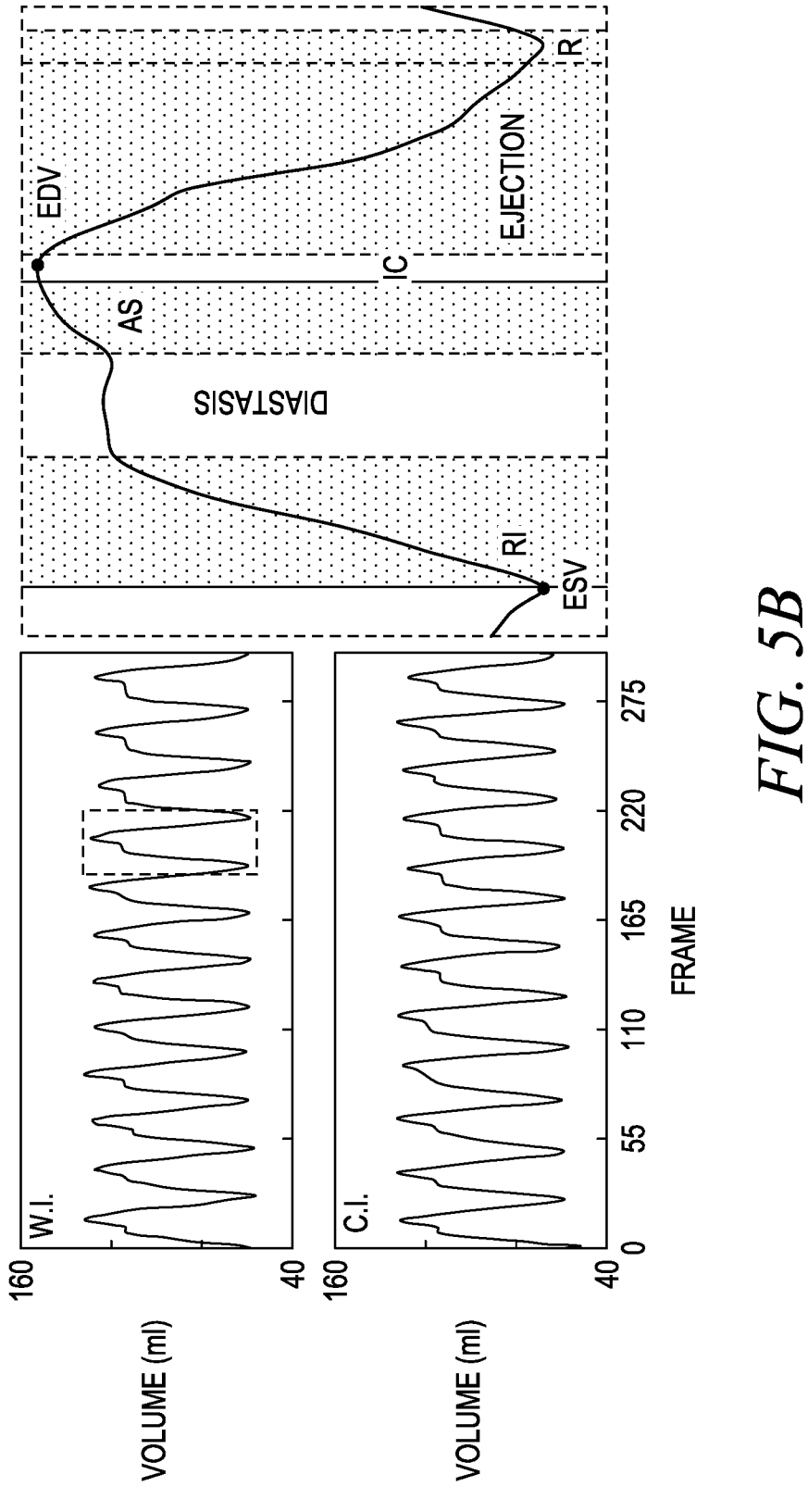
Figure 5C:
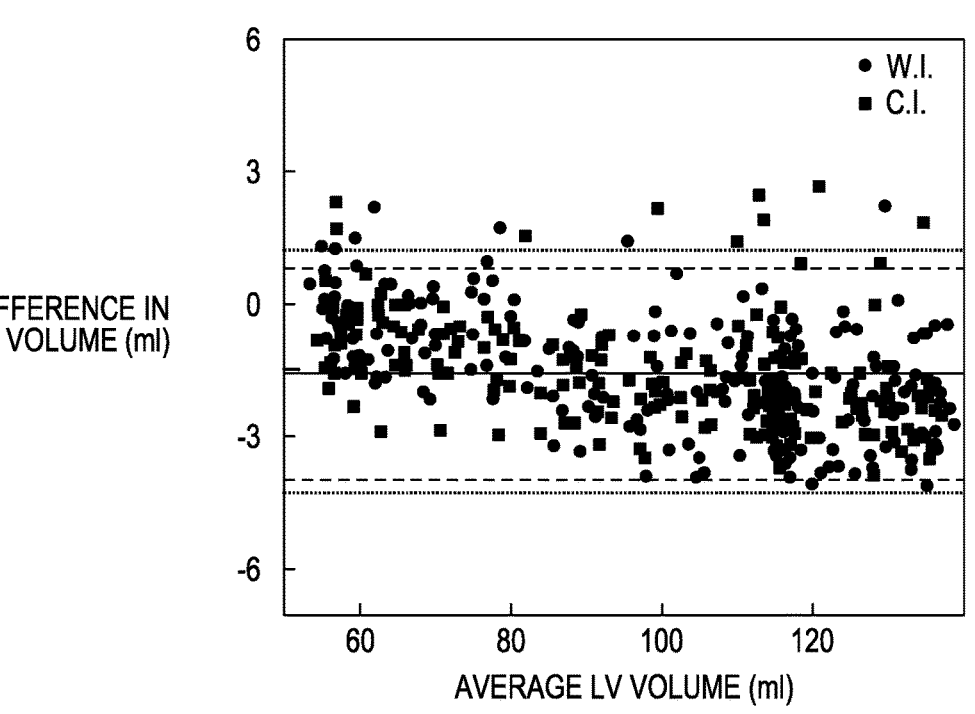
Figure 5D:
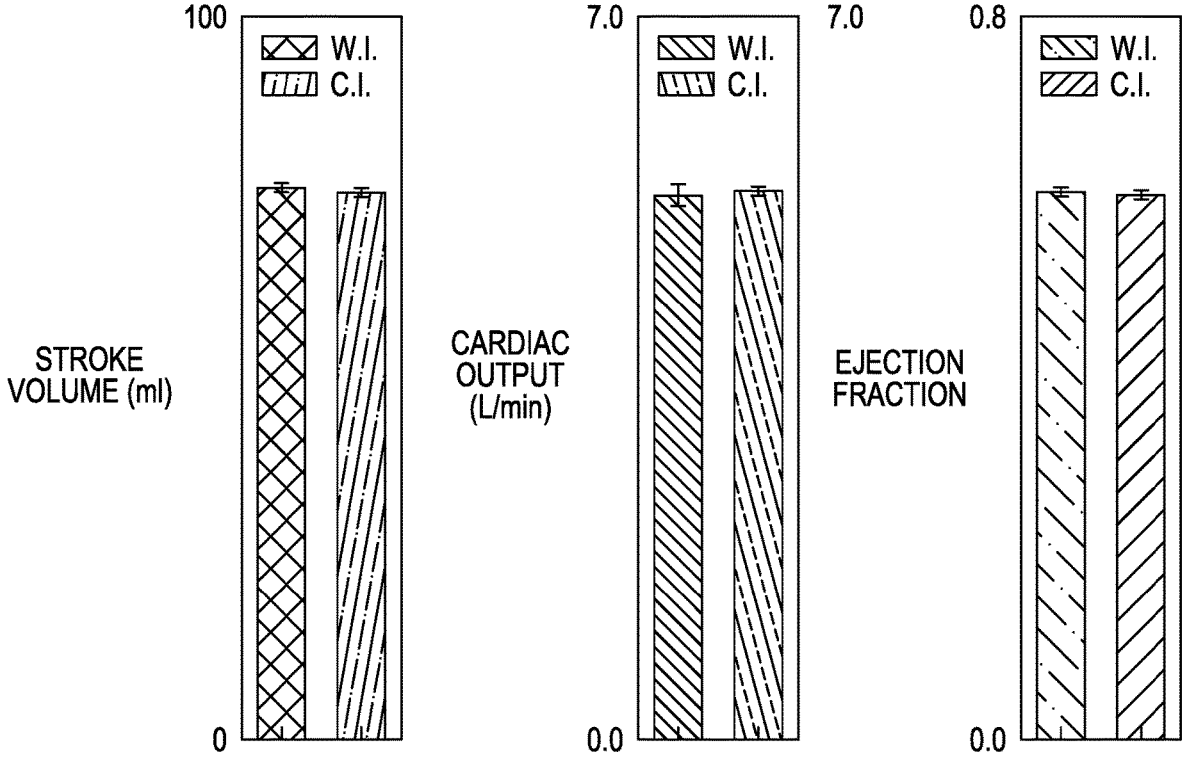

The output left ventricular volumes of the FCN-32 model for the wearable and commercial imagers show similar waveform morphologies (see FIG. 5B left, which shows the left ventricular volume waveform of a subject in a steady state generated by the FCN-32 model from both the wear-able and commercial imagers), reflecting the steady cardiac performance in a static. From the waveforms, corresponding phases of a cardiac cycle can be clearly identified (FIG. 5B right, which shows an illustration of one detailed cardiac cycle, where critical features are labelled left ventricular volumes; see also FIG. 36, discussed below). Bland-Altman analysis gives a quantitative comparison between the model-generated and manually labelled left ventricular volumes (see FIG. 5C, which shows a Bland-Altman analysis of the average of (x axis) and the difference between (y axis) the model-generated and manually labelled left ventricular vol-umes for the wearable and commercial imagers. Upper and lower dashed lines indicate 95% confidence interval. Solid lines indicate mean differences.). For both imagers, over 95% of the datapoints are within the 95% confidence inter-val, indicating a stable and reliable performance of the FCN-32 model. The mean differences in the left ventricular volume are both ~−1.5 ml, which is acceptable for standard medical diagnosis. We then derived stroke volume, cardiac output, and ejection fraction from the left ventricular volume waveforms. There is no significant difference in the averages or standard deviations between the two devices (see FIG. 5D, which compares the stroke volume, cardiac output, and ejection fraction extracted from results by the wearable and commercial imagers.). The results verified the comparable performance of the wearable imager to the commercial imager.

Figure 5E:
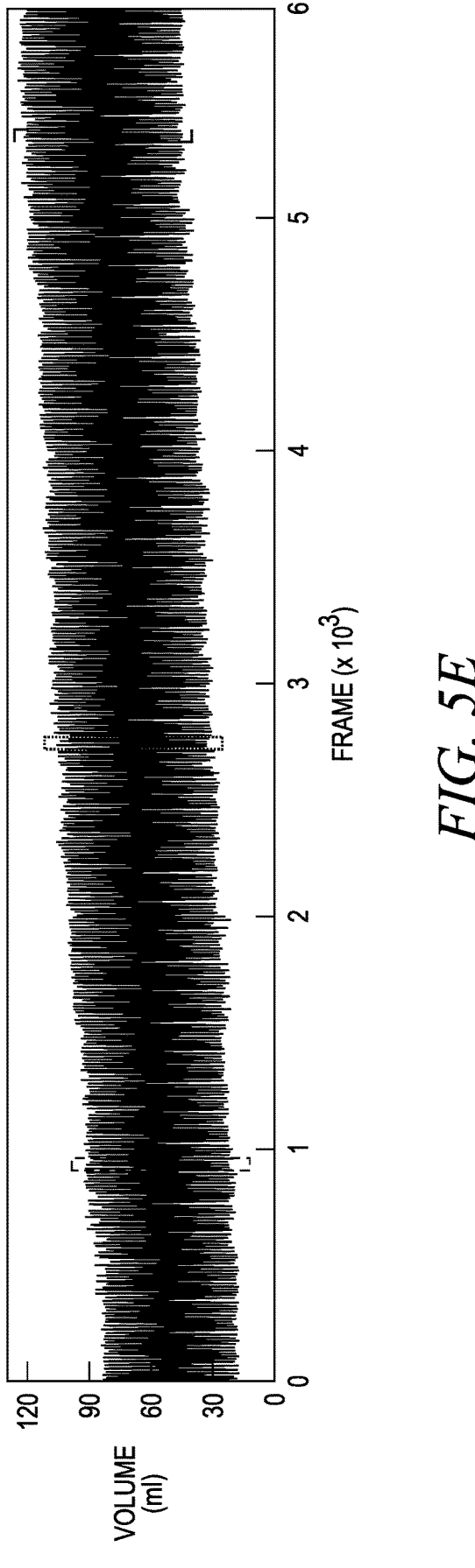
Figure 5F:
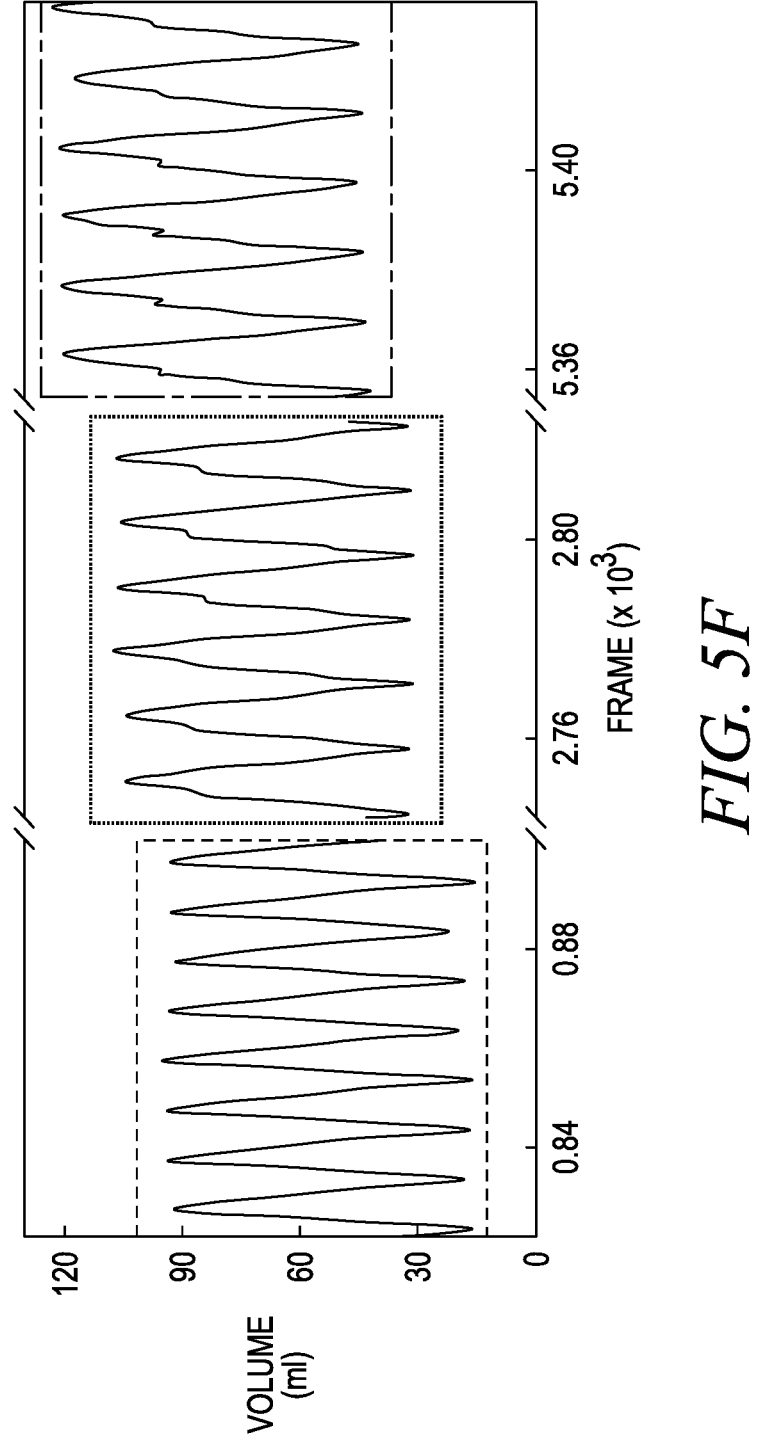
Figure 5G:
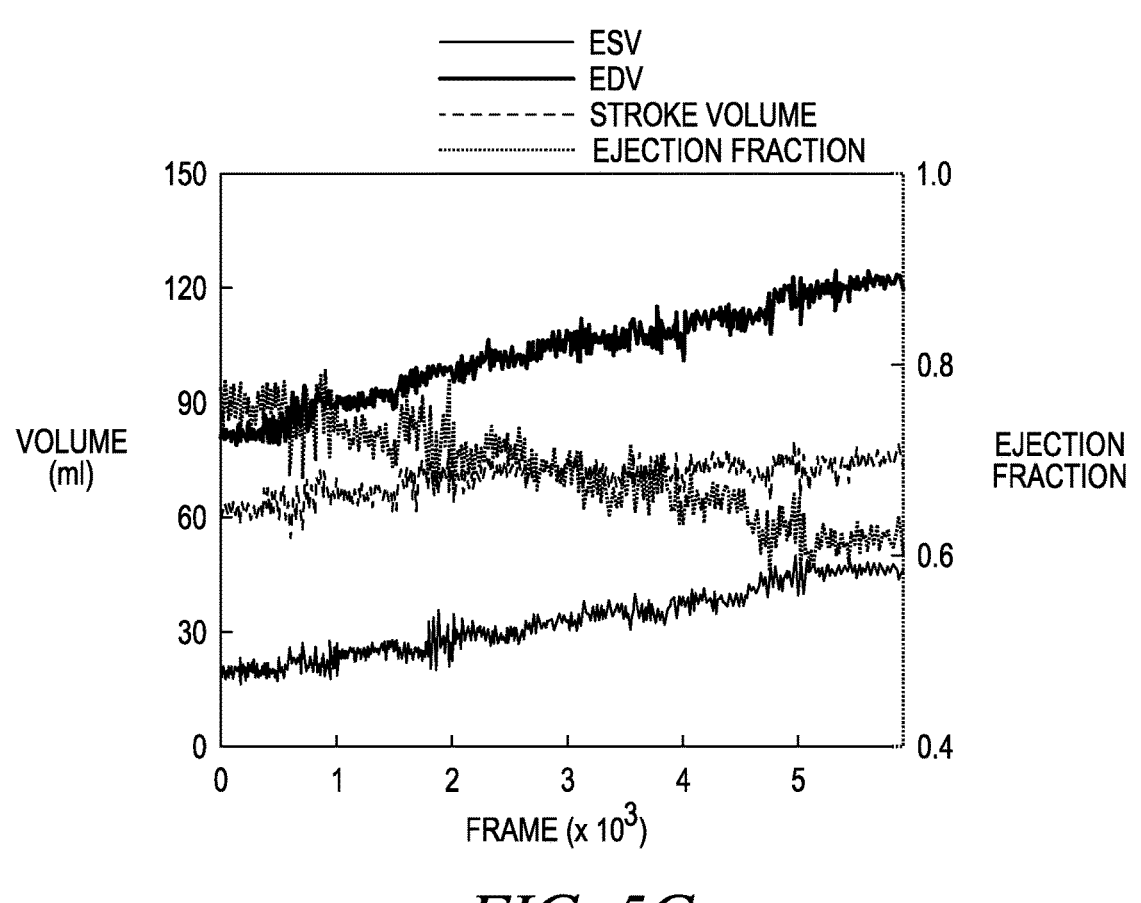
Figure 5H:
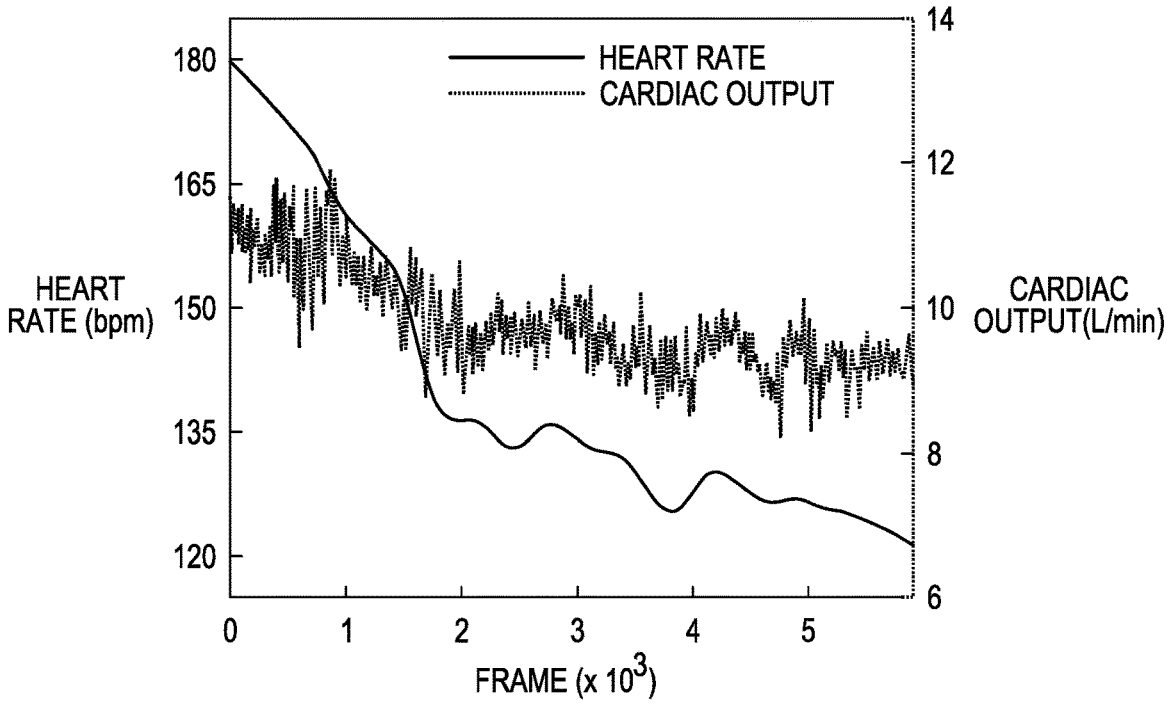

We extracted the left ventricular volume from recordings in the recovery stage of stress echocardiography (see FIG. 5E, which shows the model-generated waveform of the left ventricular volume of the subject in the recovery stage). When the heart was sometimes blocked by the deep-breath-ing lung, we used an image imputation algorithm to comple-ment the blocked part in these images. The acquired wave-form shows an overall increasing trend in the left ventricular volume. FIG. 5F illustrates in detail three representative sections of the recording taken from the beginning, middle, and end of the recovery stage. In the initial section, the diastasis stage is barely noticeable because of the high heart rate. In the middle section, the diastasis stage becomes visible. In the end phase, the heart rate drops significantly. The end diastolic and end systolic volumes are lower than usual in the initial section and gradually recovers to the normal range in the end section, because the slowing heart-beat allows more time for blood to fill the left ventricle (see FIG. 5G, which shows ESV, EDV, stroke volume, and ejection fraction waveforms derived from the dynamic left ventricular volume. Note that the following terminology is used in FIG. 5: LV: left ventricular; W.I.: wearable imager; C.I.: commercial imager; RI: rapid inflow; AS: atrial systole; ESV: end systolic volume; EDV: end diastolic volume; and IR: isovolumetric relaxation). The stroke volume rises from ~60 ml to ~70 ml, indicating that the end diastolic volume increases slightly faster than the end systolic volume (see FIG. 5G). The ejection fraction decreases from ~80% to ~60%, as heart contraction decreases during the recovery (FIG. 5G). The cardiac output decreases from ~11 to ~9 l/min (see FIG. 5H, which shows cardiac output and heart rate waveforms derived from the dynamic left ventricular volume), indicating that the decrease in heart rate from ~180 bpm to ~120 bpm overshadowed the increase in stroke volume.

Discussion

Echocardiography is crucial in the diagnosis of cardiac diseases, but the current implementation is cumbersome and limits its application in continuous monitoring. Key hemo-dynamic parameters such as the stroke volume, cardiac output, and ejection fraction, reflect the systemic oxygen transport performance from the heart, which influences several physiological equilibriums in the body. Therefore, continuous cardiac monitoring is highly desirable in critical care, cardiovascular disease management, and sports sci-ence. However, conventional methods to continuously monitor these indices are invasive or semi-invasive, which are resource intensive and limit their use in bedside surveil-lance for critically ill or surgery patients. Their invasive nature is associated with risk of morbidity and mortality. Emerging non-invasive methods can provide estimates of the cardiac output, but their accuracy remains questionable. The wearable imager with deep learning addresses these technological challenges by automatically generating wave-forms of all cardiac volume-related indices based on chal-lenges images of the heart in a non-invasive manner. This capability was unprecedented in conventional clinical prac-tice, and the non-invasiveness can extend potential benefits to the outpatient and athletic populations.

The implications of this technology go far beyond imag-ing the heart, as it can be generalized to image other deep tissues, such as the inferior vena cava, abdominal aorta, spine, and liver (see FIG. 39, discussed below). For example, as demonstrated in an ultrasound guided biopsy procedure on a cyst phantom (see FIG. 39, discussed below), the two orthogonal imaging sections present the entire biopsy process simultaneously, freeing up one hand of the operator.

While various examples of a wearable imaging device have been described above, the devices and methods described herein are not limited to these examples. In general, the wearable imaging device is a stretchable and flexible imaging device that conforms to a shape of patient tissue to which it is attached. The imaging device includes a stretchable and flexible encapsulation substrate and superstrate, an ultrasound transducer array, a stretchable and flexible electrical interconnect layered structure and a controller. The stretchable and flexible encapsulation substrate is configured to be removably attachable to tissue of a patient. The ultrasound transducer array has a plurality of transducer elements disposed between the substrate and superstrate for transmitting and receiving ultrasound waves. The transducer elements are arranged so that data from the received ultrasound waves is processable into an ultrasound image of specified tissue of a patient. The stretchable and flexible electrical interconnect layered structure is disposed between the superstrate or substrate and the ultrasound transducer array and is operatively coupled to the transducer elements such that the stretchable and flexible electrical interconnect layered structure is configured to address the transducer elements. The controller is configured to implement a beamforming algorithm. The controller is in operative communication with the stretchable and flexible electrical interconnect layered structure for generating the ultrasound images of the specified tissue of the patient.

In some embodiments, the beamforming algorithm is selected from the group including a plane-wave algorithm, a mono-focus algorithm, a plane-wave compounding algorithm and a wide-beam compounding algorithm.

In some embodiments, the transducer elements in the ultrasound transducer array are arranged into a plurality of linear arrays that overlap and cross one another.

In some embodiments, the plurality of linear arrays includes two linear arrays for generating simultaneous bi-plane ultrasound images.

In some embodiments, the plurality of linear arrays includes three or more linear arrays for generating three or more simultaneous ultrasound images representing different image planes.

In some embodiments, the two linear arrays are orthogonal to one another.

In some embodiments, each of the linear arrays has a length and width each defined by at least two transducer elements.

In some embodiments, the transducer elements in the plurality of linear arrays have a pitch between 0.01 mm and 2 cm.

In some embodiments, the plurality of linear arrays each have a length between 0.5 mm and 50 cm.

In some embodiments, the transducer array has an aperture-to-pitch (i.e., overall length to pitch) ratio of 30-60.

In some embodiments, the ultrasonic transducer array is a two-dimensional array configured to generate three-dimensional volumetric ultrasound images.

In some embodiments, the ultrasonic transducer array is a periodic or nonperiodic array.

In some embodiments, the stretchable electrical interconnect layered structure comprises liquid-metal electrodes that include a multilayered liquid metal in a polymer matrix.

In some embodiments, the stretchable and flexible electrical interconnect layered structure comprises carbon nanotubes.

In some embodiments, the transducer elements are piezoelectric transducer elements.

In some embodiments, the piezoelectric transducer elements comprise a 1-3 composite material.

In some embodiments, the piezoelectric transducer elements comprise a PMN-PT single crystal.

In some embodiments, the transducer elements are piezoelectric micromachined ultrasonic (PMUT) or capacitive micromachined ultrasonic (CMUT) transducer elements.

In some embodiments, the stretchable and flexible imaging device of claim 1 further comprises an electromagnetic shielding layer located between the superstrate and the stretchable electrical interconnect layered structure.

In some embodiments, the stretchable and flexible encapsulation substrate and superstrate comprises a triblock copolymer.

In some embodiments, the specified tissue of the patient is an internal organ of the patient.

In some embodiments, the patient tissue to which the stretchable and flexible encapsulation substrate is configured to be removably attachable is an epidermis of the patient.

In some embodiments, the controller is electrically and operatively coupled to the stretchable electrical interconnect layered structure through an electrical impedance matching circuit.

In some embodiments, the stretchable and flexible electrical interconnect layered structure is operatively coupled to the transducer elements such that the stretchable and flexible electrical interconnect layered structure is configured to individually address the transducer elements In another embodiment, a method of generating an ultrasound image of patient tissue of a patient is provided. In accordance with the method, a stretchable and flexible ultrasound imaging device is attached in a removable manner to the patient tissue of the patient The stretchable and flexible ultrasound imaging device includes: a stretchable and flexible encapsulation substrate and superstrate; an ultrasound transducer array having a plurality of transducer elements disposed between the substrate and superstrate; and a stretchable electrical interconnect layered structure disposed between the superstrate and the ultrasound transducer array and being in operative communication with the transducer elements such that the stretchable electrical interconnect layered structure is configured to address each of the transducer elements. Ultrasound waves are transmitted into the patient using the transducer elements. Ultrasound waves are then received from the patient using the transducer elements. An ultrasound image of the specified tissue of the patient is generated and displayed using the received ultrasound waves.

In some embodiments, the specified tissue is an internal organ of the patient.

In some embodiments, the internal organ is the heart and the ultrasound image is an echocardiogram.

In some embodiments, the specified tissue is selected from the group consisting of an inferior vena cava, abdominal aorta, spine, and liver.

In some embodiments, the transmitting employs a beamforming scheme selected from the group including a plane-wave algorithm, a mono-focus algorithm, a plane-wave compounding algorithm and a wide-beam compounding algorithm.

In some embodiments the receiving employs a beamforming scheme selected from group including a delay and sum algorithm, a delay multiply and sum algorithm, and a filtered-delay multiply and sum algorithm.

In some embodiments, the echocardiogram of the heart is based on four standard views that include an apical four-chamber view, an apical two-chamber view, a parasternal long axis view and a parasternal short axis view.

In some embodiments, the beamforming scheme employs a phase correction algorithm to compensate for deformation of the transducer array when attached to the patient tissue.

ILLUSTRATIVE EMBODIMENTS AND METHODS

Presented below are additional characteristics and features of various embodiments of the wearable imaging device described herein and a discussion of illustrative use cases for such embodiments.

1. Significance of the Wearable Imager for Cardiac Health Management 1.1 End-Systolic Volume (ESV), End-Diastolic Volume (EDV), Heart Rate, Stroke Volume, Cardiac Output, and Ejection Fraction More than a million patients are admitted annually to U.S. hospitals with acute heart failure alone, together with a high median percentage of intensive care unit admission of 10% and a high in-hospital mortality rate around 4% to 7%. Also, cardiovascular failure is one of the leading causes of death in intensive care units and nearly one quarter of all deaths in intensive care units are attributed to it.

Accurate assessment of subtle changes in cardiac functions is essential for health management and disease prevention for healthy people, as well as diagnosis of pathogenesis and interventions for patients. The signals we can use to evaluate the cardiac functions include the ESV, EDV, heart rate, as well as their derivative signals such as stroke volume, cardiac output, and ejection fraction. ESV and EDV can be obtained by processing the apical four-chamber view B-mode images using a deep learning model. The heart rate can be observed based on the period of contraction in M-mode images. Based on these values, those derivative signals can be calculated by:

$$\text{Stroke Volume} = EDV - ESV \qquad (1)$$

$$\text{Cardiac Output} = \text{Stroke Volume} * \text{Heart Rate} \qquad (2)$$

$$\text{Ejection Fraction} = \frac{\text{Stroke Volume}}{EDV} \qquad (3)$$

Stroke volume indicates the absolute blood volume the left ventricle can pump out in a single stroke. The cardiac output indicates the absolute blood volume the left ventricle can pump out every minute. Ejection fraction indicates the relative fraction of the blood in the left ventricle that the heart can pump out in a single stroke. Altogether, these indices provide insight into the capability of the heart to deliver blood to tissues throughout the body.

1.2 Cardiac Functions and Common Pathologies

Cells in the human body all require a steady supply of oxygen and nutrient for their metabolism. The cellular metabolic rates are not static, but rather are subject to constant fluctuations. Thus, the heart must not only be able to produce a cardiac output meeting the metabolic demands of the body at a given time but also do so efficiently, such that enough headroom is maintained to accommodate any heightened metabolic rates that can occur due to circumstances such as strenuous exercise. The existence of a nonzero end-systolic volume itself also serves a similar purpose as a buffer. Thus, the occurrence of heart failure is marked either by an inability of the heart to provide a cardiac output meeting the metabolic demands of the body, and/or a compromised efficiency in function and consequent lack of headroom.

There are two forms of heart failure: systolic and diastolic. As the names suggest, systolic heart failure results from the heart's lack of ability to pump blood during systole, while diastolic heart failure results from the heart's lack of ability to fill with blood during diastole.

During systole, the goal of the left ventricle is to eject as much of its blood volume as possible. The ability of the left ventricle to do so can be viewed as a function of three factors: (a) the contractility of the myocardium, (b) the afterload in the left ventricle, and (c) structural integrity of the left ventricle.

(a) contractility acts as the driving force for blood flow out of the left ventricle and through the aortic valve. If the contractility is compromised, the left ventricle's capacity to eject blood will be reduced. This can occur due to conditions such as dilated cardiomyopathy or ischemic heart disease, which cause the myocardium to contract weakly. Alternatively, it can be a result of pathologies such as arrhythmia, in which the myocardium activates asynchronously rather than produces a single, strong impulse during systole.

(b) Afterload is the amount of resistance encountered by the left ventricle as it attempts to contract. The more resistance the left ventricle encounters, the more difficult it will be to eject blood. This can result from conditions such as aortic stenosis, where the aortic valve does not open fully and restricts the blood flow, or hypertension, in which there is elevated pressure in the left ventricle resisting contraction.

(c) Structural integrity of the left ventricle is prerequisite for its functions. For example, a mitral valve defect that results in an improper seal between the left ventricle and left atrium can cause blood to backflow into the left atrium during systole, instead of flowing through the aortic valve towards the rest of the body.

During diastole, the goal of the left ventricle is to fill with as much blood as possible. This ensures that there is enough blood available to be pumped out afterward, during systole. Similar to systole, the diastolic function can also be broken down into three contributing factors: (a) the distensibility of the left ventricle, (b) external compression, and (c) structural factors.

(a) In diastole, the distensibility of the left ventricle serves as the driving force, allowing it to expand and be filled with blood. A stiffer or thicker myocardium loses its ability to expand, resulting in decreased distensibility. For example, the protein deposits caused by amyloidosis can lead to this effect. Hypertrophy can also be caused by chronic hypertension as a result of the heart working against high afterloads. Gradual loss of distensibility is also a natural result of aging.

(b) External compression acts as the resistive force against the distensibility of the left ventricle. External compression restricts the volume of blood that can be filled, leading to diastolic heart failure. External compression is introduced from regions external to the left ventricle, such as the pericardium in constrictive pericarditis and cardiac tamponade. It can even come from the right ventricle, as is the case in cor pulmonale, in which right ventricular failure has excessive volume.

This dilation of the right ventricle creates an external compression acting on the left ventricle.

(c) Structural factors can also affect diastole, in the form of obstructions to filling. Obstructions prevent the left ventricle from filling optimally during diastole, leading to a reduction of the end-diastolic volume. For example, mitral stenosis can prevent the mitral valve from opening optimally, reducing blood flow into the left ventricle from the left atrium. A left atrial myxoma located in the way of the mitral valve could also cause a similar effect.

Additionally, diastolic heart failure can also result from systolic heart failure. When the ejection fraction decreases due to systolic heart failure, causing an initial drop in stroke volume and cardiac output, the heart may compensate by increasing the end-diastolic volume with higher filling pressure through neurohormonal pathways that increase the vascular tone and intravascular volume. This invokes the Frank-Starling relationship by creating a higher pre-load, allowing the stroke volume to return back to normal levels while the ejection fraction remains low. Because diastolic filling must occur with elevated pressure if the cardiac output is to be maintained, diastolic heart failure can happen in this situation. As with nearly all human physiology, this is one of many examples showing how the final indices that we observe are often the result of a long cascade of interactions.

As such, the numerical indices (i.e., ESV, EDV, heart rate, stroke volume, cardiac output, and ejection fraction) by themselves can only point us towards whether systolic/diastolic heart failure has occurred, or possibly both have occurred. For example, in systolic heart failure, one cannot determine whether it stems from lack of contractility, increased afterload, or loss of structural integrity, based on the numbers alone. Therefore, while these indices may not provide a specific diagnosis, they serve as highly efficient quantitative indicators for the early detection of a broad range of cardiovascular diseases. The ability to continuously monitor these indices opens the opportunity for more comprehensive examinations to be performed in a timely manner.

1.3 B-Mode and M-Mode Images

In this study, we demonstrate direct ultrasound B-mode and M-mode imaging of cardiac structures. This capability of the wearable imager is valuable in providing a more detailed diagnosis after an initial indication of cardiovascular diseases from the numerical indices. A vast number of factors contributing to heart failure can be identified visually just from imaging the heart continuously. For example, ischemia may result in death of myocardial cells, producing effects such as fibrillation and hypokinesia/akinesia, which can be easily observed in continuously recorded images. Features related to the structural integrity of the heart and obstructions to filling may also be seen, such as valvular stenosis, valvular regurgitation, septal defects, and left atrial myxoma. Hypertrophic cardiomyopathy can result in an obvious thickening of the myocardium that can be seen on the ultrasound recording, while dilated cardiomyopathy results in a visible thinning of the myocardium and dilation of the left ventricle. Hypertrophic cardiomyopathy can also be differentiated from pathologies like amyloidosis due to the extreme brightness of the amyloid proteins relative to the myocardium on the ultrasound image. These are a few notable examples of the vast range of diseases that can be diagnosed conclusively through wearable imaging.

In this study, four standard B-mode ultrasound views of the heart were implemented: parasternal long axis, parasternal short axis, apical four chamber, and apical two chamber. Parasternal long and short axis views are orthogonal, so are apical four and two-chamber views. Each of these views provides a different perspective of the heart, with its own viewing angle and set of structures, allowing for the most comprehensive heart investigations. In addition, imaging the heart from these standard views allows for a more accurate representation of cardiac structural dimensions. Imaging from other angles can also reveal internal structures, but the displayed dimensions may have deviations from what clinicians normally measure. From the four views, the symptoms related to major abnormalities in cardiac functions such as changes in myocardial thickness can be easily and accurately observed. Furthermore, diseases and activities may increase the heart rate, leading to faster valvular velocities, which could be qualitatively estimated through a frame-by-frame observation method: the distance of the valve movement can be detected from frames in B-mode images. A faster valvular velocity leads to fewer frames to reach a same distance.

2. Why a Wearable Device and why Ultrasound should be Used 2.1 why Wearable Device should be Used Not all diseases have regular and sustained symptoms or pathologies. The insufficient sampling of signals would possibly miss transient but critical signals and thus provide less confidence to the diagnostic results. Thus, long-term monitoring is highly desired for those that are sporadic and barely predictable. Besides stress echocardiography we will study in detail, there are several other use cases that can benefit from wearable long-term monitoring.

Sinus arrhythmia produced by the irregular release of impulses from the sinoatrial node is one typical example. Being prevalent among senior people, arrhythmia is the root cause of a variety of other symptoms and diseases, such as blood clotting in the heart, hypotension that leads to dizziness, and sudden death. Sinus arrhythmia includes sinus tachycardia, bradycardia, and arrest. Sinus arrhythmias may not have symptoms during the limited examination time because it could be sporadic and barely predictable in daily life. Hence, prolonged tracking time can help record the timing and syndromes for a better diagnosis. Also, while it is simple to detect symptoms with a quick test, it is imprudent to instantly diagnose signs as illness and intervene immediately. This is because sinus rhythm is very sensitive to factors such as mood and respiration, and after a while the variations automatically revert to normal. Existing approaches for monitoring arrhythmia are plagued by various problems. Auscultation of the heartbeat with a stethoscope is a general but nonspecific measurement, because abnormity like premature or abnormal beats do not always produce an audible pumping and may be missed and misdiagnosed. Electrocardiogram could be more effective and accurate. It provides abundant information because different types of arrhythmias have different reflections on electrocardiogram. Doctors can tell the type from electrocardiogram directly and thus more quickly make a move. But motion artifacts introduced by body movement will distort electrocardiogram signals badly, which challenges signal accuracy in daily monitoring. Additionally, the lack of structural information prevents electrocardiogram from providing comprehensive diagnosis.

Photoplethysmography fails to provide sufficient information for further diagnosing the type of arrhythmia, because it can only monitor the heart rate. There are some studies on building mathematical models to correlate photoplethysmography waveforms to the arrhythmia type, but the result is not accurate enough. Other invasive methods may be less commonly used.

Another example is paroxysmal atrial fibrillation, which intermittently occurs as a disorder of cardiac rhythm. This disease also suffers from the same problem that limited examination time may be not enough for a thorough diagnosis, and this could introduce horrible result. Paroxysmal atrial fibrillation may develop into chronic atrial fibrillation, which occurs more frequently, a direct result of misdiagnosis. Moreover, a common error in clinical management of atrial fibrillation is to treat chronic sustained atrial fibrillation and paroxysmal atrial fibrillation similarly, despite some differences in management objectives. Atrial fibrillation is often associated with a high risk of morbidity and mortality from heart failure, stroke, and thromboembolic complications. Thus, the failure of detecting the early stage of paroxysmal atrial fibrillation is disastrous.

Similarly, coronary heart disease may also be undetectable in a transient test. Coronary heart disease is caused by plaque built-up near the coronary arteries, which limits the blood supply. Coronary heart disease often develops over decades and is frequently ignored because no symptoms are detected. However, the unnoticed coronary heart disease could lead to an acute heart attack due to the blockage of the artery, which is extremely lethal and results in a high mortality. This heart attack caused by undetected coronary heart disease with no obvious symptoms may also be called a "silent heart attack". Silent precursors to an eminent myocardial infarction can be detected by observing segmental wall motion abnormalities in ultrasound images.

Finally, acute heart disease could barely be noticed when it is not occurring. Myocardial infarction is the lack of blood supply to myocardium, which weakens cardiac activities. Myocardial infarction has a high morbidity because many factors and triggers contribute to it, such as alcohol, physical exertion, and obesity. Myocardial infarction also has a high mortality. It cannot be effectively detected in current measuring procedures, because the short period of testing time cannot capture any signs of it unless it is occurring with symptoms.

We can summarize that previous efforts of wearable devices for non-invasive heart monitoring are mainly categorized into three fields: electrical probe, electromagnetic probe, and mechanical probe. Specifically, the electrocardiogram sensor for local-field potential recording for analyzing cardiac rhythm; the electrical impedance tomography sensor based on internal electrical conductivity mapping mainly for distinguishing systole and diastole phases; the electromagnetic sensor that measures stroke volume by relating the resonant frequency response of the sensor to permittivity changes caused by blood volume; the passive vibration sensor based on mechanical waves usually designed for monitoring the heart rate. However, those signals either are indirect or suffer from low spatial resolutions, from which many clinically important cardiac characteristics, such as the volume of heart chambers, the myocardium structure, and the ventricular ejection function, cannot be visually and accurately evaluated.

2.2 General Requirements of Imaging the Heart

Echocardiography, as one of the most flexible diagnostic tools revealing the structural information of the heart, is widely adopted in hospitals. However, current echocardiography focuses on short-term recordings of the heart to make a diagnosis, but transient symptoms or dysfunctions may not appear during the limited time of such recordings. Other methods based on imaging can barely provide reliable and thorough monitoring of cardiac functions, including magnetic resonance imaging, computed tomography, single-photon emission computed tomography, positron emission tomography, and optical coherence tomography. Here we briefly outline the pros and cons of each method's working principles and the rationale behind selecting the ultrasound platform in this study (table S1). We desire a device that is wearable, can target the heart, and is capable of 2D or 3D imaging with a high spatial resolution and sufficient contrast. These requirements can be summed up in a single term: wearable heart imaging, which entails the following needs.

For a modality to be suitable in wearable devices, it must first be able to be packaged into a small, lightweight, and minimal form factor that is both comfortable and non-invasive. The device must ideally provide zero hindrance to the wearer, such that there is negligible impact to their comfort or normal activities when wearing it. A sufficient penetration depth is required to target the heart non-invasively. Furthermore, the chosen modality must be robust, with no degradation in the image quality over time or large variances in image quality under different conditions encountered in daily life. Wearable devices are often desired to perform long-term monitoring, and to be frequently removed and reapplied to the wearer. Therefore, the device must also withstand the wear and tear of long-term use without a loss in image quality over time. Most importantly, the device must be safe for indefinite use—for example, the modality should not be based on ionizing radiation.

For a modality to target the heart, the major challenge to overcome is the high temporal resolution required. The heart may beat at rates of anywhere from 50 beats per minute at rest to nearly 200 beats per minute during exercise, and as such, requires a modality that can achieve temporal resolutions of at least 33 ms to image continuously in real-time. Modalities that lack sufficient temporal resolutions can result in the lack of critical diagnostic information, as well as degradation of image quality due to motion artifacts.

Lastly, to make a device useful for performing a wide range of general examination, the modality must be able to image in 2D or 3D with high spatial resolutions and good contrast. Most of the work on wearable devices has primarily targeted measures such as pulse acquisition and blood oxygen levels. While these are helpful signals, they cannot compare to the immense diagnostic value that direct 2D or 3D imaging of the heart provides. Imaging provides a great wealth of information, but its quality is crucial to being able to make these diagnoses. Poor image quality may often obscure key indicators of diseases, lead to false positives, or make it difficult to distinguish between different conditions.

Therefore, to summarize, the ideal modality should be robust, safe for long-term use, easily scaled down to wearable and portable form factors, imaging in 2D or 3D with high spatial/temporal resolutions, have a sufficient penetration depth to target the heart non-invasively, have sufficient contrast, and have a high signal-to-noise ratio. However, it should be noted that some of these requirements have trade-offs with each other. For example, by nature, imaging at high spatial resolutions will tend to sacrifice the temporal resolution, due to the larger amount of data being acquired and processed. Therefore, we can only select the most suitable modality that is able to balance all factors while meeting sufficient requirements.

2.3 Magnetic Resonance Imaging

Magnetic resonance imaging works by using a powerful magnetic field to align the protons in the body's tissues with the field. Radiofrequency waves are then pulsed to disturb this alignment, followed by a subsequent release of secondary radio waves when the protons realign with the field. These signals are collected to form images. Magnetic resonance imaging provides high tissue contrast and image quality in real-time with spatial and temporal resolutions in the range of 1.6 mm and 13-50 ms, respectively. In addition, it is non-ionizing because it uses a magnetic field and radiofrequency waves. However, magnetic resonance imaging has several obvious drawbacks that make it unsuitable for needs in this study. First, magnetic resonance imaging machines are extremely bulky and expensive and are not scalable to wearable form factors. Furthermore, the powerful magnetic field is an intrinsic requirement of the modality and can easily present a significant hazard in everyday life in addition to being incompatible with devices like pacemakers that are likely to be used by the target demographics in this study.

2.4 X-Ray Computed Tomography

A computed tomography scanner consists of an X-ray source and a detector placed opposite of each other, which rotate around the subject to capture several images from multiple angles. The images are then used to reconstruct a 3D image of the subject. Although computed tomography is relatively low cost and provides high spatial resolutions of around 0.3 mm, the scanner contains many moving parts. This type of moving design is not suitable for wearable devices, and the physical constraint puts a strict limitation on the temporal resolution (~66 ms) that makes it unsuitable for real-time cardiac imaging. Furthermore, the ionizing X-ray radiation makes it fundamentally unsafe for long-term wearing.

2.5 Emission Tomography

Single-photon emission computed tomography and positron emission tomography make use of radiotracers injected into the body that radioactively decay over time as they travel through the body following their designated molecular targets. These signals can then be collected using a gamma camera to quantify those molecular targets and metabolic events. This allows gathering unique types of information such as myocardial perfusion and cell metabolic activities. In addition, positron emission tomography's temporal resolution is too slow (>2000 ms) for cardiac imaging, while single-photon emission computed tomography's poor image resolution (~10 mm) makes it largely impractical for more general diagnostic imaging. There is also a very low signal-to-noise ratio in these modalities. Subjects are exposed to low levels of ionizing gamma radiation, and the tracers must be replenished over time as they decay, making these modalities unsuitable for wearable devices.

2.6 Optical Coherence Tomography

Optical coherence tomography uses light scattering within the 700-900 nm wavelength range, also known as the "therapeutic window", to image the human tissue. These wavelengths have low absorbance and high scattering in tissues on top of being non-ionizing, making them useful for imaging tissues. In constructing the image, the time delay cannot be used to determine the location of the scattered signals because the speed of light is too fast. Thus, interferometry is used instead, in which the primary beam of light is split in half to target the tissue and a mirror simultaneously. As the distance of the mirror is varied, constructive interference occurs with signals coming from different locations within the tissue, allowing the position of the signals to be distinguished. Due to the short optical wavelength, optical coherence tomography can achieve extremely high spatial resolutions of up to 1 μm, and temporal resolutions of 2 ms. In addition, dyes can be injected into the subject to add additional capabilities to optical coherence tomography.

For example, the use of voltage-reactive dyes can make it possible to form activation and conduction velocity vector maps of the myocardium using optical coherence tomography. Despite these advantages, optical coherence tomography is unsuitable due to the bulky optics required, and limited tissue penetration depth of 2-3 mm.

2.7 why Ultrasound should be Used

Lastly, we look at the rationale for selecting the ultrasound modality in this study. Piezoelectric transducers generate ultrasound waves throughout the tissue. The same transducers can then collect the backscattered signals and construct an image based on their strength and time delay at each pixel. This "all-in-one" capability of ultrasound allows the device to become extremely compact and easily scaled down to wearable form factors. Ultrasound waves have low absorption and backscattering and thus can penetrate over decimeters in the integumentary and musculoskeletal systems of the human body. Ultrasound has been able to achieve temporal resolutions of less than 1 ms. The spatial resolution of ultrasound increases with the frequency. However, this comes at the cost of penetration depth as higher frequencies are more strongly attenuated by the tissue. In general, most conventional diagnostic ultrasound devices use sound waves in the range of 2-18 MHz and can achieve spatial resolutions in the range of 0.4-2 mm. Additionally, even for long-term use, ultrasound has largely been considered fully safe as long as the power output is kept at the minimum levels needed, below the safety threshold defined by FDA ($I_{SPTA} \leq 720$ mW/cm$^2$, $I_{SPPA} \leq 190$) W/cm$^2$). The mechanical energy itself is not toxic to the body.

In the case of arrhythmia, a wearable device with live B-mode and M-mode images is perfect for several reasons. First, heart beats are directly recorded and visualized in echocardiography by the wearable device, resulting in a high accuracy in calculating heart rates from B-mode videos or M-mode images. Second, arrhythmia is very unpredictable and may only happen when heart is under high loads. The wearable device supports uninterrupted long-time monitoring in daily life and can capture any irregularity in heart beats. Third, the abnormal cardiac structure causing arrhythmia can be easily detected in B-mode images, which visualize the root cause of the disease and inform better therapeutic decisions. For example, the gross dilations of right atrium and right ventricle are considered as an important indicator of arrhythmia.

The main draw back of ultrasound is that there is inherently a lot of noise in the signal, due to random scatterers in the tissue. However, significant algorithmic progress has been made in this area to improve the image quality of modern ultrasound scanners. Especially given its versatile functions in clinical applications, ultrasound still remains extremely viable, as well as the best option as a wearable modality for imaging the heart.

As of the time of writing, there have been no other studies that have produced, specifically, wearable ultrasound heart imaging devices. A wearable device was made to target the heart, but did not have the imaging capability. Therefore, the wearable heart imaging capability introduced in this study addressed a critical unmet need.

3. Design and Fabrication of the Wearable Imager

In some embodiments, the transducer array is designed in an orthogonal geometry to achieve bi-plane imaging simultaneously. For the transducers, we chose the 1-3 composite for transmitting and receiving ultrasound waves because it possesses superior electromechanical coupling. In addition, the acoustic impedance of 1-3 composites is close to that of the skin, maximizing the acoustic energy propagating into human tissues. The backing layer dampens the ringing effect, broadens the bandwidth, and thus improves the spatial resolution. We used an automatic alignment strategy to fabricate the orthogonal array. The existing method of bonding the backing layer to the 1-3 composite was to first dice many small pieces of backing layer and 1-3 composite, and then bond each pair together one by one. A template was needed to align the small pieces. This method was very low efficiency. Now, we bond a large piece of backing layer with a large piece of 1-3 composite, and then dice them together into small elements with designed configurations. The diced array is automatically aligned on an adhesive tape with high uniformity and perfect alignment.

Electrodes based on eutectic gallium-indium liquid metal are fabricated to achieve better stretchability and higher fabrication resolution. Currently, eutectic gallium-indium alloys are patterned through approaches like stencil lithography, masked deposition, inkjet printing, microcontact printing, or microfluidic channeling. While these approaches are reliable, they either are limited in patterning resolution or require sophisticated photolithography or printing hardware. The sophisticated hardware not only presents a challenge in the development of compact, skin-conformal wearable electronics, but also makes fabrication complicated and time-consuming.

In some embodiments, we exploited a new technology for patterning. We first screen-printed a thin layer of liquid metal on a substrate. A key consideration before screen printing was how to get the liquid metal to wet the substrate. To solve this problem, we dispersed big liquid metal particles into small microparticles using a tip sonicator (FIG. 8). When microparticles contacted air, their outermost layer generated an oxide coating, which lowered the surface tension and prevented those microparticles from aggregating together. In addition, we employed 1.5 wt. % styrene-ethylene-butylene-styrene (SEBS) as a polymer matrix to dispense the liquid metal particles because SEBS could wet well on the liquid metal surface. We also used SEBS as the substrate. Therefore, the SEBS in the matrix and the substrate could merge and cure together after screen printing, allowing the liquid metal layer to adhere to the substrate efficiently and uniformly. Then we used laser ablation to selectively remove the liquid metal from the substrate to form patterned electrodes.

The large number of piezoelectric transducer elements in the array requires many such electrodes to address each element individually. We designed a four-layered top electrode and a common ground electrode. There are layers of SEBS between the liquid metal electrodes as insulation. To expose all electrode layers to connect to transducer elements, we used laser ablation to drill vertical interconnect accesses. Additionally, we created a stretchable shielding layer using liquid metal and grounded it through a vertical interconnect access, which effectively protected the device from external electromagnetic noises (fig. S8).

Before we attached the electrodes to the transducer array, we spin-coated toluene on the top of the multilayer electrode to soften the liquid metal-based elastomer, also known as "solvent-welding". The softened SEBS provided sufficient contact surface, which could help form a relatively strong Van der Waals force between the electrodes and the metal surface on the transducer array. After bonding the electrodes to the transducer array, we put the device at room temperature to let the toluene evaporate. The final bonding strength of more than 200 kPa is stronger than many commercial adhesives.

To encapsulate the device, we irrigated the device in a petri dish with uncured silicone elastomer (Ecoflex-0030, Smooth-On) to fill the gap between the top and bottom electrodes and the kerf among the transducer elements. We then cured the silicone elastomer in the oven for 10 minutes under 80° C. We lifted off the glass slide on the top electrode and directly covered the top electrode with a shielding layer. Then we lifted off the glass slide on the bottom electrode to release the entire device. Finally, screen-printing a ~50 μm layer of silicone adhesive on the surface completed the device fabrication.

4. Characterization of the Liquid Metal Electrode

Existing wearable ultrasound arrays can achieve excellent stretchability by geometrically designing thin metal films as electrodes. The serpentine geometry, however, severely limits the filling ratio of functional components, precluding the development of systems that require a high integration density or a small pitch. In this study, we chose to use liquid metal as the electrode due to its large intrinsic stretchability, which allows the electrode to be high density. The patterned liquid metal electrode had a minimum width of ~30 μm with a groove of ~24 μm (FIG. 9), an order of magnitude finer than other stretchable electrodes. The liquid metal electrode is ideal for connecting arrays with a small-pitch.

Figure 1B:
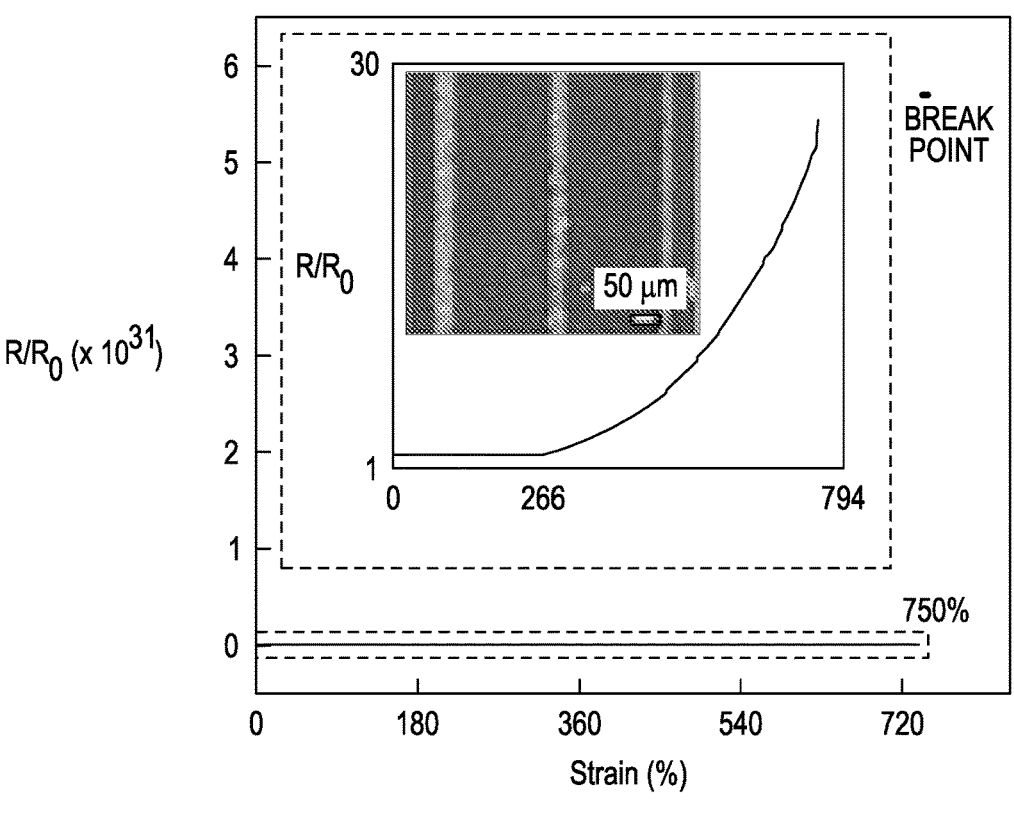
Figure 1C:
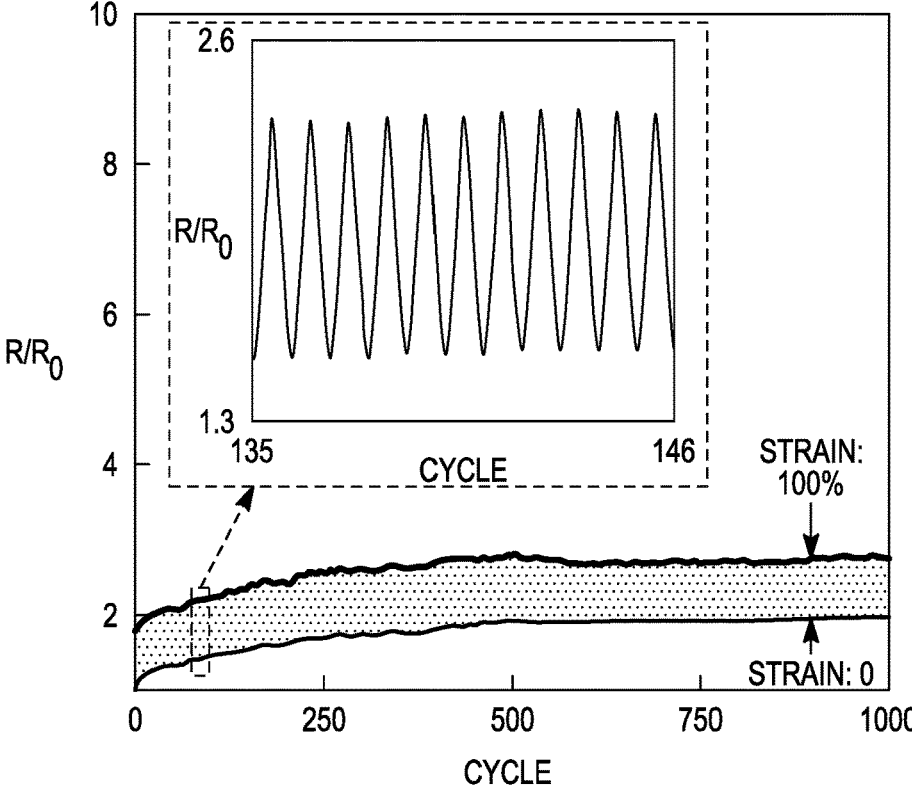
Figure 1D:
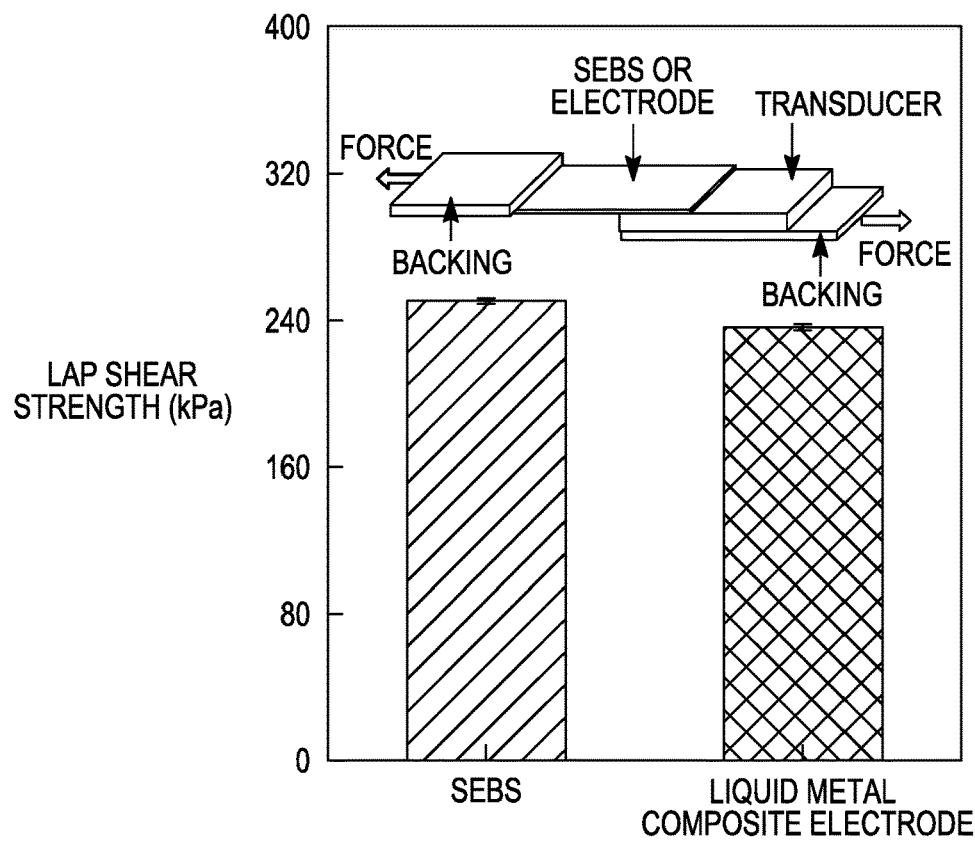
Figure 1E:
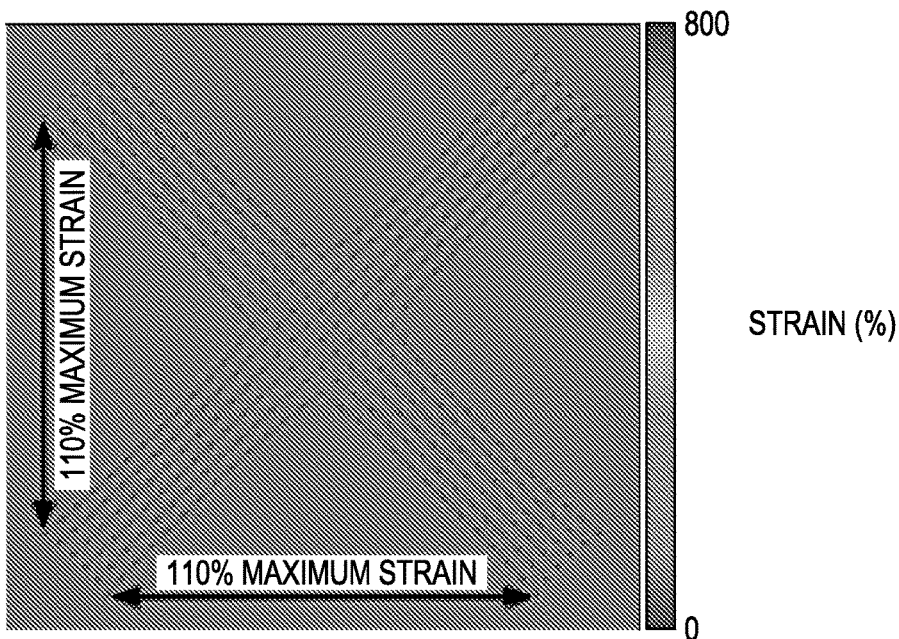
Figure 1F:
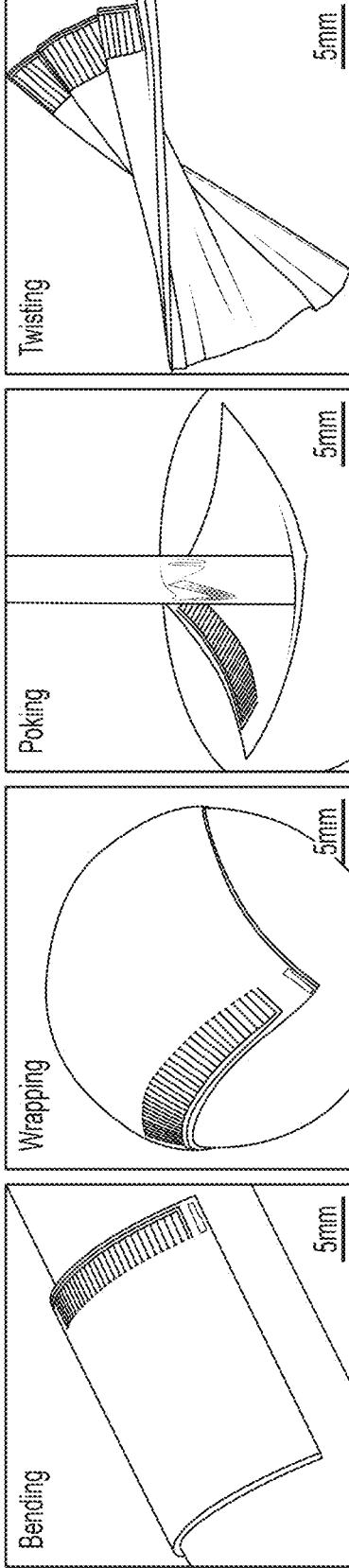

This liquid metal electrode exhibited high conductivity, exceptional stretchability, and negligible resistance change under tensile strain (FIGS. 1B and 1C; FIG. 10). The initial resistance at 0% strain was 1.74Ω (corresponding to a conductivity of ~11800 S/m), comparable to reported studies. The electrode could maintain a relatively constant resistance until stretched beyond ~266%. The resistance then gradually increased with strain until the electrode reached the ~750% failure strain (FIG. 1C, fig. S5). To investigate the electrode fatigue, we subjected them to 100% cyclic tensile strain (FIG. 1D). The initial 500 cycles observed gradual increase in the electrode resistance, because the liquid metal, when stretched, could expose more surfaces. These new surfaces were oxidized after contacting with air, leading to the resistance increase (fig. S5). After the initial 500 cycles, the liquid metal electrode exhibited stable piezoresistance, because after a period of cycling, there was not much new surfaces exposed.

5. Characterization of the Transducer Elements

Figure 7A:
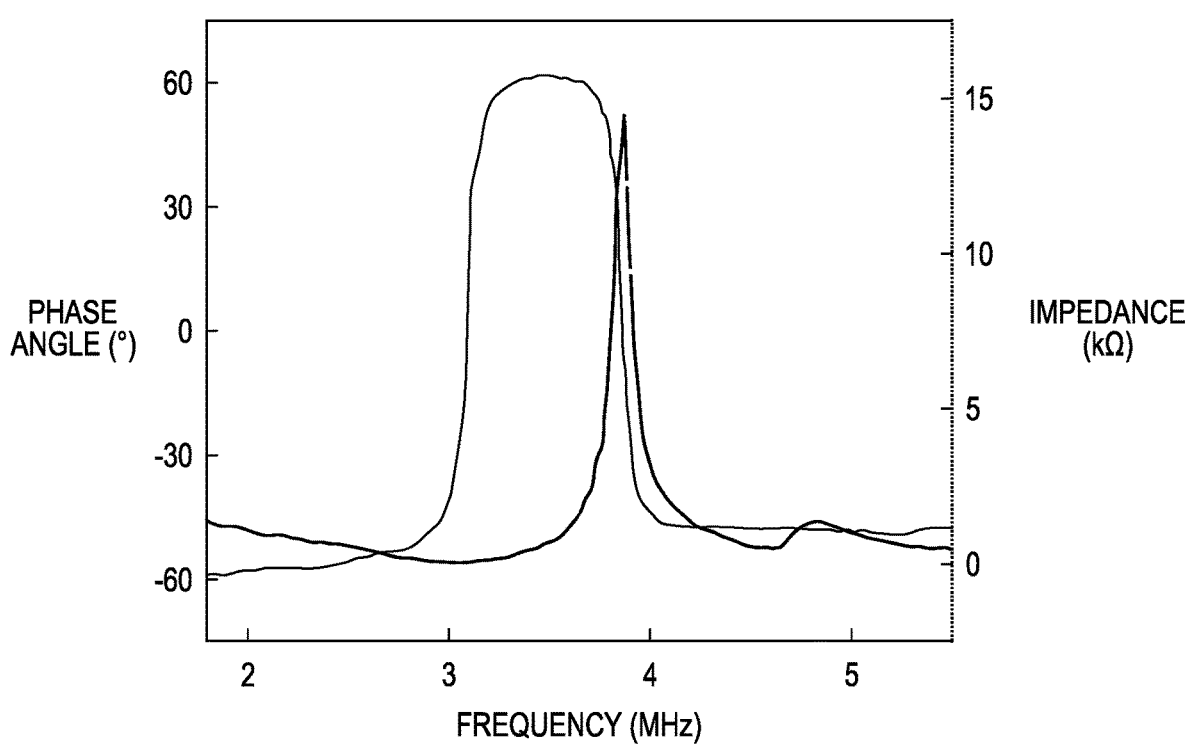
FIGS. 7(A)-7(D) present characterization data for the transducer array.
Figure 7B:
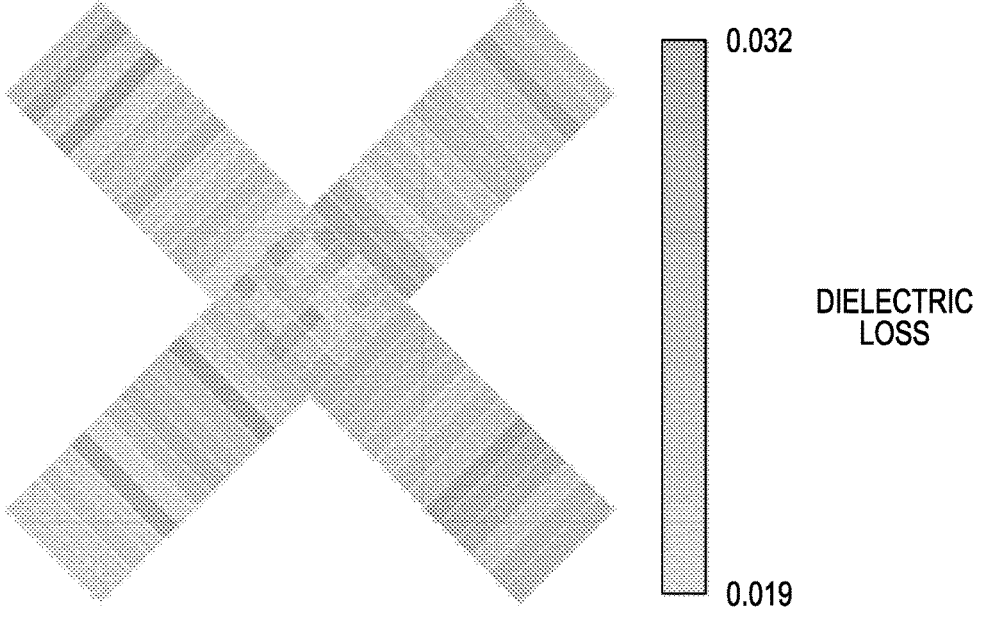
Figure 7C:
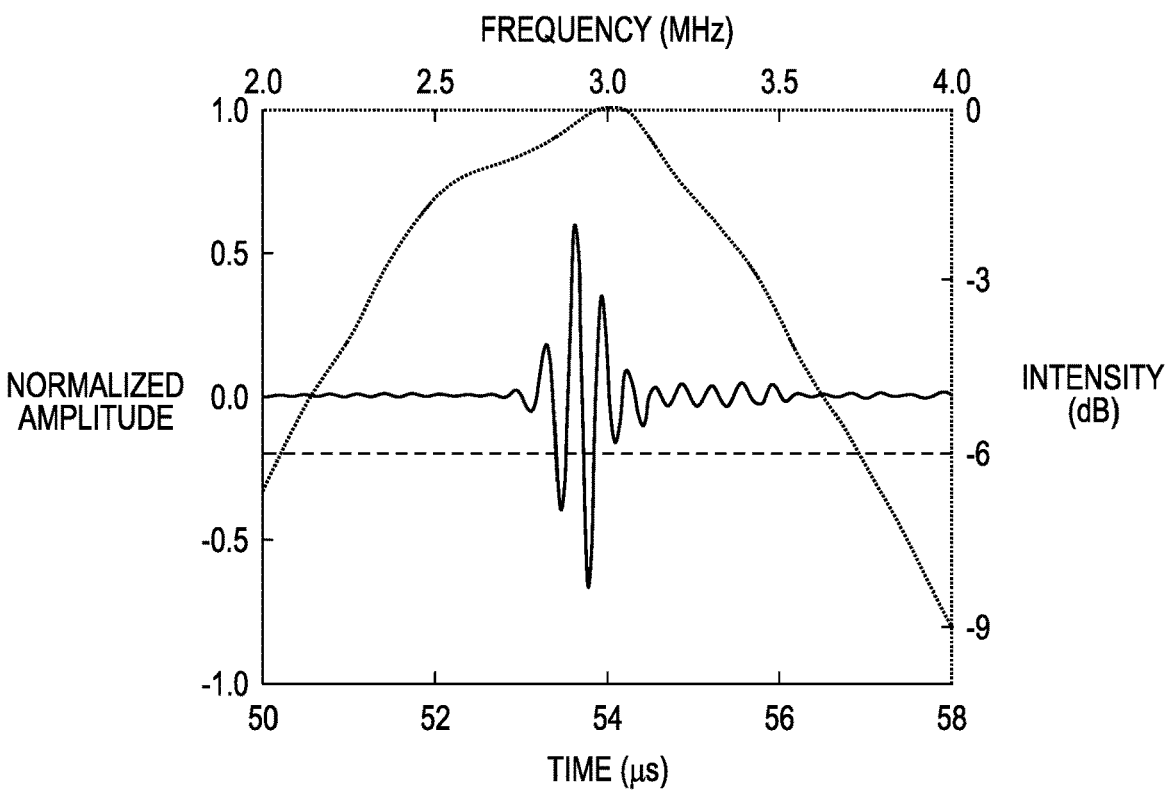
Figure 7D:
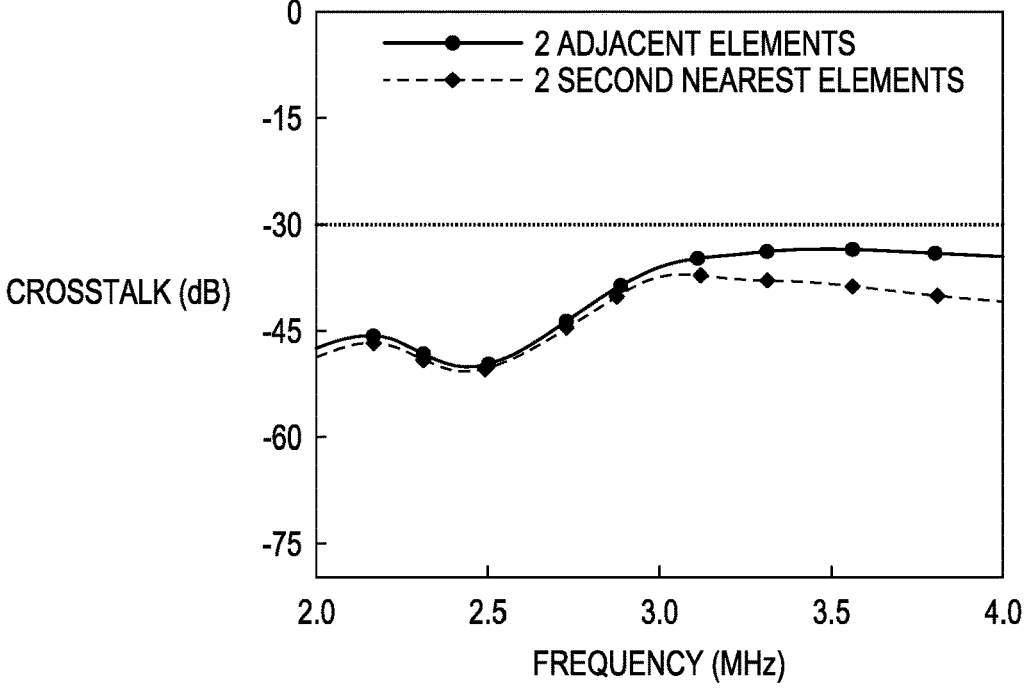

The electromechanical coupling coefficient of the transducer elements was calculated to be 0.67, on par with that of commercial probes (0.58-0.69). This superior performance was largely due to the technique for bonding transducer elements and electrodes at room-temperature in this study, which protected the piezoelectric material from heat-induced damage and depolarization. The phase angle was >60°, substantially larger than most earlier studies, indicating that the majority of dipoles in the element aligned well after bonding. The large phase angle also demonstrated the device's exceptional electromechanical coupling performance. Dielectric loss is critical for evaluating the bonding process because it represents the amount of energy consumed by the transducer element at the bonding interface. The averaged dielectric loss of the array was 0.026, on par with that of the reported (0.02-0.04 rigid ultrasound probes, indicating negligible energy consumed by this bonding approach (FIG. 7B). The response echo was characterized in time- and frequency-domains (FIG. 7C), from which the ~35 dB signal-to-noise ratio and ~55% bandwidth were derived. The crosstalk between a pair of adjacent elements and a pair of second nearest neighbors has been characterized (FIG.

7D). The average crosstalk was below the standard -30 dB in the field, indicating low mutual interference between elements.

6. Characterization of the Wearable Imager 6.1 General Setup

We characterized the wearable imager using a commercial multi-purpose phantom with many reflectors of different forms, layouts, and acoustic impedances at various locations (CIRS ATS 539, CIRS Inc.). The collected data are presented in table 2. For most of the metric tests, the device was first attached to the phantom surface and rotated to ensure the best imaging plane. Raw image data were saved to guarantee minimum information loss caused by the double-to-int8 conversion. Then, the raw image data were processed using the "scanConversion" function provided in the k-Wave toolbox to restore the sector-shaped imaging window (restored data). Five times upsampling were applied in the vertical and lateral directions. The upsampled data were finally converted to the dB unit using the following equation:

$$I_{new} = 20 \times \log_{10}(I_{old}) \qquad (4)$$

6.2 Penetration Depth

The penetration depth was tested with a group of lines of higher acoustic impedance than the surrounding background distributed at different depths in the phantom. The penetration depth is defined as the depth of the deepest line that is differentiable from the background (6 dB higher pixel value). As the deepest line at a depth of 16 cm available in this study was still recognizable from the background, the penetration depth was >16 cm.

6.3 Accuracy

The accuracy is defined as the precision of measured distance. The accuracy was tested with the vertical and lateral groups of line phantoms. The physical distance between the two nearest pixels in vertical and lateral directions was calculated as:

$$\Delta y = \frac{\text{imaging depth}}{N_{pixel,vertical} - 1} \qquad (5)$$

$$\Delta x = \frac{\text{imaging width}}{N_{pixel,lateral} - 1} \qquad (6)$$

We acquired the measured distance between two lines (displayed as two bright spots in the image) by counting the number of pixels between the two spots and multiplying them by $\Delta y$ or $\Delta x$ depending on the measurement direction. The measured distances at different depths were compared to the ground truth described in the datasheet. Then, the accuracy can be calculated by:

$$\text{Accuracy} = 1 - \left| \frac{\text{computed distance}}{\text{ground truth}} - 1 \right| \qquad (7)$$

The lateral accuracy was presented as the mean accuracy of the four neighboring pairs of lateral lines at the depth of 50 mm in the phantom.

6.4 Spatial Resolution

The spatial resolutions were tested using the lateral and vertical groups of wires. For the resolutions at different depths, the full width at half maximum of the point spread function in vertical and lateral directions for each wire were calculated. The vertical and lateral resolutions could then be derived by multiplying the number of pixels within the full width at half maximum by $\Delta y$ or $\Delta x$ depending on the measurement direction. The elevational resolutions were tested by rotating the imager to form a 45° angle between the aperture and the lines. Then, the bright spot in the B-mode images would reveal information of scatters out of the imaging plane. The same process as calculating the lateral resolutions was applied to obtain the elevational resolutions. The spatial resolutions at different imaging areas were also characterized with the lateral group of wires. Nine wires were located at +4 cm, +3 cm, +2 cm, +1 cm, and 0 cm from the center. The lateral and axial resolutions of the B-mode images from those wires were calculated with the same method.

Note that the lateral resolution worsens with the depth, mainly because of the receive beamforming (FIG. 20). There are two beamformed signals A and B. The lateral resolution of A point $(x_1)$ is obviously better than that of the B point $(x_2)$. The fact that lateral resolution becomes worse with the depth is inevitable in all ultrasound imaging, as long as receive beamforming is used.

As for different transmit beamforming methods, the wide-beam compounding is the best because it can achieve a synthetic focusing effect in the entire insonation area. The better the focusing effect, the higher the lateral resolution, which is why the lateral resolution of the wide-beam compounding is better than the other two transmit methods at the same depth. Additionally, the multiple-angle scan used in the wide-beam compounding can enhance the resolution at high-angle areas. The multiple-angle scan combines transmissions at different angles to achieve a global high signal-to-noise ratio, resulting in improved resolution.

The elevational resolution can only be characterized when the imaging target is directly beneath the transducer. For those targets that are far away from the center, they are difficult to be imaged, which makes their elevational resolutions impossible to calculate. When characterizing the elevational resolution, the device should rotate 45 degrees. In this case, most of the reflected ultrasound waves from those wires cannot return to the device due to the large incidence angles. Therefore, those wires cannot be captured in the B-mode images. One potential solution is to decrease the rotating angle of the device, which may help capture more wires distributed laterally in the B-mode image. However, a small rotating angle will cause the elevational image to merge with the lateral image, which increases the error of calculating the elevational resolution. Considering those reasons, we only characterized the elevational resolution with the imaging target directly beneath the transducer array.

6.5 Contrast Resolution

The contrast resolution, the minimum contrast that can be differentiated by the imaging system, was tested with gray scale objects. The collected B-mode images are shown in FIG. 2. Because the targets with +3 and -3 dB, lowest contrast available in this study, could still be recognized in the images, the contrast resolution of the wearable imager is <3 dB.

6.6 Dynamic Range

The dynamic range refers to the display range of the beamformed signals. Each pixel based on beamformed signals is given a gray scale value (0~255), which can be correlated to a range of contrasts. The contrast range is defined as the dynamic range. The dynamic range was tested with the gray scale objects. We captured B-mode images with the int8 data type. The mean pixel value in the selected area (FIG. 21) of each gray scale target was calculated first. The mean pixel values of different targets with contrasts ranging from −15 to +15 dB were plotted and extrapolated linearly to acquire the contrasts at pixel values of 0 and 255. Then, the dynamic range was obtained as:

$$\text{Dynamic range} = \text{contrast}_{255} - \text{contrast}_0 \tag{8}$$

6.7 Dead Zone

The dead zone is defined as the depth of the first line phantom that is not overwhelmed by the initial pulses. The dead zone was tested by imaging a specific set of wire phantoms with different depths right beneath the device and counting the line phantoms that are visible directly in the B-mode image.

6.8 Bandwidth

The bandwidth of the imager is defined as the ratio between the full width at half maximum in frequency spectrum and the center frequency. It was measured by a pulse-echo test. A glass was placed 4 cm away from the device and the reflection waveform was collected with a single transducer. The collected reflection waveform was converted to frequency spectrum by fast Fourier transform. The full width at half maximum was read from the frequency spectrum. We obtained the results using the equation:

$$BW = \frac{BW_{-6\,dB}}{\text{central frequency}} \tag{9}$$

6.9 Contrast Sensitivity

Contrast sensitivity represents the device's capability to differentiate objects with different brightness contrasts. The contrast sensitivity was tested with the gray scale objects. The contrast sensitivity is defined as the contrast-to-noise ratio (CNR) of the objects having certain contrast to the background in the B-mode image:

$$CNR = \frac{|\mu_{in} - \mu_{out}|}{\sqrt{\sigma_{in}^2 + \sigma_{out}^2}} \tag{10}$$

where $\mu_{in}$ and $\sigma_{in}$ are the mean and the standard deviation of pixel intensity within the object, and $\mu_{out}$ and $\sigma_{out}$ are the mean and the standard deviation of pixel intensity of the background.

6.10 Insertion Loss

The insertion loss is defined as the energy loss during the transmission and receiving. It was tested in water with a quartz crystal, a function generator with an output impedance of 50Ω, and an oscilloscope (Rigol DS1104). First, the transducer received an excitation in the form of a tone burst of a 3 MHz sine wave from the function generator. Then the same transducer received the echo from the quartz crystal. Given the 1.9 dB energy loss of the transmission into the quartz crystal and the 2.2×10⁻⁴ dB/mm MHz attenuation of water, the insertion loss could be calculated as:

$$Insertion\ loss = \left|20 \times \log_{10}\left(\frac{V_r}{V_t}\right) + 1.9 + 2.2 \times 10^{-4} \times 2d \times f_r^2\right| \tag{11}$$

7. Phase Correction on Nonplanar Surfaces

Figure 18:
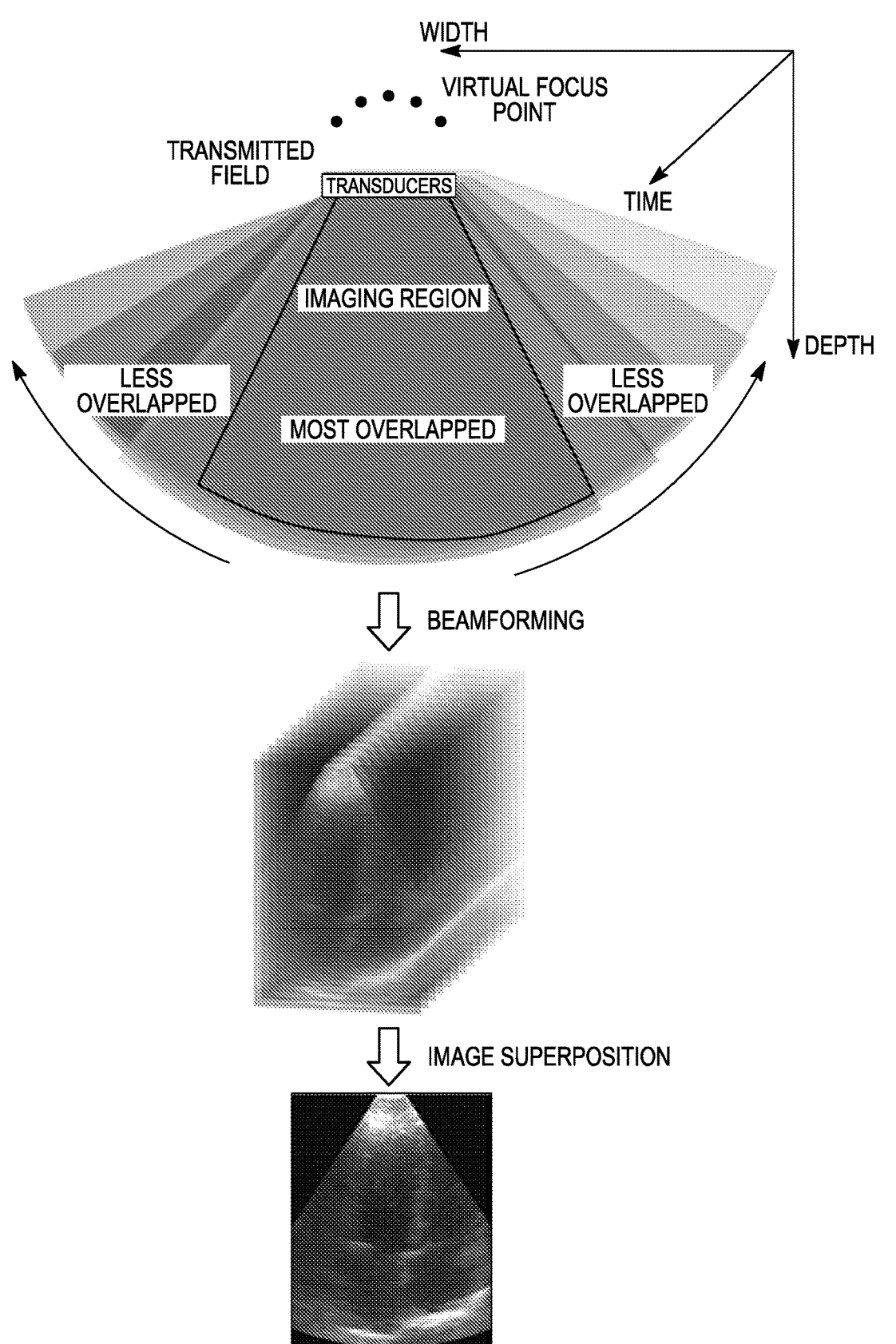
FIG. 18 illustrates the mechanism of wide-beam compounding B-mode imaging.

Because we used a wide beam compounding transmission in this study, the delay calculation for the aperture could vary a lot from traditional plane wave compounding transmission. As an intrinsic feature of wide beam transmission, the focal point of the aperture was set at the opposite side to the imaging area, with the distance between the focal point and the center of the aperture kept constant during the transmission (FIG. 18).

Assuming that a linear array of the wearable imager was attached to a planar surface, the way of calculating the transmission and time delay would not differ from the general approach. Considering the center of the linear array located at (0,0) by default, we can define the distance between the focal point and the center of the aperture as $df = \sqrt{x_{focal}^2 + z_{focal}^2}$, in which $z_{focal}<0$. Also, the location of the $i^{th}$ transducer could be defined as $(x_i, 0)$, where $x_i=(i-16.5)\times$ pitch because the device had 32 transducers in each imaging plane. Additionally, we defined the angle departure from the vertical direction as $\theta$, where $\theta>0$ when $x_{focal}>0$ and the aperture size A. For a given position of a pixel $(x_p, z_p)$, the time of the wavefront to go to the pixel since the earliest trigger on the transducers was:

$$t_{\theta,p}^e \approx \frac{\sqrt{(x_p - df \times \sin\theta)^2 + (z_p - df \times \cos\theta)^2} - dt}{c} \tag{12}$$

where $$dt = df \times \cos\theta$$

when $$|df \times \sin\theta| < \frac{A}{2}$$

and $$dt = \sqrt{\left(df \times \sin\theta - \text{sign}(\theta) \times \frac{A}{2}\right)^2 + (df \times \cos\theta)^2}$$

when $$|df \times \sin\theta| \geq \frac{A}{2}.$$

And the time for reflected wave to get back to the $i^{th}$ transducer was:

$$t_{i,p}^r = \frac{\sqrt{(z_p - z_i)^2 + (x_p - x_i)^2}}{c} \tag{13}$$

The total time delay since trigger should be $$t_{i,\theta,p}^{dt} = t_{\theta,p}^e + t_{i,p}^r \tag{14}$$

where the c was the sound speed that we assumed to be constant in the medium. Considering the delay differences among transducers, the delay of trigger of $i^{th}$ transducer was:

$$t_{i,\theta}^t \approx \frac{\sqrt{(df \times \sin\theta - x_i)^2 + (df \times \cos\theta - z_i)^2} - dt}{c} \tag{15}$$

As a result, the delay of the $i^{th}$ transducer for beamforming at a given pixel was:

$$t_{i,\theta,p}^{total} = t_{i,\theta,p}^{dt} - t_{i,\theta}^{t} \tag{16}$$

since each channel started to receive data after transmission.

When the device was placed on a nonplanar surface, the time delay formula above was no longer valid. Assume the curvature radius of the nonplanar surface was r. The previous location the $i^{th}$ transducer would then move to $(x'_i, z'_i)$, and $$x'_i = \text{sign}(x_i) \times r \times \sin \varphi \tag{17}$$

$$z'_i = r \cdot (1 - \cos \varphi) \tag{18}$$

where $$\varphi = \frac{x_i}{r}.$$

With the phase correction, time of the wavefront to go to the pixel since the earliest trigger on the transducers would be changed to $$t_{\theta,p}^{\prime e} \approx \frac{\sqrt{(x_p - df \times \sin \theta)^2 + (z_p - df \times \cos \theta)^2} - dt'}{c} \tag{19}$$

where $$dt' = \sqrt{df^2 + r^2 + 2 \times df \times r \times \cos \theta} - r$$

when $$|\varphi| < \frac{A}{2r}$$

and $$dt = \sqrt{df \times \sin \theta - \text{sign}(\varphi) \times |x'_1|)^2 + (df \times \cos \theta - s\text{sign}(\varphi) \times |z'_1|)^2}$$

when $$|\varphi| \geq \frac{A}{2r}.$$

Meanwhile, the time for reflected waves to get back to the $i^{th}$ transducer was changed to $$t_{i,p}^{\prime r} = \frac{\sqrt{(z_p - z'_i)^2 + (x_p - x'_i)^2}}{c} \tag{20}$$

and the delay of triggering the $i^{th}$ transducer was changed to $$t_{i,\theta}^{\prime t} \approx \frac{\sqrt{(df \times \sin \theta - x_i)^2 + (df \times \cos \theta - z_i)^2} - dt'}{c} \tag{21}$$

Finally, the delay of the $i^{th}$ transducer for beamforming at a given pixel after phase correction became:

$$t_{i,\theta,p}^{\prime total} = t_{\theta,p}^{\prime e} + t_{i,p}^{\prime r} - t_{i,\theta}^{\prime t} \tag{22}$$

In the receive beamforming, the value of each pixel could be computed as:

$$I_p = 20\log_{10} \sum\nolimits_{\theta=\theta_{min}}^{\theta=\theta_{max}} \sum\nolimits_{i=1}^{\# of channel} RF_i\left(t_{i,\theta,p}^{\prime total} \times f_s\right) \tag{23}$$

where $RF_i$ is the radio-frequency signal collected for the $i^{th}$ transducer and $f_s$ is the sampling frequency. Any value larger than 255 would be cut off to adapt to the 8-bit display.

8. Imaging Procedures
8.1 Positioning the Imager

Four standard positions/orientations were used to obtain the best B-mode images of the heart. The first position was on the left side of the sternum, between the second and fourth intercostal spaces. The device was pointing to the right shoulder. From this position, the imager could inspect the parasternal long-axis view of the left ventricle. By rotating the imager 90 degrees counterclockwise at the same position, with the device pointing to the left shoulder, a parasternal short axial view of the left ventricle could be obtained. The second position was between the fourth and fifth intercostal spaces. With the device pointing to the left shoulder, the four chambers of the heart could be observed from the apex in this view, also known as the apical four-chamber view. By rotating the device 90 degrees counterclockwise at the same position and aiming towards the right shoulder, the device revealed the left ventricle, left atrium, and mitral valve, i.e., apical two-chamber view.

8.2 Postprocessing the Data

After the transducer received the response echoes that carry the location and anatomic information of the heart, the echoes were demodulated, decimated, and compressed logarithmically to eventually generate the B-mode image. A graphical user interface for real-time phased array imaging was made up of display windows and control panels for customized settings (FIG. 40).

8.3 Interpretating the Four-View Images

In the apical four-chamber view, all four chambers could be seen simultaneously, so that ventricular interdependence and septal wall abnormalities between the chambers (e.g., in cor pulmonale) could be assessed. We could also measure left and right atria lengths and areas, as well as right ventricle diameter, length, and area.

Apical two-chamber view could be used to measure the left atrium length and area.

In the parasternal long axis view, detectable structures included the left atrium, left ventricle, mitral valve, aortic valve, interventricular septum, right ventricle, and left ventricular outflow tract. The unique orientation of this view allowed visualizing the full length of the mitral and aortic valve leaflets during their closure and excursion, which made it especially useful for evaluating valvular functions. Measurements taken in the parasternal long axis view included the interventricular septum end-diastole thickness, the left ventricular internal diameter end-diastole (LVIDd), left ventricular internal diameter end-systole (LVIDs), and left ventricular posterior wall dimensions. Among the measurements, the LVIDd and LVIDs were especially valuable because they were indirectly related to the left ventricular volume. By increasing the imaging depth, the pericardial and pleural spaces could also be seen from this view.

The parasternal short axis view was particularly useful for evaluating the left ventricular wall motion. In the short-axis plane, the circular cross-section of the left ventricle was captured (the basal, mid-cavity, and apical slices), and the contractility and distensibility were accessible as the motion of the walls was along the plane. The basal slice captures the ring with the largest diameter (segments 1-6). The mid-cavity slice captures a smaller diameter ring nested inside the basal view (segments 7-12). Likewise, the apical slice is nested inside the mid-cavity slice (segments 13-16). Segment 17 is the apex. Therefore, the relative changes in the cross-sectional diameter, along with the uniformity of wall motions, could be easily assessed. Using these assessments, we can identify the specific segment of the left ventricular wall as pathological.

8.4 Tracking Myocardium Displacement

To quantitatively evaluate the segment displacement, we set a target area for each segment to facilitate further processing. We blurred the original images in the area to reduce the impact of speckles on the feature refinement, and then computed the edge information using a Canny operator based on the blurred image. By indexing the edge in the binary map, the myocardium displacement could be recorded. With these measurements, we could monitor the potential risk factors for myocardial infarction or akinesia, precisely localize ischemic heart diseases, and easily assign hypokinetic or akinetic regions of the left ventricular wall to their governing coronary arteries by tracking the relevant myocardium_displacement.

9. Validation for Long-Term Use

Motion artifacts plague ultrasound imaging. To verify the performance of the wearable imager under daily circumstances, we attached the device to subject's chest and tested the imaging quality under different postures. In the experiments, there was no obvious deterioration of imaging quality, due to the intimate contact of the device to human skin (FIG. 26), attesting the stable performance of the device.

Figure 27:
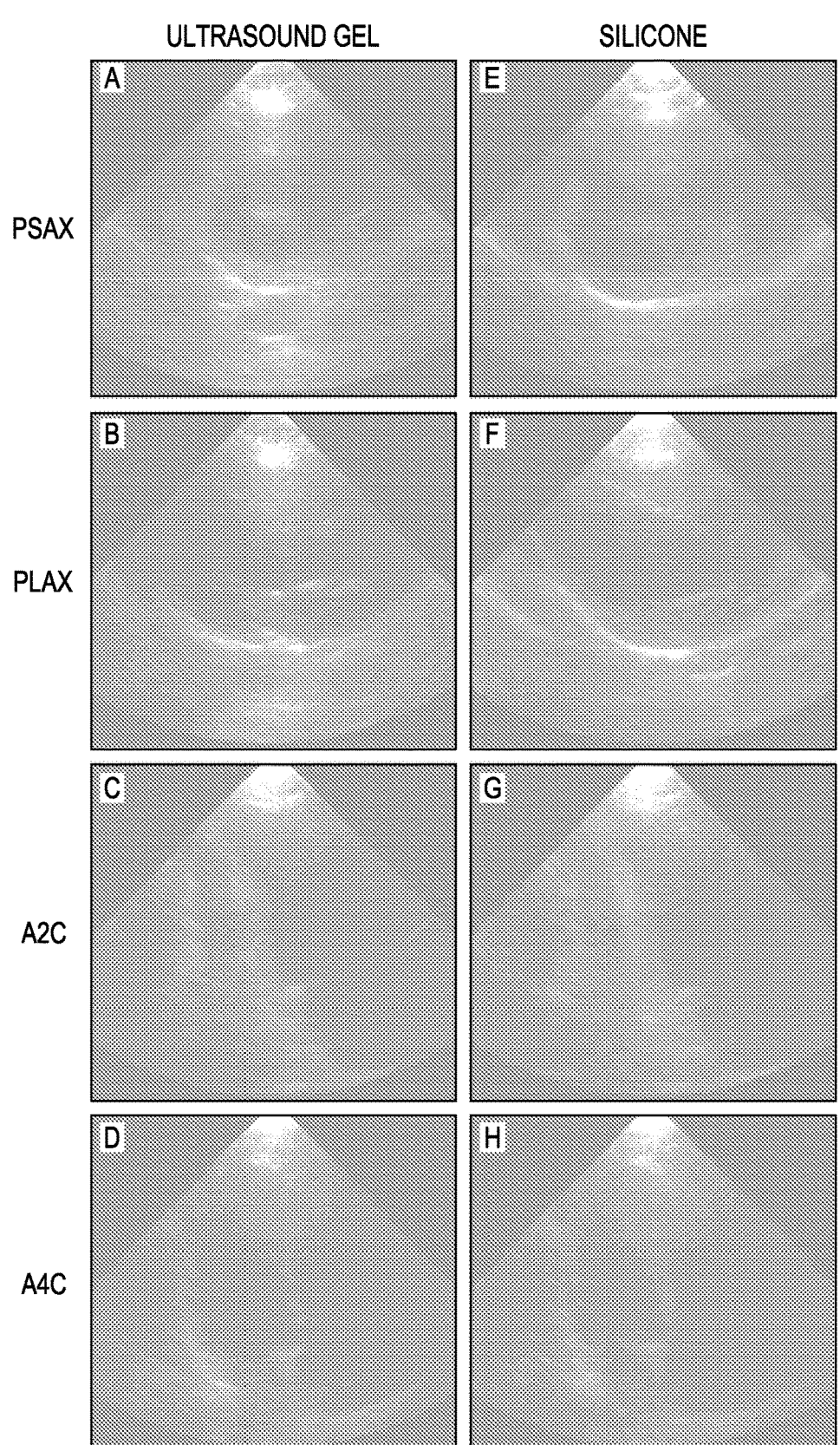
FIGS. 27(A)-27(H) show B-mode images collected with different couplants.

We compared the imaging results along the four standard views with ultrasound gel and silicone as the couplant (FIG. 27). The results showed that the contrast between different structures and details in the heart anatomy were well conserved when the couplant was changed from ultrasound gel to silicone. We repeated the tests on ten subjects and obtained reliable and reproducible results (FIG. 30).

In addition, the biocompatibility of the device was also a potential concern for long-term use, which may adversely irritate the skin. We attached the device to subject's chest with a commercial adhesive (e.g., Tegaderm) for 24 hours (FIG. 28), during which the skin experienced all kinds of scenarios, including exercising and showering. After removing the device, no allergy was observed. The major issue was the reddish area around the device attachment location caused by peeling off the Tegaderm adhesive.

10. Simultaneous Measurements of M-Mode Images and Electrocardiogram

At the beginning of the test, the wearable imager was attached to the parasternal site to image along the parasternal short axis view. We triggered the recording of B-mode images and electrocardiogram simultaneously. With the concurrent ending of the recording, the time (i.e., frame number in this case) of B-mode images and electrocardiogram could be aligned. Furthermore, we plotted the M-mode image by selecting pixels in one line in B-mode images and correlating this array of pixels to the frame number.

11. Stress Echocardiography 11.1 Significance

Under a steady state of a healthy subject, the left ventricular volume changes consistently, so the stroke volumes, cardiac outputs, and ejection fractions (three of the most significant indicators of cardiac functions) do not vary significantly. However, the heart state may change frequently and could be extremely intricate at times. Abnormal fluctuations exist in estimating the cardiac function of patients with heart diseases, and the symptoms could be very unpredictable, which also incur dramatic changes in the heart in a relatively short time. Symptoms of cardiovascular diseases like myocardial ischemia only emerges under stress, where the induced wall motion abnormalities are more noticeable. Therefore, stress echocardiography is carried out. Valvular pathologies are easily observed by individually tailored stress echocardiography. In addition, stress echocardiography is valuable for studying pulmonary circulation. Stress echocardiography can also help determine limits for safe exercise before starting a cardiac rehabilitation program or recovering from a cardiac event, and sometimes help evaluate the cardiac status before heart surgery.

11.2 Limitations of Existing Procedures

The process of stress echocardiography sometimes suffers from the inter-observer variabilities. Current evaluation approach requires manually tracing the contour of the left ventricle in the echocardiographic images and calculating its end-systolic and end-diastolic volumes for further analysis. Assessments are carried out typically based on only one cycle of heartbeat, even if the standard guidelines recommend tracking and averaging five cycles before making a conclusion. It potentially brings huge variance and uncertain accuracy to diagnostic results, especially for those less-trained medical assistants in low-resource regions.

Stress echocardiography also requires extremely sophisticated procedures to find an appropriate imaging location/orientation in a short time. The acquired views must be of the same regions of myocardium before and after exercise. Same regions in the ultrasonographic window are required to make sure the images are from the same or a very similar location/orientation of the heart. Otherwise, the measurements will be incorrect, because the chamber volume varies in images from different locations/orientations. In addition, the end-point determining when the patient should stop exercising is depending on whether patients achieve the target heart rate, experience moderate angina/severe chest pain, or reaches tolerable exercise limits. These subjective criteria may result in suboptimal cardiac testing outcomes. Furthermore, patients may be vulnerable to certain diseases that show up only during exercise, which is not monitored by existing procedures. For example, myocardial ischemia does not show in the resting state but appears only in stress, resulting in hypokinesia, akinesia, and dyskinesia. These symptoms are usually mild but can develop to be acute and lethal if neglected. However, because the patient is not monitored during exercise, the initiation of myocardial ischemia is unknown, not only missing valuable data but also leaving the patient at risk.

11.3 Echocardiography by the Wearable Imager

Those limitations of existing echocardiography can potentially be addressed with the wearable imager demonstrated in this study. In the parasternal long axis view; the wearable imager was attached to the chest of the subject continuously during the entire process. The heart rate was estimated to be average 70 beats per minute for the rest stage, which changes occasionally though, but still within a normal range. Then, the subject exercised on a cycling bike while the device continuously monitored the heart status. As the exercise began, the heart rate gradually rose. The subject exercised as hard as possible to reach the possible highest heart rate. The whole exercise duration took around 12 mins. After exercise, the heart rate slowed down back to normal.

The LVIDs and LVIDd were measured during different stages. Before exercise, the average LVIDd and LVIDs were 45 mm and 27 mm, respectively. During exercise, growing need of blood supply accelerated the heart beats, but the LVIDd and LVIDs were slightly dropping because a shorter pumping period allowed less muscle extensions. At the peak of exercise, LVIDd roughly dropped to 38 mm and LVIDs went down to 22 mm. After exercise, the LVIDd and LVIDs recovered to approximately 41 mm and 24 mm. respectively. Fractional shortenings, the reduction of end-diastolic diameter during systole, is a measure of the cardiac muscular contractility. It was calculated as the difference between the LVIDd and LVIDs divided by the LVIDd.

The parasternal long axis view contains information mostly about left ventricle and atrium, while the apical four-chamber view provides a more comprehensive window of all four chambers and is more precise for estimating the left ventricular volume. Because the apical four-chamber view requires the patient to be tilted in the left lateral decubitus position so ultrasound can enter from the apex, we could not collect these data during exercise. In the apical four-chamber view, we could see that both end systolic volume and end diastolic volume were increasing after exercise. This process of heart restoration is sometimes defined as heart volume reversal. Reasonably, exercise leads to increases in both contractility and afterload of chambers, resulting in a physiological decrease in chamber volumes immediately.

Changes in ventricular size under stress may provide useful information regarding cardiac functions. For example, the end systolic volume reversal may provide complementary information for risk stratification of cardiac diseases. A decreasing end diastolic volume may be a critical indicator of hypovolemia resulting from poor oral intake, emesis, or myocardial loss during cancer treatment. An unsteady end systolic volume recovery also portends the possibility of diseases like septal defects or valvular regurgitation.

12. Developing the Deep Learning Model 12.1 Surveying Different Models

We surveyed different deep learning models in the literature and made the selection based on their popularity and relevance to this study. Current widely-adopted image segmentation deep learning models can be classified into two categories: U-Net models, which are known for fast and precise biomedical image segmentation with multiple variants, and Fully Convolutional Networks (FCN) models, an end-to-end deep learning method, which first uses a series of fully connected convolutional layers to find useful features from the input image and then use an upsampling layer to restore the output image size to the same as the input image size.

Specifically, U-Net models are based on the well-established U-Net architecture for fast and precise biomedical image segmentation. U-Net architecture has gained wide adoption. Many researchers have proposed variant models based on the U-Net architecture. In this study, in addition to the original U-Net model, we also worked with its variants, including Attention-U-Net (U-Net model with an attention gate), U-Net++ (U-Net with redesigned skip pathways, dense skip connections, and deep supervision), NAS-UNet (Neural Architecture search with a U-Net architecture), U-Net+ResNet50 (U-Net with ResNet encoders), and U-Net mini (A simplified structure of the original u-net).

The FCN model is widely used for semantic segmentation. FCN gained wide adoption for its outstanding performance and no restriction on the input image size. Specifically, an FCN model first uses a series of fully connected convolutional layers to find useful features from the input image and then uses an upsampling (backwards strided convolution) layer to restore the output image size to the same as the input image size. If we return the output directly after solely using the upsampling layer, we call the network FCN-32 based on the number of upsampling operations. It is believed that spatial location information can be lost when going deep in the neural network. One solution for this is to fuse the predictions of multiple stages of the convolution layers. FCN-8, for example, fuses the predictions of the final three layers, and therefore only needs to upsample for eight times.

12.2 Training Data Overview

To ensure accuracy of the pre-processing of input images, we performed frame-level segmentation/labelling of the left ventricle under the guidance of a cardiologist, and followed the Modified Simpson's rule for volume calculation. These data are used as the training dataset, as summarized below.

| | Commercial imager on static subjects | Wearable imager on static subjects | Wearable imager on moving subjects |
|---|---|---|---|
| # of labeled data | 221 | 201 | 2029 |
| # of unlabeled data | 279 | 299 | 3829 |

12.3 Data Augmentation

We used data augmentation techniques to expand the limited labelled dataset. We applied rotation, scaling, and gaussian noise to the data to augment the dataset. Specifically, we generated four additional images for each of the labelled images by rotating the original data clockwise/counterclockwise by 5 degrees, rescaling it by a factor of 1.2, and applying gaussian noise to it. The results indicate that the data augmentation slightly improved the performance of the deep learning model (FIG. 35).

12.4 Evaluating Model Performance

We evaluated the models' performance quantitatively using Mean-Intersection-Over-Union (mIoU), which is one of the most widely used evaluation metrics for benchmarking object detection (107). Specifically, intersection-over-union (IoU) is used to compare the similarity between two shapes (107) and is calculated using:

$$IoU = \frac{\text{Area of intersection}}{\text{Area of union}} \qquad (24)$$

The mIoU is then calculated by taking the mean of IoU for all images in a dataset. In this study, we calculated mIoU by taking the mean of IoU of each pair of the predicted image segmentations by the deep learning models and the manually labelled image segmentations. Specifically, for each "(predicted-image, labelled-image)" pair, its IoU equals to the number of pixels within the left ventricle in both images divided by the total number of unique pixels within the left ventricle by either of the two images. The evaluation results for different models are listed in FIG. 34.

12.5 Image Imputation

During exercise, small amounts of the recorded B-mode images ween the heart was blocked by the deep-breathing lung. To solve this problem, we applied an imputation algorithm to complement the missing parts in these corrupted images to generate a continuous waveform (FIG. 37).

13. Detailed Left Ventricle Working Processes

A new cardiac cycle starts from the end of left ventricular relaxation in the last cycle. When the pressure in the left ventricle drops below that in the left atrium, the pressure difference pushes the mitral valve to open, so blood flows from the left atrium to the left ventricle. The inflow of blood triggers the first volume increment of the left ventricle, which is called rapid inflow. The blood inflow builds up the pressure in the left ventricle and at the same time releases the pressure in the left atrium. As the pressure difference decreases and the inflow rate slows down, the volume of the left ventricle hits the first equilibrium, and the mitral valve tends to close. This period is the interval between passive blood flow and active blood flow caused by atrium contraction, which is named diastasis. Afterwards, the left atrium starts to contract to build the second pressure difference. The pressure difference again enforces the mitral valve to open and causes the second stage of blood inflow to the left ventricle. Simply, the process of this pressure generation is called atrial systole or atrial contraction. At the end of this process, the volume of the left ventricle reaches its peak as the second equilibrium.

Then, the left ventricle starts to contract to raise the pressure inside. Because the mitral valve and aortic valve keep closed during the contraction, the volume of left ventricle holds. Therefore, this contraction is called isovolumetric contraction. The mitral valve is a one-way valve, so there is no blood countercurrent back into the left atrium and only the aortic valve opens after the isovolumetric contraction. The blood in the left ventricle is then ejected into the aorta, which is called rapid ejection. The rapid ejection results in an obvious drop in the left ventricular volume and pressure so there is a sharp slope in the curve. Like the rapid inflow, as the pressure difference between the aorta and left ventricle vanishes, the aortic valve closes. Following the ejection, a small portion of blood in left ventricle remains. Because the aortic valve is also a one-way valve to keep the unidirectional blood flow, the left ventricular volume keeps stable during relaxation, which is also named isovolumetric relaxation. At the end of the isovolumetric relaxation, next cardiac cycle commences.

The precise monitoring of the cardiac events can provide more insights into pathologies of cardiac dysfunctions. For example, the ejection rate based on the volume curve can reveal the myocardium contractility and stenosis of aortic valves.

14. Continuous Cardiac Performance Monitoring 14.1 Monitoring Ejection Fraction, Cardiac Output, and Stroke Volume Simultaneously Commonly monitored vital signs contain body temperature, respiration rate, peripheral blood pressure, and heart rate. The first three parameters cannot directly reflect the heart status, while the heart rate only tells how quickly the heart is pumping but does not reveal the actual performance of the heart. Other parameters, like ejection fraction, cardiac output, and stroke volume should be explored for a more comprehensive and conclusive diagnosis.

Ejection fraction represents the fraction of the blood ejected from the left ventricle per cycle. It is an indicator of the left ventricle's overall systolic performance (Equation 3). Cardiovascular diseases lurk in an abnormal fluctuation of ejection fraction. Normal left ventricular ejection fraction should be ≥50%, and a reduced one may manifest itself as heart failure: a moderately reduced ejection fraction is within 40-49%, and a reduced one is <40%. Chronically attenuated ejection fraction is undoubtedly a danger sign, and an unreasonably high ejection fraction also entails troubles like hypertrophic cardiomyopathy, a common cause of sudden cardiac arrest. As one of the most clinically significant indices of cardiac function, ejection fraction is key in differentiating systolic versus diastolic heart failure, and is well correlated with mortality in stable outpatients with coronary artery disease and heart failure.

Cardiac output is a volumetric blood flow rate and is an indicator of the tissue oxygenation (Equation 2). The cardiac output, logically the product of the heart rate and the stroke volume, the blood volume pumped from the left ventricle every minute, can aid in the diagnosis of heart failure conditions, monitor patient status during surgeries and intensive care, and evaluate the overall cardiac functions. The cardiac output is widely monitored in anesthesiology and emergency care. Measurement of cardiac output is specifically essential in unstable patients whose condition may undergo dramatic changes in a short time, as it indicates an overall systemic oxygen delivery and tissue perfusion. Many pathologies besides cardiovascular diseases lead to changes in cardiac output. Abnormally decreased cardiac output could be a sign of heart failure caused by valvular heart diseases, but also could be intoxications like acute azotemia, indicating a severe dysfunction of kidney. Aberrant high cardiac output may be a complication of sepsis, hyperthyroidism, or anemia. When evaluating the cardiac output, oftentimes a patient may appear asymptomatic during resting conditions due to a wide range of physiological regulatory processes such as vasodilation and minor increases of heart rate within the physiological range. Therefore, maximal cardiac output measurements during exercise are also of particular interest for their ability to reveal underlying problems in otherwise normally asymptomatic subjects.

Stroke volume is the difference between the end diastolic volume (EDV) and the end systolic volume (ESV), representing the absolute blood volume ejected from the left ventricle in a single cycle. Stroke volume, when used together with cardiac output and/or ejection fraction, can provide a much more comprehensive overview of the cardiac status. For example, as mentioned above, cardiac output can often appear asymptomatic. In those cases, the presence of a lowered stroke volume may reveal underlying heart failure. In other cases, a patient might appear asymptomatic if only considering the ejection fraction. Then, the presence of a decreased stroke volume would be able to indicate diastolic heart failure.

There are several other examples demonstrating why monitoring any one of these parameters in isolation may lead to inaccurate diagnosis results. For example, ejection fraction may overstate cardiac functions in left ventricular hypertrophy, which can lead to heart failure. In this case, ejection fraction remains normal, but stroke volume and cardiac output are dropping, which is also well known as heart failure with preserved ejection fraction. Diagnosis only based on ejection fraction would be wrong, while comprehensive analysis on ejection fraction combined with cardiac output and stroke volume can generate correct results. Conversely, diastolic and systolic dysfunctions of the left chambers sharply reduce ejection fraction, but the cardiac output can maintain in the normal range with compensation of increased heart rate. Besides cardiac diseases, some surgical procedures may also have impacts on cardiac functions that require monitoring these three indices simultaneously.

This scenario is also paralleled in the measurement of blood pressure, which is commonly done in current practice. Blood pressure reflects a composition of multiple contributing factors, for example cardiac pre-load and vascular resistance. Much like the scenarios presented by stroke volume, ejection fraction, and cardiac output, a normal blood pressure reading could obscure underlying abnormalities in the cardiac pre-load, and vascular resistance if measured in isolation. Measurement of the left ventricular volume can serve as an indicator for these factors contributing to blood pressure. The cardiac pre-load is how much the myocardium is stretched prior to contraction, and is reflected in the EDV. Vascular resistance can be estimated from cardiac output using lumped parameter models of the circulatory system. The ability to monitor the volume of the left ventricle can thus provide insight into the contributing factors to blood pressure and reveal diseases that might otherwise be obscured Therefore, ejection fraction, cardiac output, and stroke volume are important parameters for evaluating cardiac performance, and together provide comprehensive analysis of the blood delivery capabilities of the heart. Continuously monitoring these indices of the heart for long-term is of strong prognostic values and has great potential to decrease the mortality and morbidity of many cardiovascular diseases and conditions.

14.2 Monitoring the Left Ventricular Volume by 3D Imaging

From Equations 1 to 3, the ejection fraction, cardiac output, and stroke volume are directly related to the volume of the left ventricle (EDV and ESV). Thus, the most direct method to measure these indices would be to monitor the left ventricular volume. Ideally, the most accurate and direct approach would be to capture 3D images of the left ventricular chamber throughout the cardiac cycle and use those 3D images to calculate the volume. Common methods of capturing these 3D images include traditional ultrasound, computed tomography, radionuclide imaging, and magnetic resonance imaging. However, these common cardiac imaging techniques have a host of limitations, including device bulkiness, low temporal resolutions, and long-term toxicity to the body. Furthermore, in many cases, it is desirable to continuously monitor cardiac output in the operating theater to prevent complications during surgery such as shock, which is not viable for the aforementioned techniques given these drawbacks.

In addition, the calculation based on manual image labelling suffers from interobserver variability. Specifically, when labelling the left ventricular dimensions, the endocardial border requires to be traced continuously from one side of the mitral annulus to the other side. However, because the endocardial is hypoechoic, no sharp boundary can be easily seen in the image, yielding large discrepancies of left ventricular dimensions between clinicians' observations. The discrepancies can be further magnified in calculating stroke volume, cardiac output, and ejection fraction, which results in an inaccurate diagnosis and introduces uncertainties in subsequent treatment regimens. In addition, less severe abnormality suffers from greater interobserver variability, where early symptoms will easily slip away if not well measured by two or more experienced echocardiographers.

14.3 Monitoring the Left Ventricular Volume by 2D Imaging

The next most direct method of obtaining the left ventricular volume would be to approximate the 3D volume of the left ventricle through 2D imaging. This approach faces similar problems due to the use of imaging but is computationally faster and can achieve higher temporal resolutions than 3D imaging.

While 2D imaging with ultrasound is a widely used approach for its convenience, traditional ultrasound has a bulky housing and requires the probe to be manually held in place. Point-of-care ultrasound probes transcend the limitations of traditional medical imaging and promotes precision medicine for household use, but they still require an external force to maintain a stable coupling with the skin. Otherwise, the image window will change and generate unfair comparison which results in misdiagnoses. In addition, their use highly depends on the clinicians' experience, which is prone to generating inter-observer variabilities and operational errors. Robotic arms have been applied in such a case, but the higher cost and the even more bulky design are the new problems, making it inaccessible in most cases and impractical for continuous and long-term measurements.

14.4 Monitoring the Left Ventricular Volume by Model Estimations

Therefore, the traditional approaches to continuously monitoring stroke volume, cardiac output, and ejection fraction do not tend to employ imaging, but instead use models to estimate these parameters from other indirect measurements. Here, we provide a review of some of the major relevant non-imaging methods.

(a) Fick's Method

According to the Fick principle, the ratio between the rate at which oxygen is absorbed into the blood and the rate at which blood is delivered through the body, is directly represented by the difference in blood oxygen content between mixed venous blood and arterial blood. This principle is summarized by:

$$CO = \frac{VO_2}{C_a - C_v} \tag{25}$$

where CO is cardiac output, $VO_2$ is the amount of pure gaseous oxygen consumed per unit time, and $C_a$ and $C_v$ are oxygen content of arterial and mixed venous blood, respectively. Typically, $VO_2$ is measured using a spirometer, while $C_a$ and $C_v$ require catheters to be inserted into the patient. $C_v$ is measured from the pulmonary artery or vena cava, while $C_a$ is often measured from the brachial or femoral artery.

While Fick's method can be highly accurate, in the range of 5 to 10%, and is often used as a benchmark for other methods, it is highly invasive and requires catheterization. Furthermore, to take accurate readings, the patient's cardiac output and oxygen consumption must be stable for several minutes at a time. It is also inconvenient for infants, or during surgery, because a sufficient blood volume is required for this technique.

(b) Indicator Dilution Techniques

Indicator dilution is a variation of the Fick principle and works in a similar way. Rather than using oxygen as an indicator, other indicators can be injected into the blood stream at a single point, and their concentration is analyzed downstream. The most common indicators used in dilution are indocyanine green dye (dye dilution), or cold saline (thermodilution).

In the case of dye dilution, the dye concentration is measured using a densitometer, based on the optical density of the blood. This is then plotted over time, and the area under the curve can be related to the cardiac output and the amount of dye initially injected using the Stewart-Hamilton equation:

$$CO = \frac{V_{indicator}}{\int_0^\infty C(t)dt} \tag{26}$$

where the numerator is the initial amount of indicator injected, and C(t) is the concentration of the indicator measured downstream over time.

In reality, because the dye is not removed from the bloodstream by the kidneys sufficiently fast, the concentration curve peaks multiple times as the dye recirculates (113). Therefore, the curve must be extrapolated so that it returns to zero concentration.

For thermodilution, the Stewart-Hamilton equation is modified to account for the heat transfer between blood and saline:

$$CO = \frac{K * V_{indicator} * (T_{blood} - T_{indicator})}{\int_0^\infty T_{measured}(t)dt} \qquad (27)$$

$$K = \frac{c_{indicator} \rho_{indicator}}{c_{blood} \rho_{blood}} \qquad (28)$$

where c is the specific heat, $\rho$ is the density, $V_{indicator}$ is the volume of indicator initially injected, $T_{blood}$ and $T_{indicator}$ are the initial temperatures of the blood and indicator, respectively, and $T_{measured}(t)$ is the temperature measured downstream over time.

The injected saline lowers the temperature of the blood as it travels through the bloodstream, followed by warming as it is mixed and diluted in the blood. This is measured using a thermistor.

Indicator dilution is unsuitable for continuous monitoring as the temporal resolution is too low. One must wait for roughly 1 minute for the indicator to circulate and fully dilute. In addition, the densitometer requires a lengthy calibration process. Unlike the Fick method, there is no self-sustaining constant flux of indicator, so periodic reinjection is required. Over time, this can increase the risk of embolism, infection, and fluid imbalances.

These methods can also be error-prone. For example, thermodilution techniques will have limited accuracy given unstable body temperature, but this may be uncontrollable in certain cases, like liver transplantation surgery. In addition, arterial pulse waves could also be transferred to cardiac measurements, but this is also unreliable for monitoring on trends because it cannot compensate for circulatory changes. Also, the Stewart-Hamilton model itself assumes ideal fluid flow. Many of the assumptions of ideal fluid flow are violated by the human circulatory system, such as single inflow and single outflow tracts, complete mixing of the fluids, steady flow, and no recirculation of indicator.

Additionally, in dye dilution, the downslope of the concentration curve must be extrapolated extensively due to recirculation of the dye, limiting the accuracy. In thermodilution, one must carefully maintain the temperature of the injectate, or else it may cause the temperatures to deviate. Thermodilution is also unreliable in low cardiac output situations, where it tends to overestimate the cardiac output. Under low-flow conditions, the indicator has more time to equilibrate with the surrounding tissues, leading to diminished measured temperature changes and a smaller area under the curve, because heat exchange is assumed to only occur between blood and saline.

(c) Conductance Catheterization

In conductance catheter measurements, a catheter with multiple electrodes segmented along its length is inserted into the left ventricular chamber. The blood within the chamber is segmented into different volumes stacked together, with their boundaries defined by the left ventricular wall and the equipotential surfaces through the electrodes (171). Using the dielectric and conductive properties of the blood, each separate volume of blood can then be treated as a resistor and capacitor in parallel (171). The height is the distance between electrodes. The cross sectional area is the cross sectional area of the blood inside the left ventricle (171). This cross section varies over time throughout the cardiac cycle. The conductance, 1/R, can be modeled by (171):

$$\frac{1}{R(t)} = \frac{\sigma V(t)}{L^2}$$

where $\sigma$ is the conductance of the blood, V is the volume of the segment, and L is the length between electrodes. From there, the volumetric contribution of each segment to the stroke volume can be found (171):

$$\Delta V = \frac{L^2}{\sigma} \left( \frac{1}{R_{be}} - \frac{1}{R_{ee}} \right)$$

where R_be and R_ee are the resistances at the beginning and end of ejection, respectively.

The summation of each segment then gives the total stroke volume, and from there, ejection fraction and cardiac output may also be determined.

This method has the disadvantage of being highly invasive, requiring catheterization of the left ventricle. The conductivity of blood must also be calibrated. This can lead to errors, as the conductivity of blood changes throughout the cardiac cycle (see the Bioimpedance section). The model also assumes the equipotential surfaces to be parallel and the blood in the ventricle to be the only conducting objects, which may deviate from the real situation (171).

(d) Radionuclide Angiography

Traditionally, gamma cameras used in radionuclide angiography were too slow to perform continuous monitoring of left ventricular volume, ejection fraction, and cardiac output. However, now there are small and lightweight scintillation probes, which can perform radionuclide angiography right at the bedside. A radionuclide indicator is injected into the circulation, and the radionuclide count density is measured throughout the cardiac cycle (172, 173). The maximum count density throughout the cycle represents end-diastole, while the minimum represents end-systole (172). In this way, the ejection fraction may be determined with the following equation (172, 173):

$$EF = \frac{\text{end diastolic counts} - \text{end systolic counts}}{\text{total diastolic counts} - \text{background counts}}$$

Count averaging is used (roughly 5 heart beats) to increase the reliability of the measurement and raise the count density (172). The drawback of this approach is namely the ionizing radiation, which is safe in shorter timeframes, but unsuitable for extended monitoring. Because count averaging is used, irregular activities such as fibrillation or ectopic activities can affect the accuracy (172).

(e) Velocity Measurements

Cardiac output can also be found by measuring the blood velocity at a vessel, while knowing its diameter. Ways of measuring the blood velocity include Doppler ultrasound and electromagnetic flow probes. In Doppler ultrasound, the changes in the signal frequency are related to the blood flow velocity:

$$\frac{Fd}{Fs} = \frac{u}{x} \qquad (29)$$

where Fd is the frequency shift, Fs is the source frequency, u is the velocity, and x is the sound speed. Thus, by measuring the frequency shift, the flow velocity can be measured.

In electromagnetic flow probing, the probe is slipped around a blood vessel. According to Faraday's law of magnetic induction, a conductor (i.e., the blood in this case) moving through a magnetic field generates a voltage that is proportional to the velocity:

$$e = BLu \qquad (30)$$

where e is the induced voltage, B is the magnetic flux density, L is the spacing between electrodes, and u is the flow velocity.

Velocity measurements must first be calibrated by measuring the blood vessel diameter before it can be converted to cardiac output. In the case of Doppler, the angle of the probe to the blood flow must additionally be identified. While studies have found Doppler to be inaccurate in measuring cardiac output, especially in children, its strength is in monitoring the trends and its capability of detecting rapid changes. This makes it useful for monitoring surgical or fluid administration procedures in clinical settings. In addition, Doppler is one of the few non-invasive methods that measure cardiac output.

Electromagnetic flow probes face significant drawbacks in that they require the blood vessel to be fully exposed through surgery such that the probe can be positioned around the blood vessel. The accuracy of this method also depends strongly on how well the surgical exposure is done. Overall, it is an unfavorable method in most situations.

(f) Pulse Contour Analysis

In pulse contour analysis, the arterial pulse wave is recorded to produce a measurement of cardiac output. The area under the pulse wave curve is related to the stroke volume, and therefore the area under the curve times the heart rate can be related to the cardiac output. To derive the relationship for reliable monitoring, a three-element Windkessel model of the aorta's mechanical characteristics and the peripheral resistance of the body is used to represent the circulation. To calibrate the model, the relationship between the aortic pressure and cross-sectional area must be derived, so that the vessel compliance can be estimated. Studies have also further developed the model to be able to identify the stressed and unstressed states of the left ventricle and additionally calculate the ejection fraction.

Due to the significant amount of calibrations required for this approach, the accuracy is limited. In addition, as with most models, ideal conditions must be satisfied for the model to work well. Indeed, current commercial devices for measuring cardiac output via pulse contour analysis demonstrate a lack of ability to properly account for peripheral circulatory changes. The pulse contour analysis method can be unreliable during surgeries, such as during liver transplantation, where cirrhosis patients have high cardiac output and low fluctuating peripheral resistance.

(g) Bioimpedance

Bioimpedance techniques relate the changes of electrical impedance across the thorax to the cardiac cycle to monitor the cardiac performance. Bioimpedance is also one of the few non-invasive techniques for monitoring cardiac output. Classical methods of processing the impedance signals were dubious in their accuracy and whether they measured the blood flow of the heart at all. Patients with conditions such as pulmonary edema, where excessive lung water was present, repeatedly had poor results in validation studies of bioimpedance.

Recently, more reliable methods of processing the bioimpedance signals have been developed. Electrical velocimetry is based on the idea that red blood cells are randomly oriented when there is no blood flow in the aorta, and subsequently become aligned when the aortic valve opens. This alignment produces a change in the conductivity of the blood.

The overall bioimpedance measured can be modeled with the following equation:

$$Z(t) = Z_0 + \Delta Z_R + \Delta Z_C \qquad (31)$$

where $Z_0$ is the quasi-static background impedance, $\Delta Z_R$ is the artifact from respiration, and $\Delta Z_C$ is the impedance change due to the cardiac cycle.

From the impedance curve of $\Delta Z_C$, one can determine the acceleration of the blood flow based on the time taken to align the red blood cells An average velocity can then be estimated, and converted to stroke volume and cardiac output based on body mass.

On adults, electrical velocimetry is just within the 30% limits of agreement, but is not reliable in children, likely due to the body mass-based assumptions.

Additional Description of FIGS. 6-40

Figure 6A:
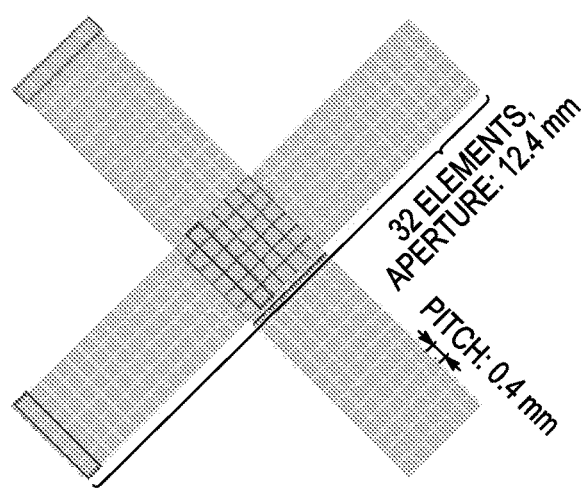
FIGS. 6(A)-6(C) show schematics and optical images of the orthogonal imager.
Figure 6B:
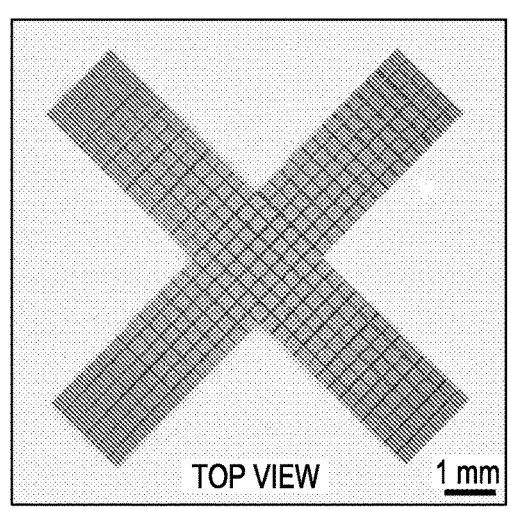
Figure 6C:
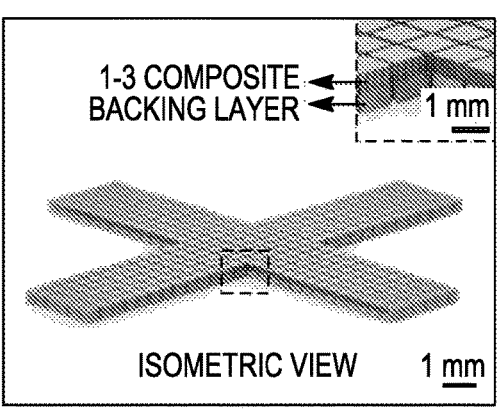

FIG. 6 shows schematics and optical images of the orthogonal imager. In particular, FIG. 6(A) shows the orthogonal imager consisting of four arms, where six tiny elements in one column are combined as one long element, and a central part that is shared by the four arms. The bold boxes label a long element integrated by six small pieces in each direction. The number of elements in one direction is 32. The pitch between the elements is 0.4 mm. FIG. 6(B) shows an optical image in top view and FIG. 6(C) shows an isometric view, showing the morphology of the orthogonal array. We used an automatic alignment strategy to fabricate the orthogonal array by bonding a large piece of backing layer with a large piece of 1-3 composite, and then dicing them together into small elements with designed configurations. The inset in FIG. 6(C) shows the details of the elements. The 1-3 composite and backing layer have been labelled.

FIG. 7 presents characterization data for the transducer array. In particular, FIG. 7(A) shows the electrical impedance spectrum with the amplitude and phase angle. It shows the 3 MHz resonance frequency and 3.87 MHz antiresonant frequency. The calculated electromechanical coupling coefficient is 0.67. 7(B) Map of the dielectric loss of all transducer elements in the orthogonal imager. FIG. 7(C) shows the pulse-echo response and corresponding frequency spectrum of the transducers, showing a wide bandwidth of ~55% and a central frequency of 3 MHz. FIG. 7(D) shows the crosstalk between a pair of adjacent elements and a pair of second nearest neighbors, which is lower than the standard-30 dB indicated by the dashed line.

Figures 8A, 8B, 8C, 8D, 8E, 8F:
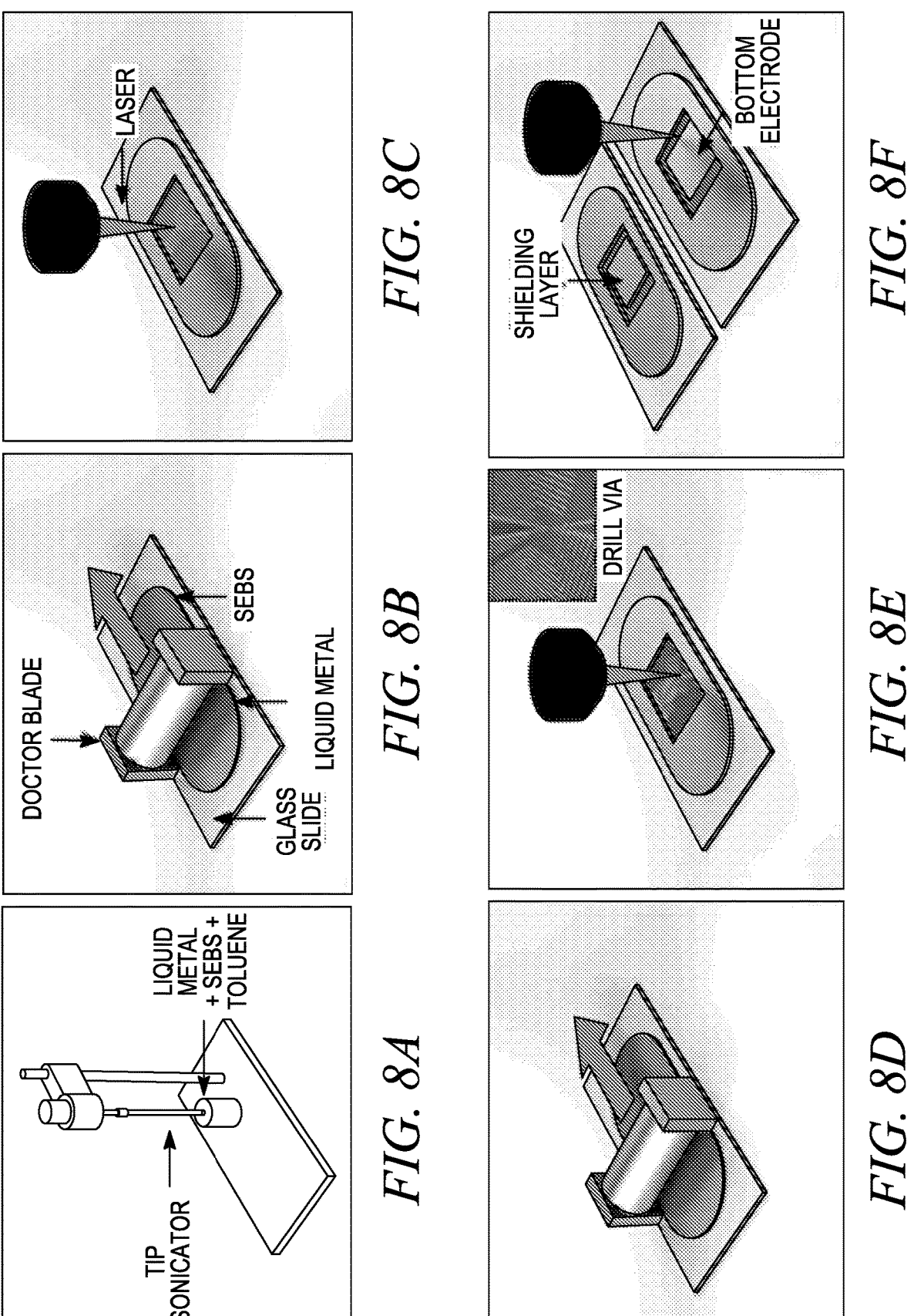
FIGS. 8(A)-8(M) illustrate the fabrication processes for the wearable imager.
Figures 8G, 8H, 8I, 8J, 8K, 8L:
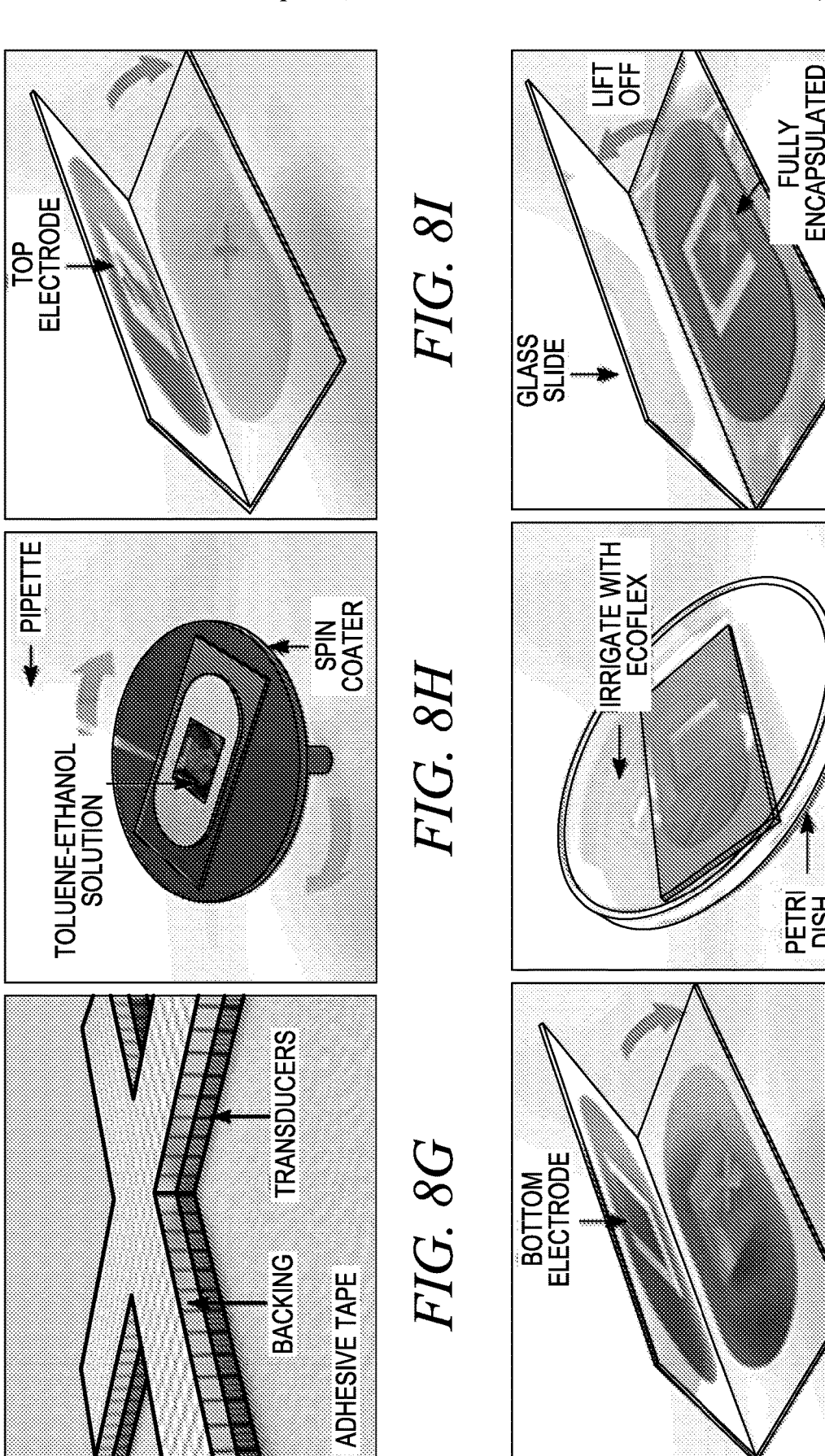
Figure 8M:
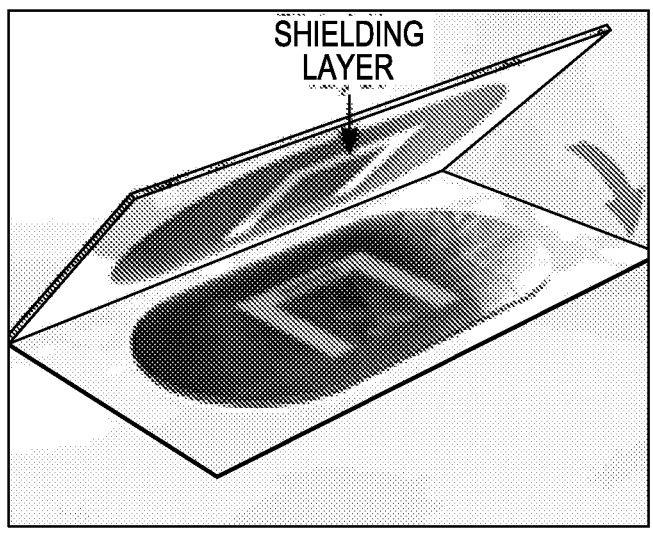
Figure 9A:
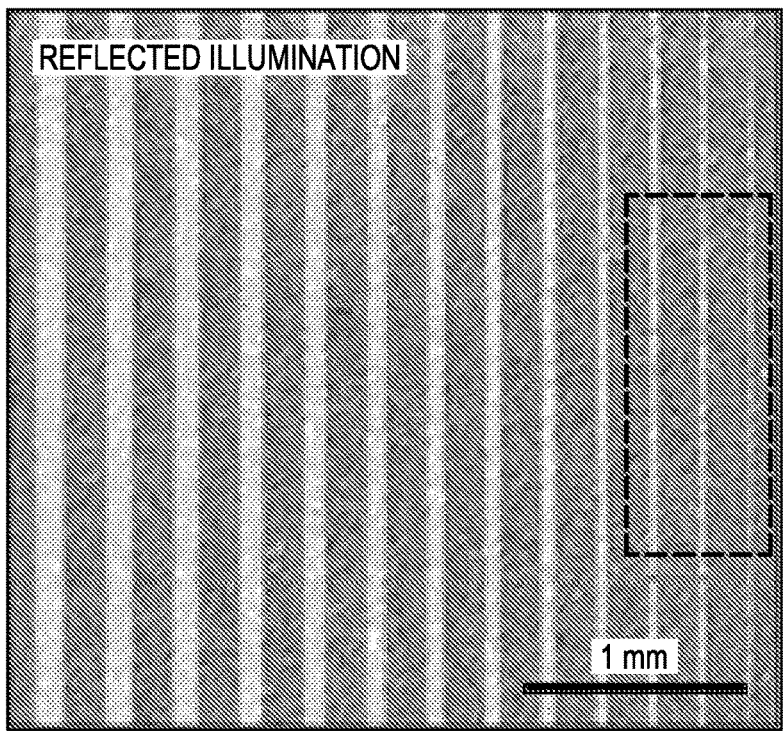
FIGS. 9(A)-9(D) are images showing the fabrication resolution of the liquid metal electrodes.
Figure 9B:
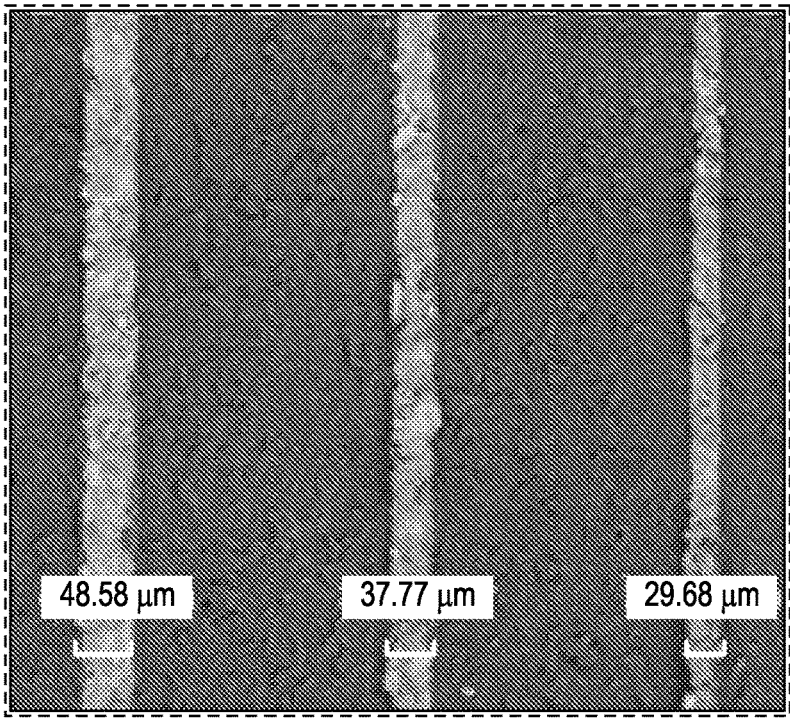
Figure 9C:
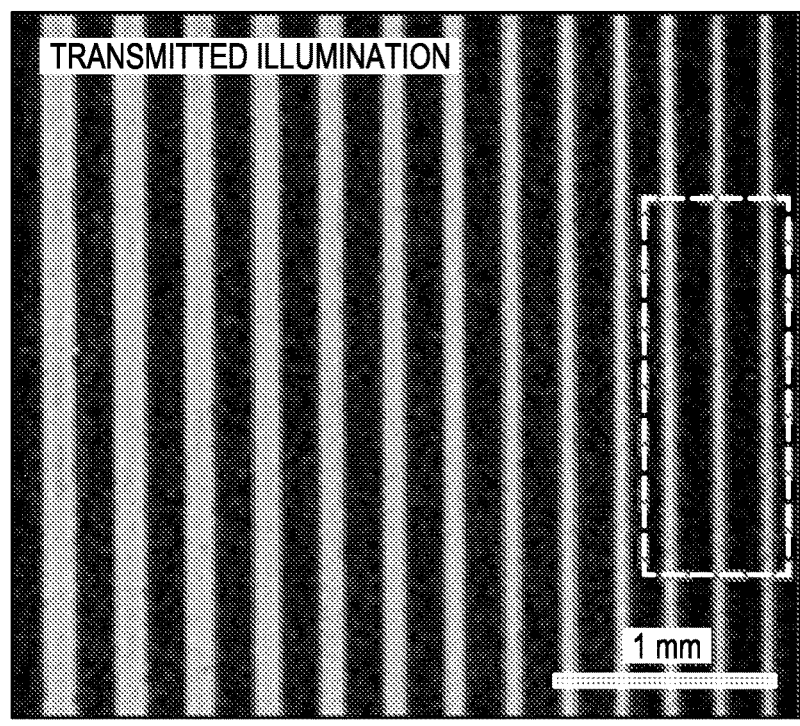
Figure 9D:
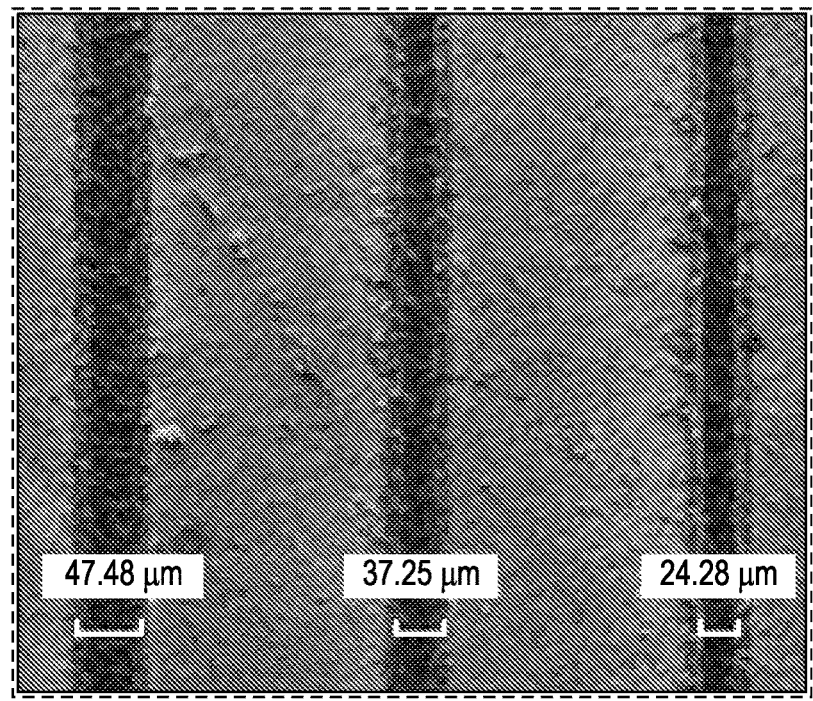

FIG. 8 illustrates the fabrication processes of the wearable imager. In particular, FIG. 8(A) shows a sonicate liquid metal in toluene to homogenize the materials. FIG. 8(B)

shows the print liquid metal on a SEBS substrate using a doctor blade. FIG. 8(C) shows the patterning of the liquid metal-based electrode using laser ablation. FIG. 8(D) shows the printing of a subsequent layer of liquid metal insulated with a layer of SEBS on the previous electrode. More layers of electrodes can be fabrication by repeating this step. FIG. 8(E) shows the drilling of vertical-interconnect-accesses (VIAs) using laser ablation to allow electrical connection between the top electrodes and transducers. FIG. 8(F) shows the patterning of the shielding layer, bottom electrode, and alignment mask using laser ablation. FIG. 8(G) shows the dicing of the transducer array together with the backing layer. FIG. 8(H) shows spin coating toluene onto the electrodes to allow adhesion between electrodes and transducers. FIG. 8(I) shows the bonding of the top electrodes to the transducer array. FIG. 8(J) shows bonding the bottom electrode to the transducer array. FIG. 8(K) shows the irrigation of the gap between the two glass slides with Ecoflex to encapsulate the device. FIG. 8(L) shows lift off from the glass slides to release the device. FIG. 8(M) shows the softening and bonding of the shielding layer to the device.

FIG. 9 are images showing the fabrication resolution of the liquid metal electrodes. In particular, FIG. 9(A) shows an optical image with reflected illumination and FIG. 9(B) shows a scanning electron microscope image, showing the minimum width of the liquid metal electrodes. FIG. 9(C) shows an optical image with transmitted illumination and FIG. 9(D) shows a scanning electron microscope image, showing the narrowest grooves on the liquid metal electrodes patterned by laser ablation.

Figure 10A:
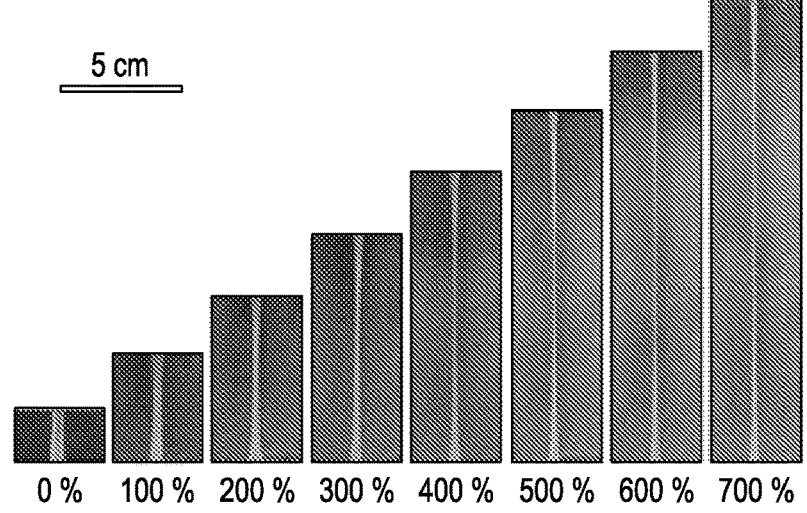
FIGS. 10(A)-10(C) show the results of mechanical testing of the liquid metal electrodes.
Figure 10B:
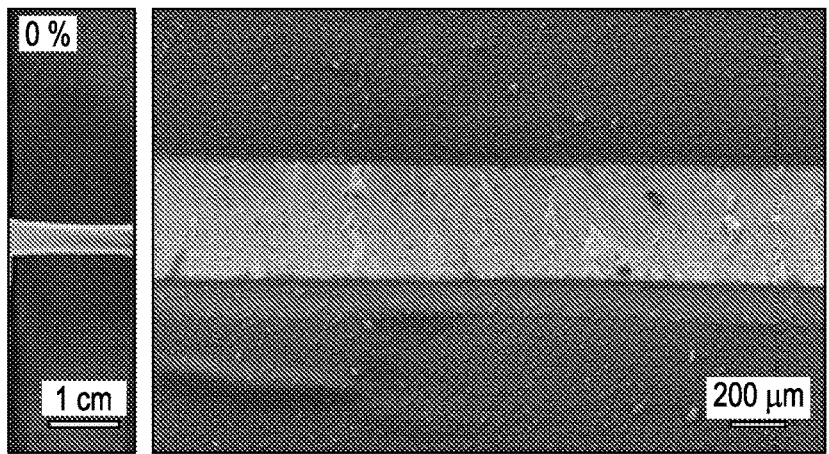
Figure 10C:
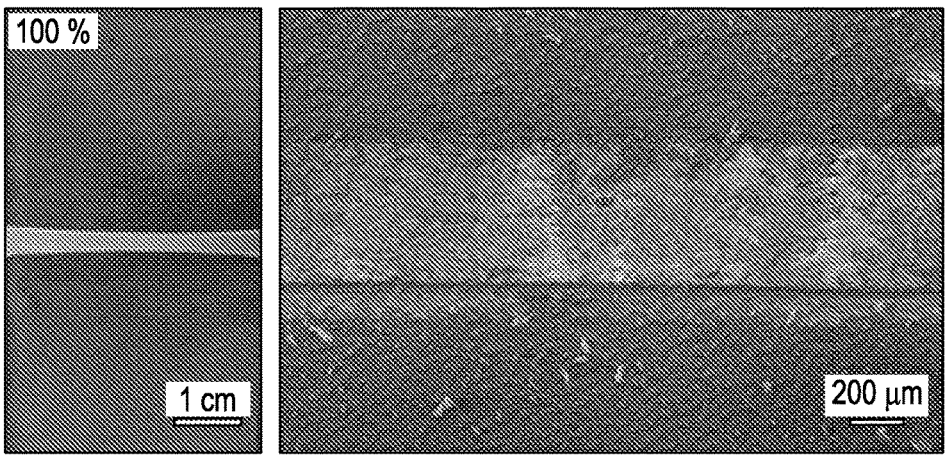
Figure 11C:
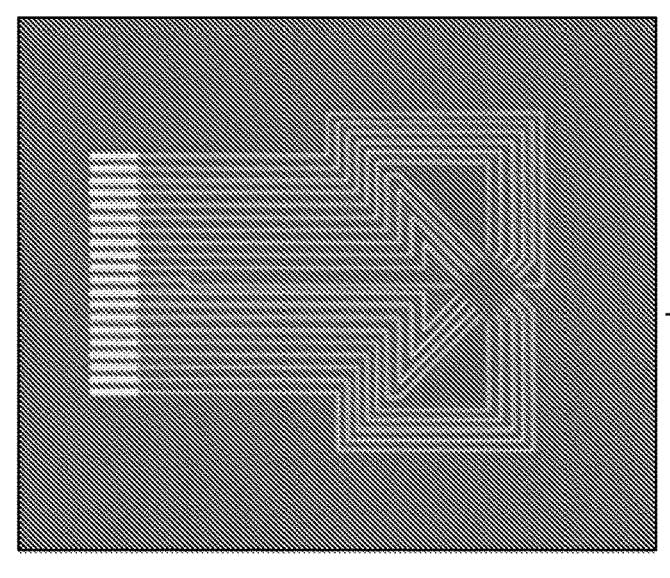
FIGS. 11(A)-11(F) show optical images of the multilayered liquid metal electrodes.
Figure 11B:
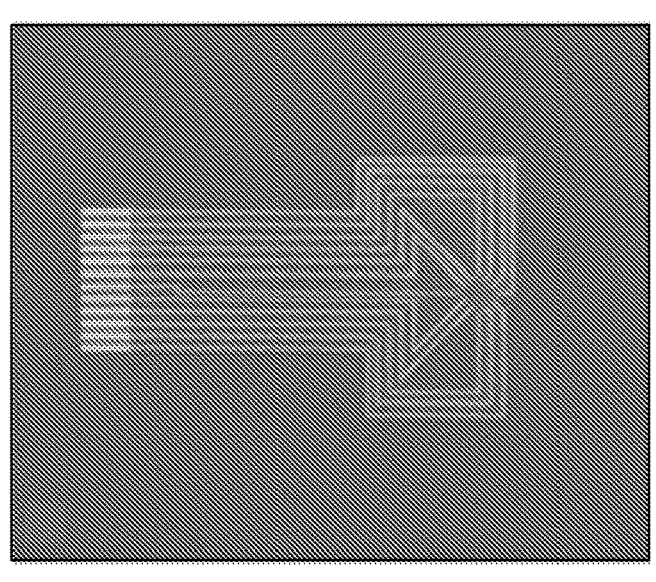
Figure 11A:
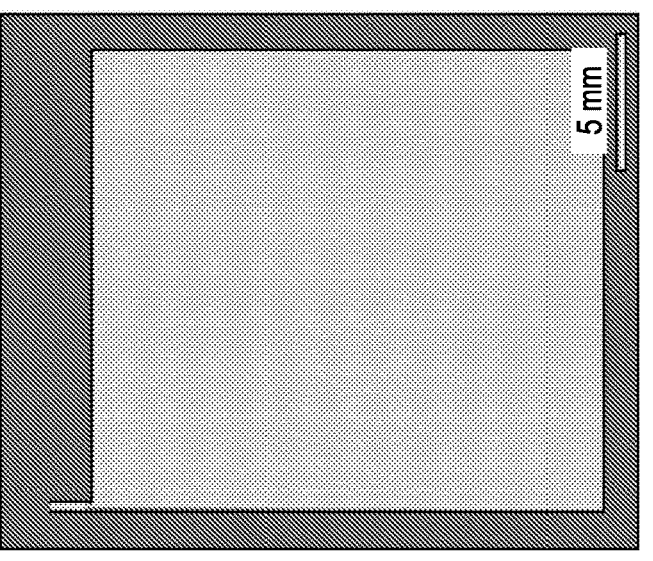
Figure 11F:
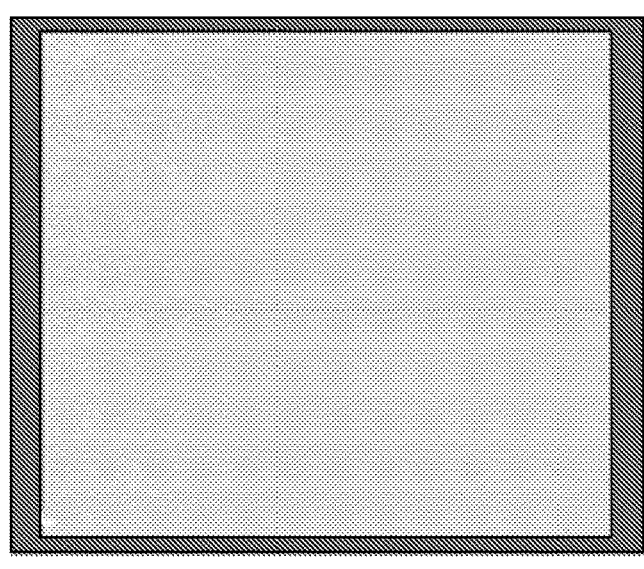
Figure 11E:
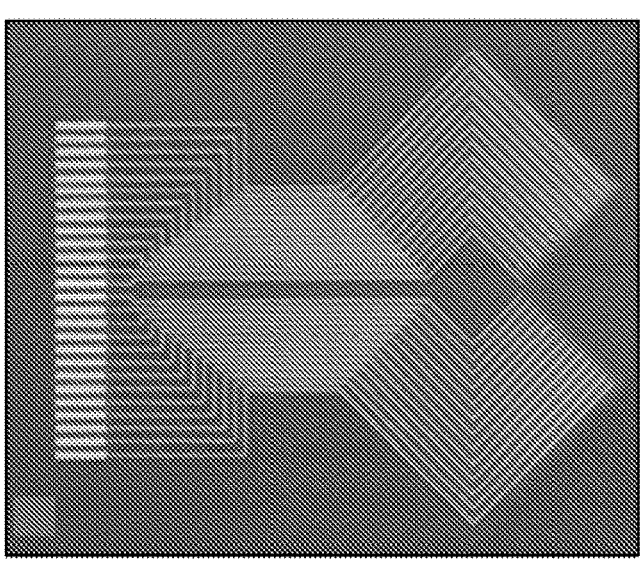
Figure 11D:
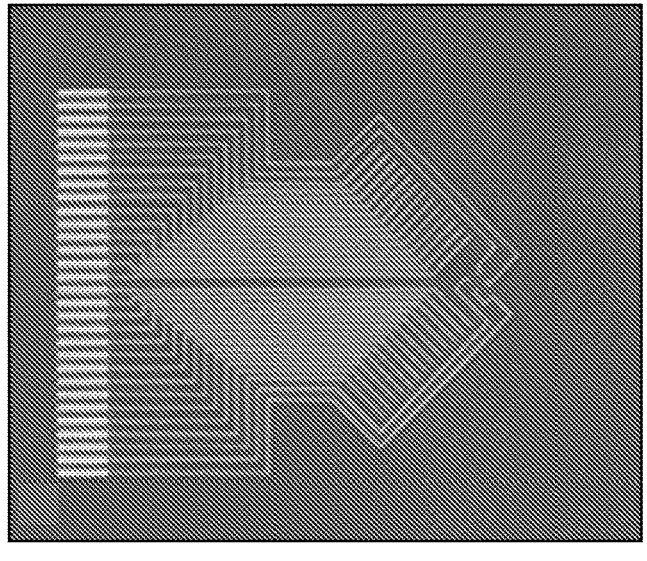

FIG. 10 shows the results of a mechanical testing of the liquid metal electrodes. In particular, FIG. 10(A) shows that the maximum stretchability is ~700% of this device. Optical and scanning electron microscope images of the liquid metal electrodes before (FIG. 10B) and after (FIG. 10C) uniaxially stretching for 100% strain. There are no visible cracks in the electrode after stretching, indicating its excellent intrinsic stretchability.

FIG. 11 shows optical images of the multilayered liquid metal electrodes. In particular, FIG. 11(A) shows the ground electrode, FIG. 11(B) shows the first layer, FIG. 11(C) shows the second layer, FIG. 11(D) shows the third layer, FIG. 11(E) shows the fourth layer and FIG. 11(F) shows the shielding layer. All images share the same scale bar.

Figure 12A:
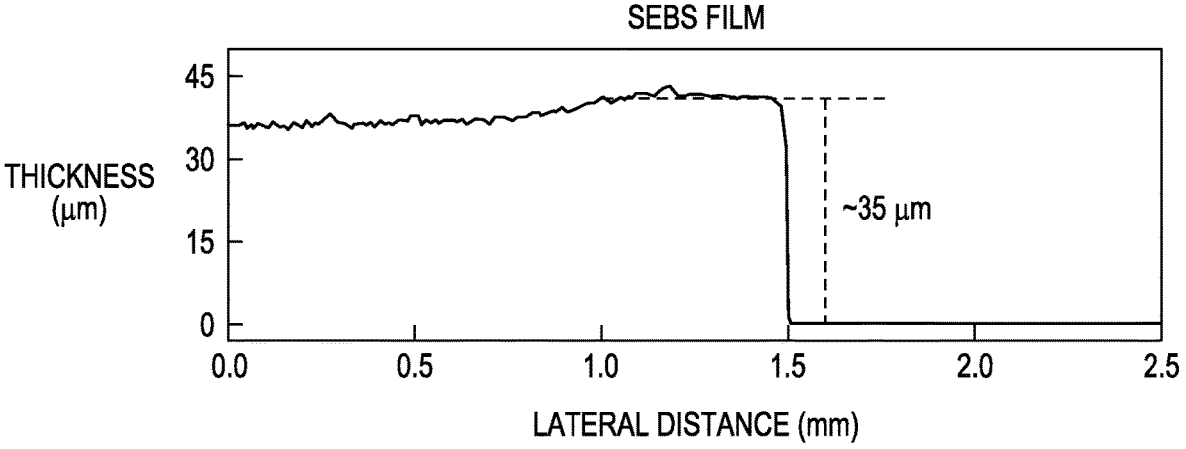
FIGS. 12(A)-12(B) show the thickness of the SEBS substrate and the printed liquid metal.
Figure 12B:
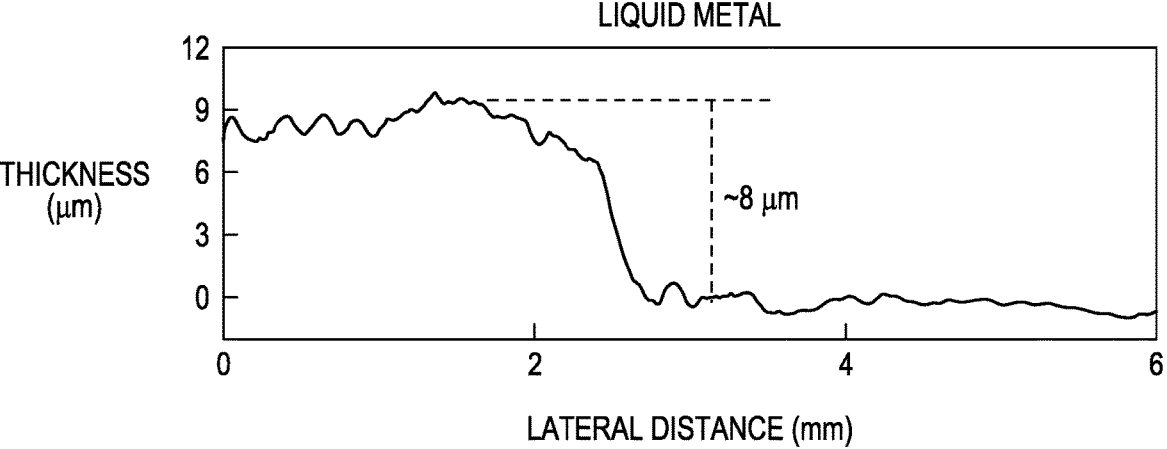

FIG. 12 shows the thickness of the SEBS substrate and the printed liquid metal. In particular, FIG. 12(A) shows the thicknesses of the SEBS film and FIG. 12(B) shows the liquid metal layer as measured by a Dektak profilometer. The thin thicknesses of the substrate and the electrode contribute to the overall low form-factor of the wearable imager.

Figure 13:
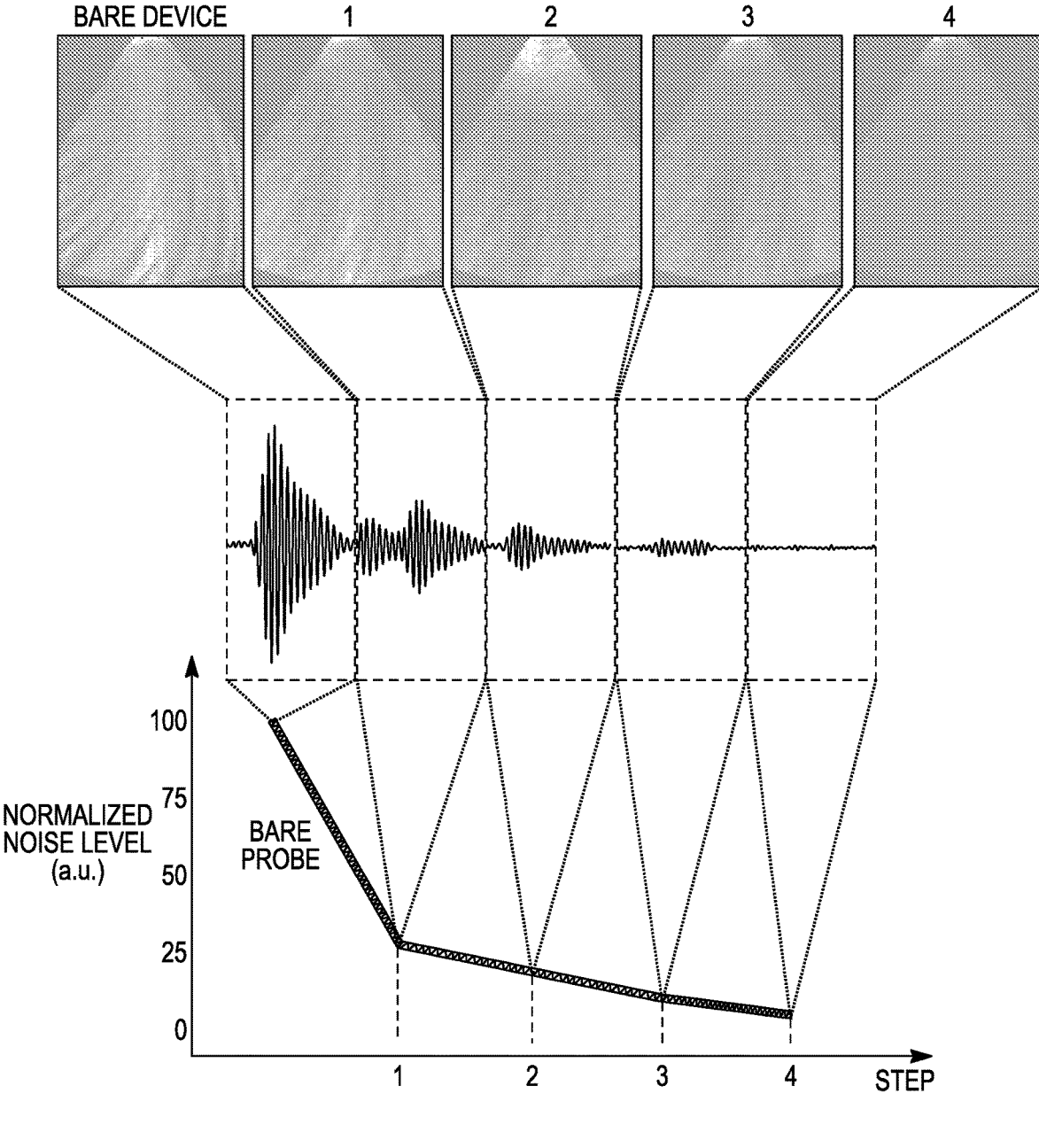
FIG. 13 presents characterization data of noise levels after applying different strategies sequentially.

FIG. 13 presents characterization data of noise levels after applying different strategies sequentially. Step 1: Electrical matching between the transducer and the pulser. Step 2: Shielding electrode. Step 3: Ground wire modification by adding an inductor and capacitor in series to the ground wire. The modification rendered the ground wire to be more resistive at around the center frequency and drain noise at around center frequency to the ground better. Other noise can be effectively removed by filters. Step 4: Signal accumulation, which is a built-in function provided by Verasonics. The signal accumulation overlaps recent frames to counteract the running noise. We normalized the noise level by dividing all noise levels by the highest noise level for better comparison.

Figure 14:
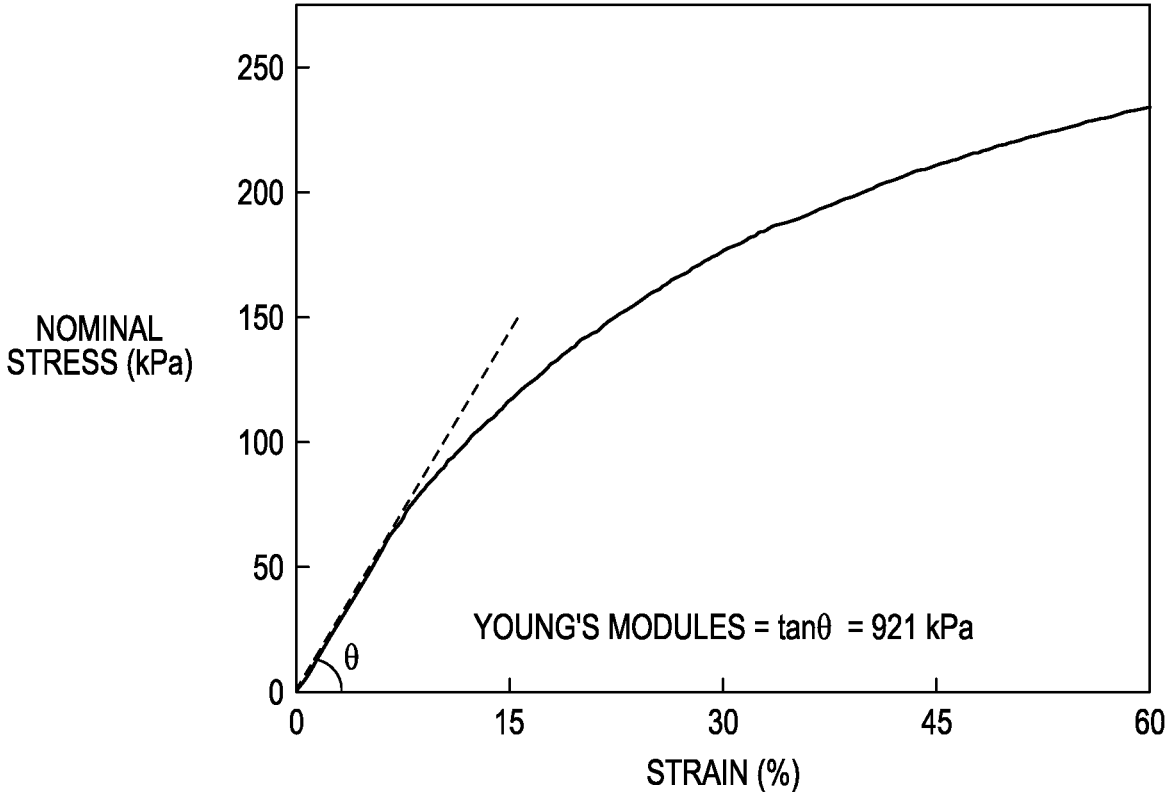
FIG. 14 shows a tress-strain curve of the entire device.

FIG. 14 shows a stress-strain curve of the entire device. The cardiac imager was stretched uniaxially, from which the Young's modulus of the entire device is calculated to be 921 kPa. It shows the device has a similar modulus to the human skin (420 to 850 kPa).

Figure 15A:
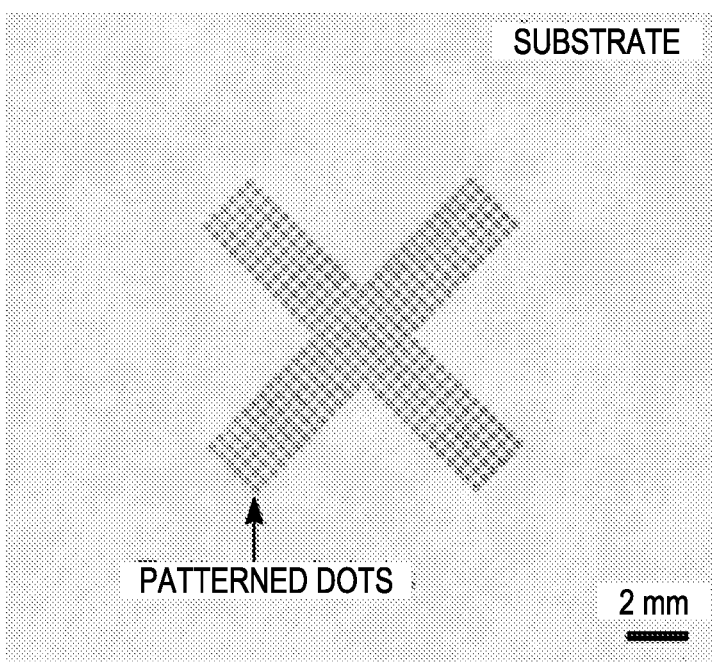
FIGS. 15(A)-15(B) illustrate biaxial mechanical testing of the entire device
Figure 15B:
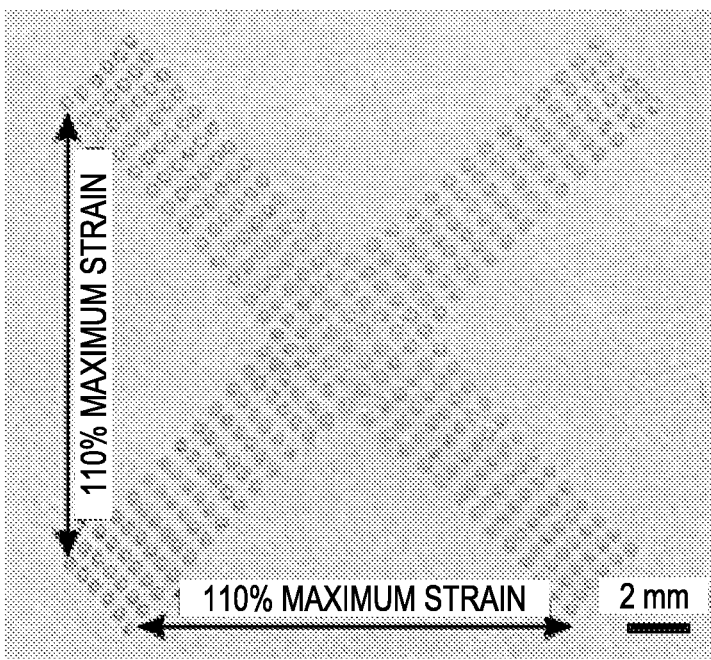

FIG. 15 illustrates biaxial mechanical testing of the entire device. Because the shielding and ground layers are opaque, we patterned dots on the triblock copolymer substrate to represent the location of each transducer element. The optical images show the device before (FIG. 15A) and after (FIG. 15B) stretching. The spatial distribution of array elements is comparable to that obtained through simulation in FIG. 1E, verifying the accuracy of the simulation result.

Figure 16:
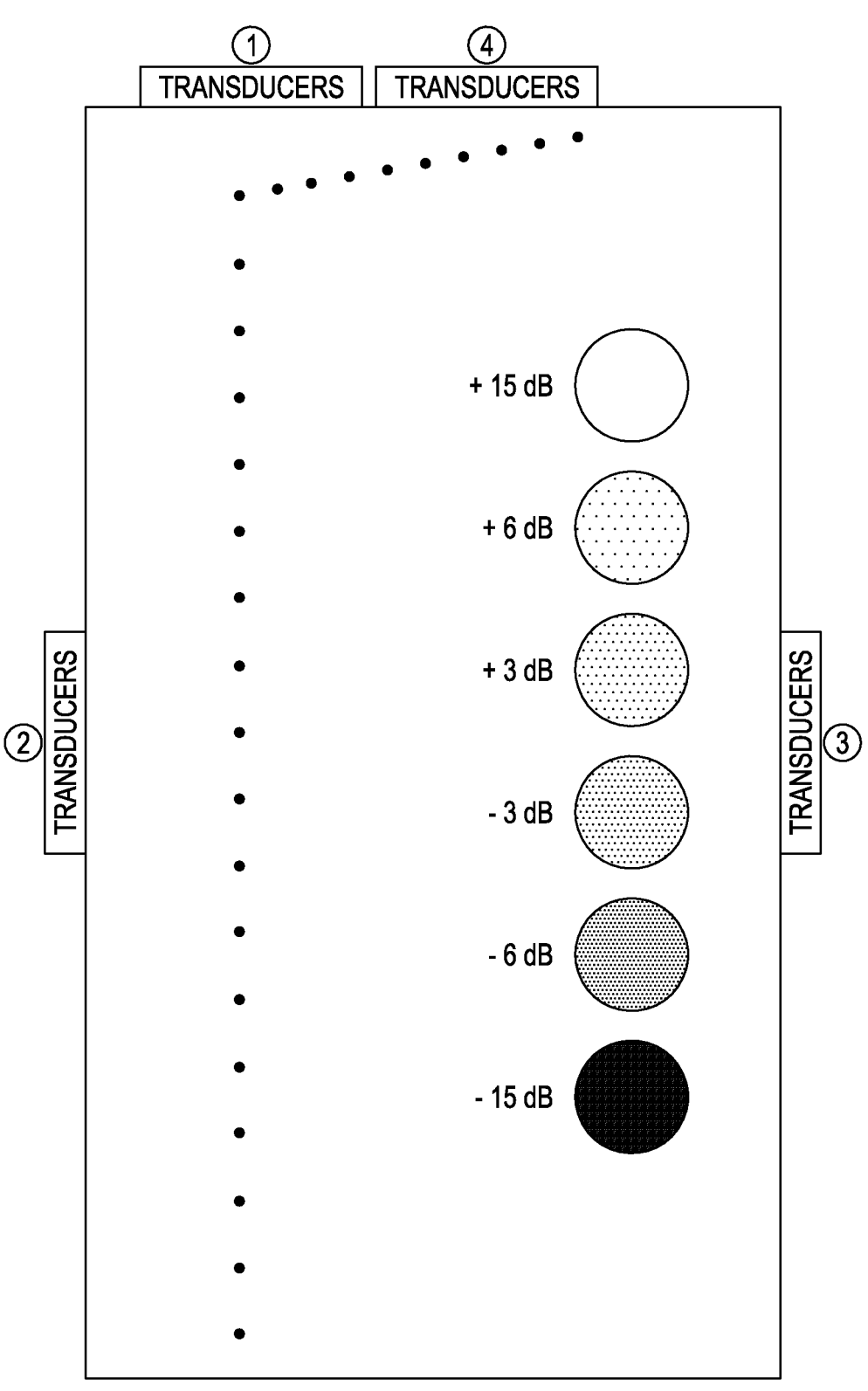
FIG. 16 shows the structure of the phantom for device characterizations.
Figure 17A:
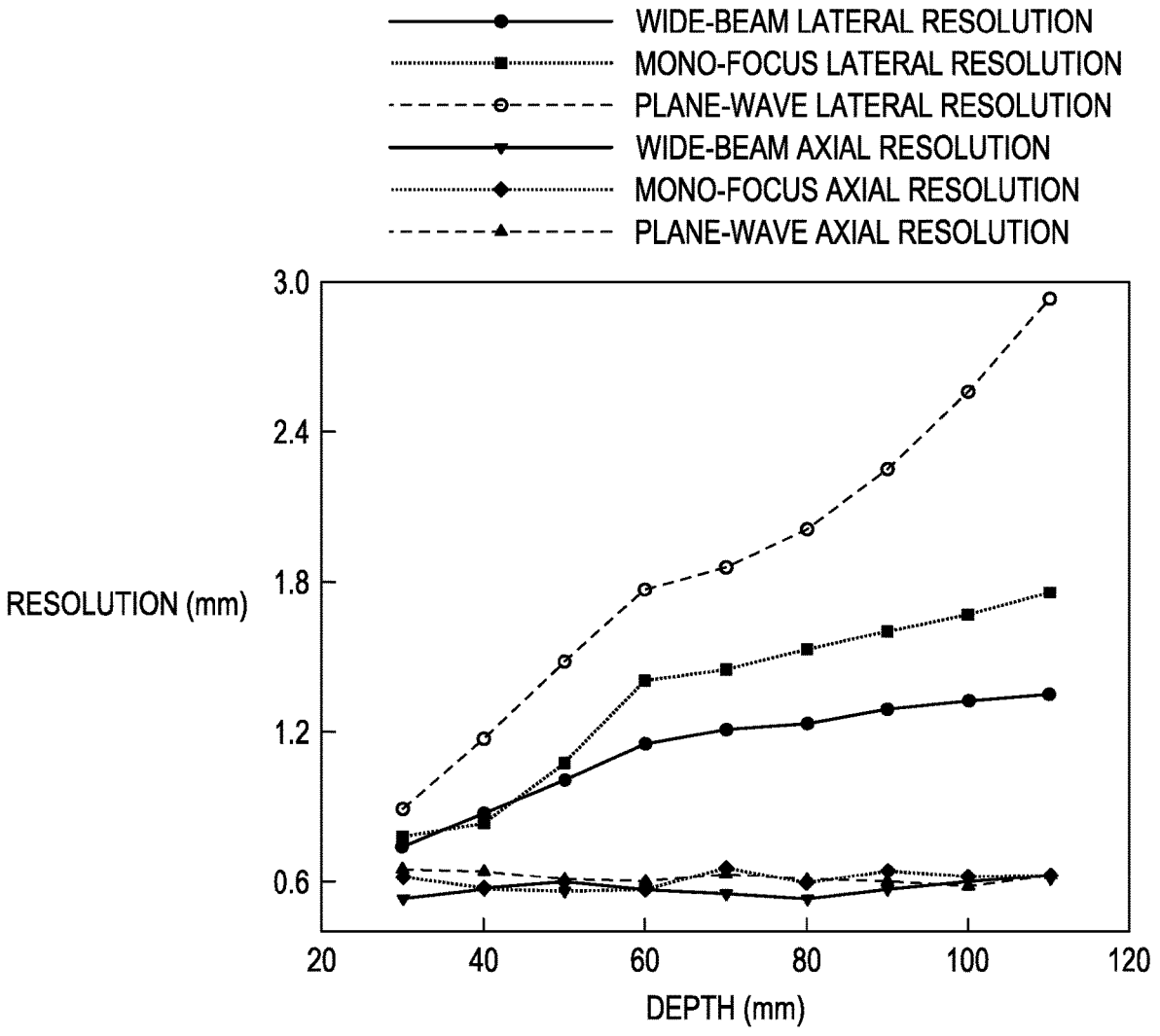
FIGS. 17(A)-17(D) present characterization data of resolutions and acoustic fields with different transmission methods and angles.
Figure 17B:
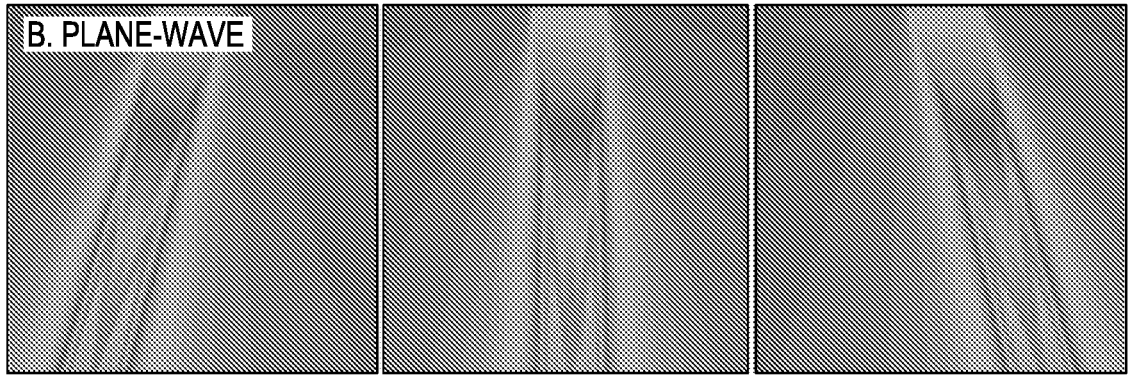
Figure 17C:
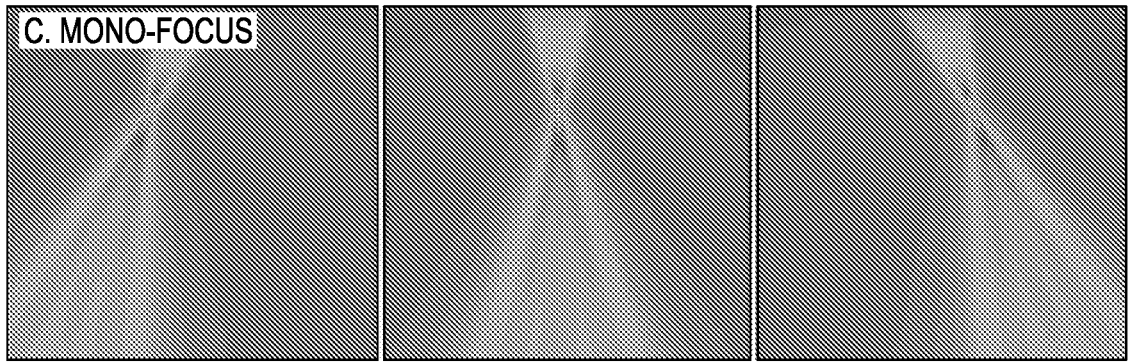
Figure 17D:
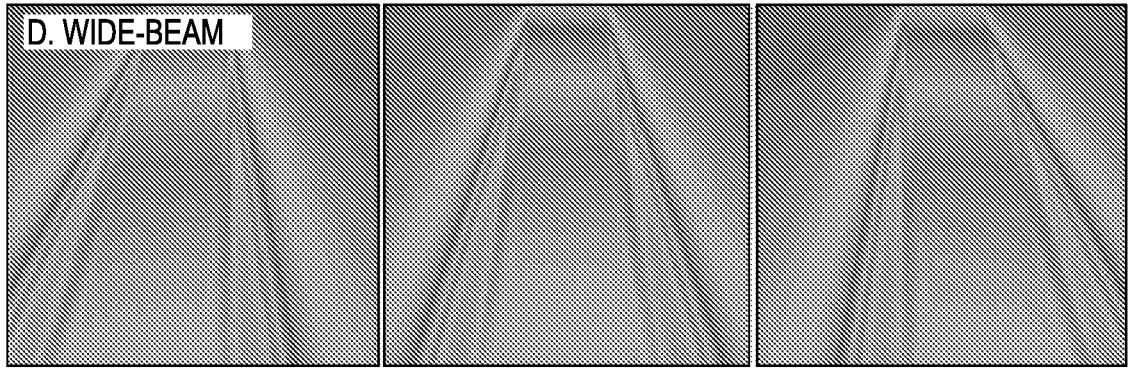

FIG. 16 shows the structure of the phantom for device characterizations. We used a commercial phantom (CIRS 539) to characterize multiple properties of the wearable imager. The signal-to-noise ratio, axial, lateral and elevational resolutions at different depths, and axial accuracy were tested when the device was put at the position 1. The lateral accuracy, as well as axial and lateral resolutions at different lateral distances, were tested when the device was put at position 2. The dynamic range, contrast-to-noise ratio, and contrast resolution were tested when the device was put at position 3. The dead zone was tested when the device was put at position 4.

FIG. 17 presents characterization data of resolutions and acoustic fields with different transmission methods and angles. In particular, FIG. 17(A) shows the lateral and axial resolutions with wide-beam compounding, mono-focus, and planewave transmission. The wide-beam compounding transmission has the best resolutions among all three. Acoustic fields of plane wave (FIG. 17B), mono-focus (FIG. 17C) and wide-beam compounding (FIG. 17D) transmission methods, with transmission angles of –21°, 0°, and 21°. The wide beam compounding transmission has a stronger and more uniform acoustic wave intensity over a larger area than the other two.

FIG. 18 illustrates the mechanism of wide-beam compounding B-mode imaging. Multiple frames are first acquired with multiple transmissions at different angles. The multiple-angle scan compensates the low echoic energies from regions away from center, expanding the insonation area from being rectangular to fan-shaped. The enhanced echoic energy improves the resolution at high steering angles. The frames are collected at the same rate as the high pulse repetition frequency. The final image is obtained by the superposition of acquired frames, which achieve synthetic focusing with improved resolution over the entire ultrasonographic window. Additionally, the superposition helps eliminate the random noise in the images.

Figure 19:
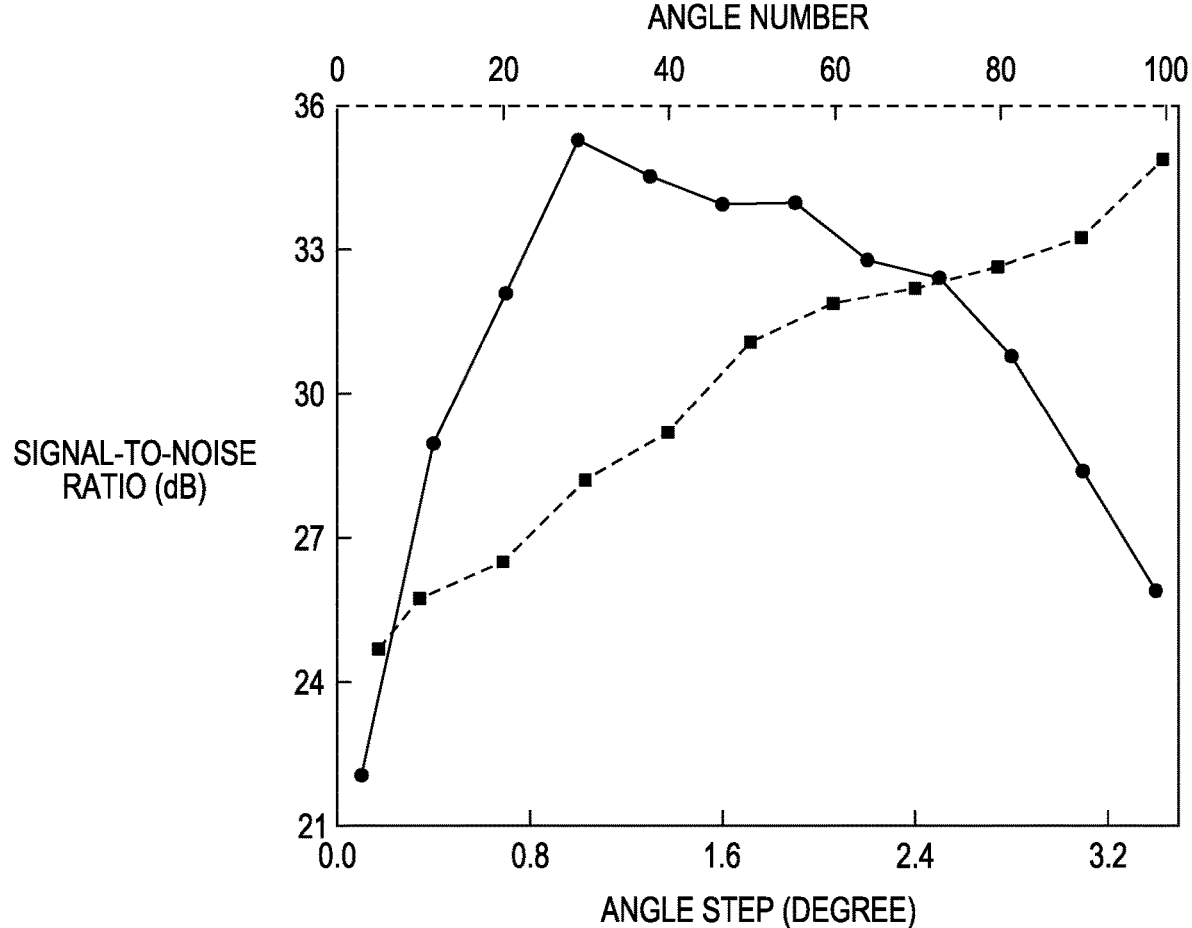
FIG. 19 shows the signal-to-noise ratio as a function of step size and number of steering angles of the compounding imaging.

FIG. 19 shows the signal-to-noise ratio as a function of step size and number of steering angles of the compounding imaging. The image's signal-to-noise ratio firstly rises and then falls with the angle step size but increases monotonically with the angle number. When the angle step size initially increases, the most constructive interference of multiple acoustic fields is in the region of interest, ensuring the highest signal-to-noise ratio for the image reconstruction. As the angle step size keeps increasing, the overlap between individual acoustic fields decreases, resulting in a reduced signal-to-noise ratio. The signal-to-noise ratio increases as the number of angles grows, because all individual acoustic fields are more or less coherently integrated to reconstruct a compounded image. However, an excessive number of angles sacrifices the imaging temporal resolution.

Figure 20A:
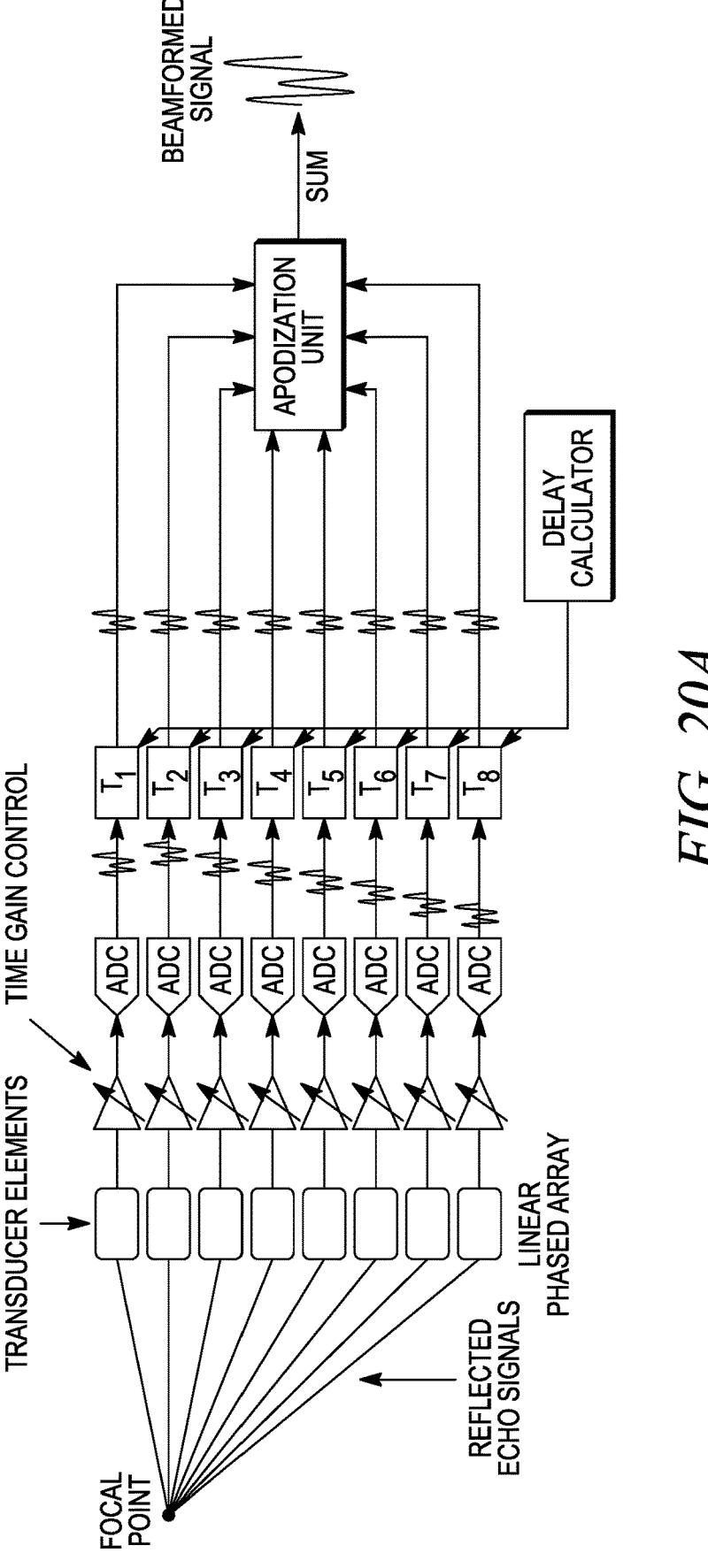
FIGS. 20(A)-20(C) illustrate the process of the receive beamforming.
Figure 20B:
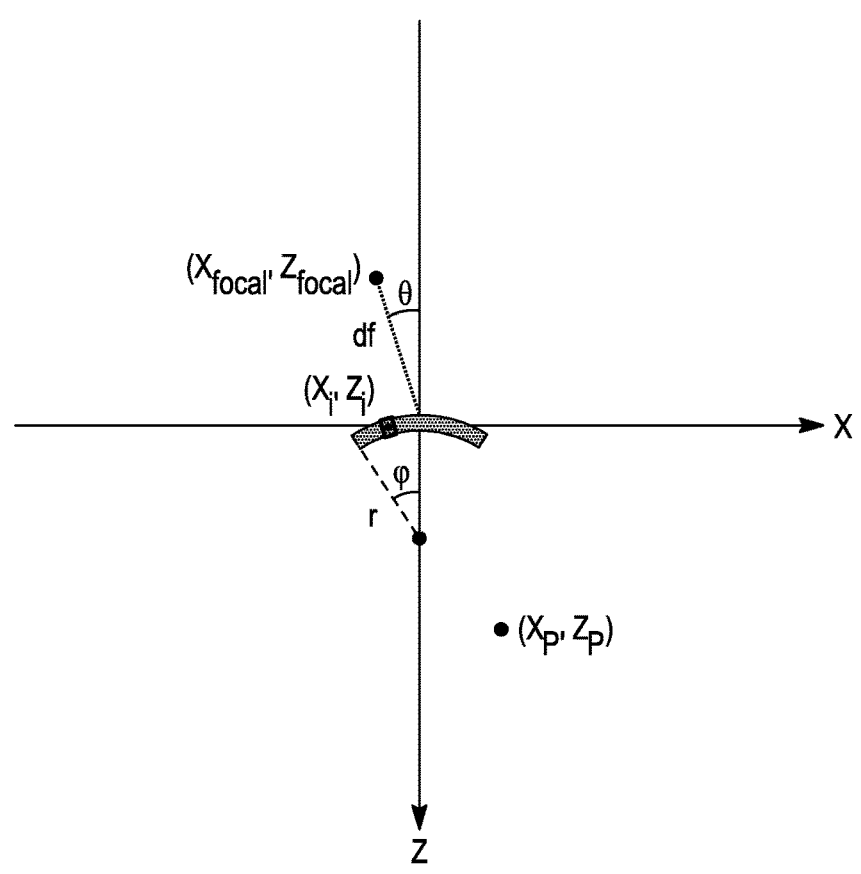
Figure 20C:
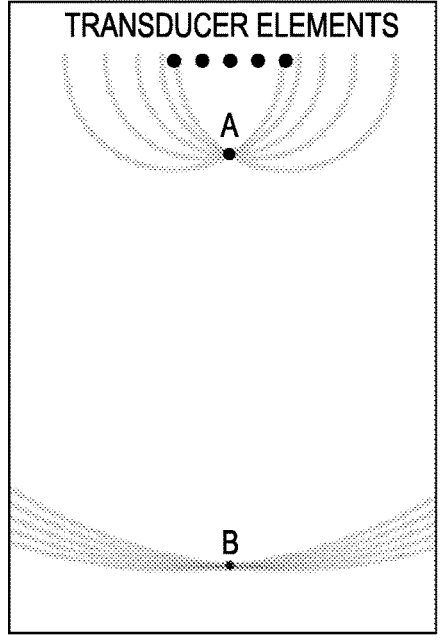

FIG. 20 illustrates the process of the receive beamforming. In particular, FIG. 20(A) shows the reflected echoes are received by the transducer elements, whose signals are amplified by the time gain control to enhance the weak signals from deep objects. The amplified signals are then converted to digital signals by an analog to digital converter (ADC), and then sent into a delay calculator for phase difference correction and signal alignment. Direct summing of the synchronized signals may result in significant side-lobe artifacts. Therefore, adaptive apodization assigns varying weights to the various signals, which are eventually summed together as beamformed signals with an enhanced signal-to-noise ratio. FIG. 20(B) is a schematic illustrating that the calculation for phase correction. $(x_{focal}, z_{focal})$ is the focal point. $(x_i, z_i)$ is the $i^{th}$ transducer. $(x_p, z_p)$ is the pixel of interest. $\theta$ is the steering angle. df is the focal depth. r is the curvature radius. $\varphi$ is the angle departure of the $i^{th}$ transducer from z-axis on the curvature. FIG. 20(C) schematically illustrates receiving beamforming of ultrasound signals. There are two beamformed signals A and B. The lateral diffusion in A is less than that in B, which indicates a better lateral resolution of A. In other words, the closer the imaging area to the transducer element, the better the lateral resolution.

Figure 21:
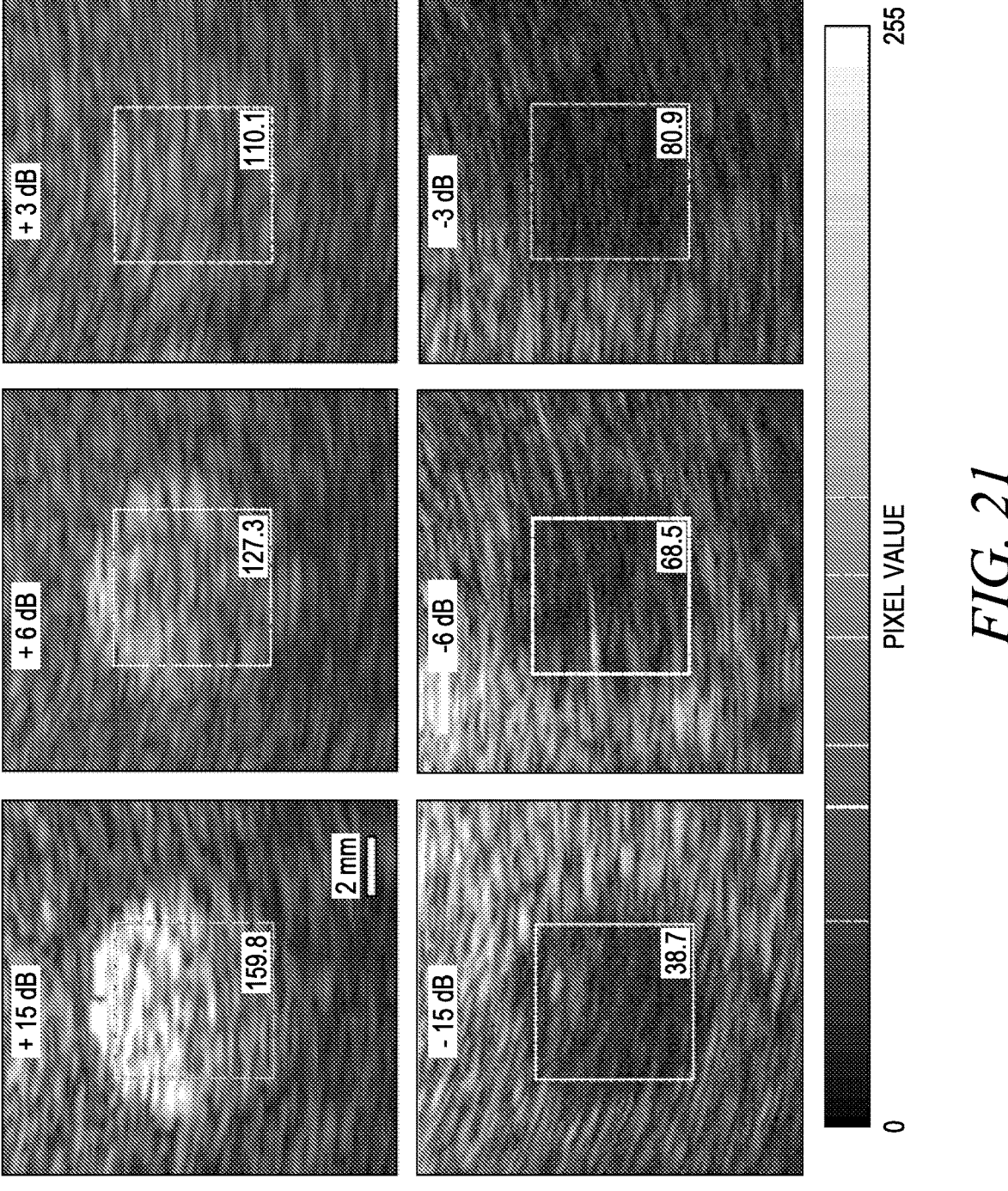
FIG. 21 shows gray scale B-mode images of phantoms and selected windows for calculating the dynamic range.
Figure 22A:
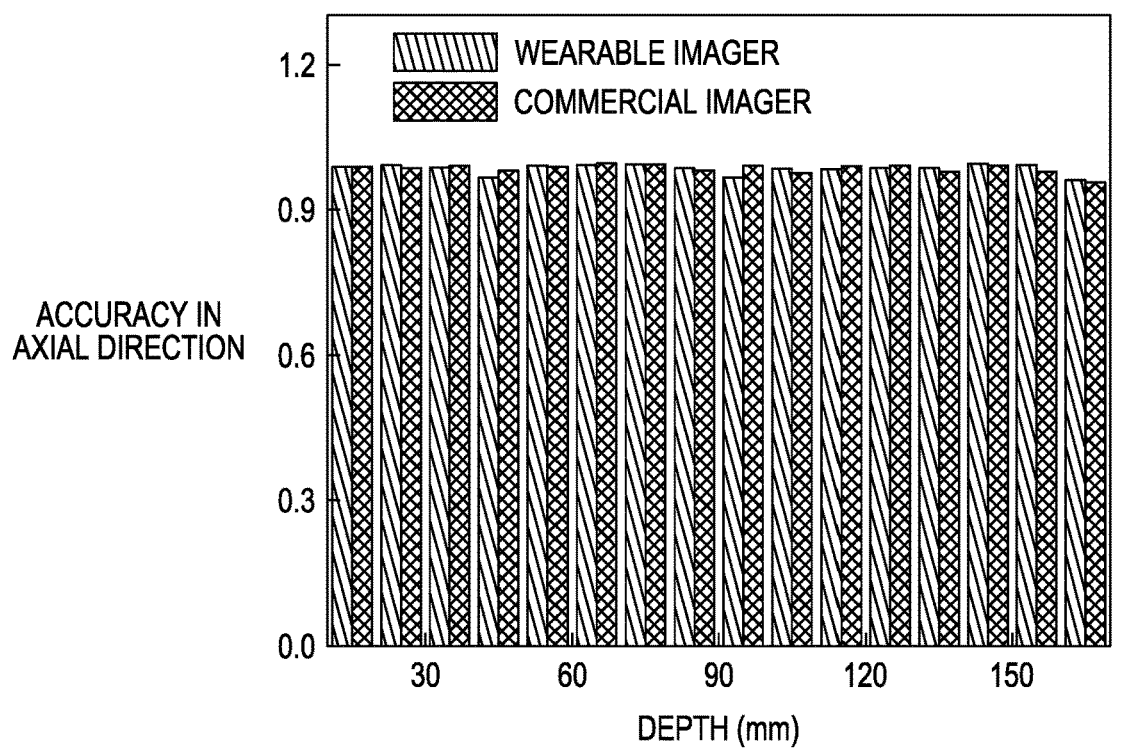
FIGS. 22(A)-22(D) present a detailed comparison of the imaging metrics between the wearable and the commercial imagers.
Figure 22B:
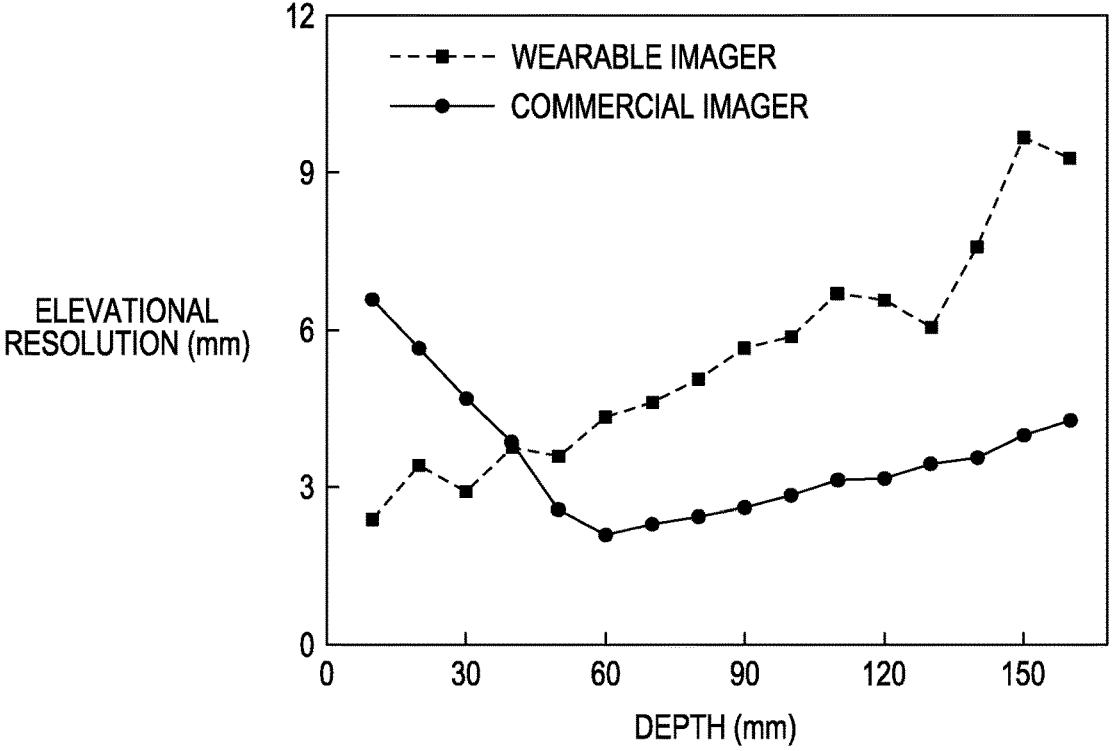
Figure 22C:
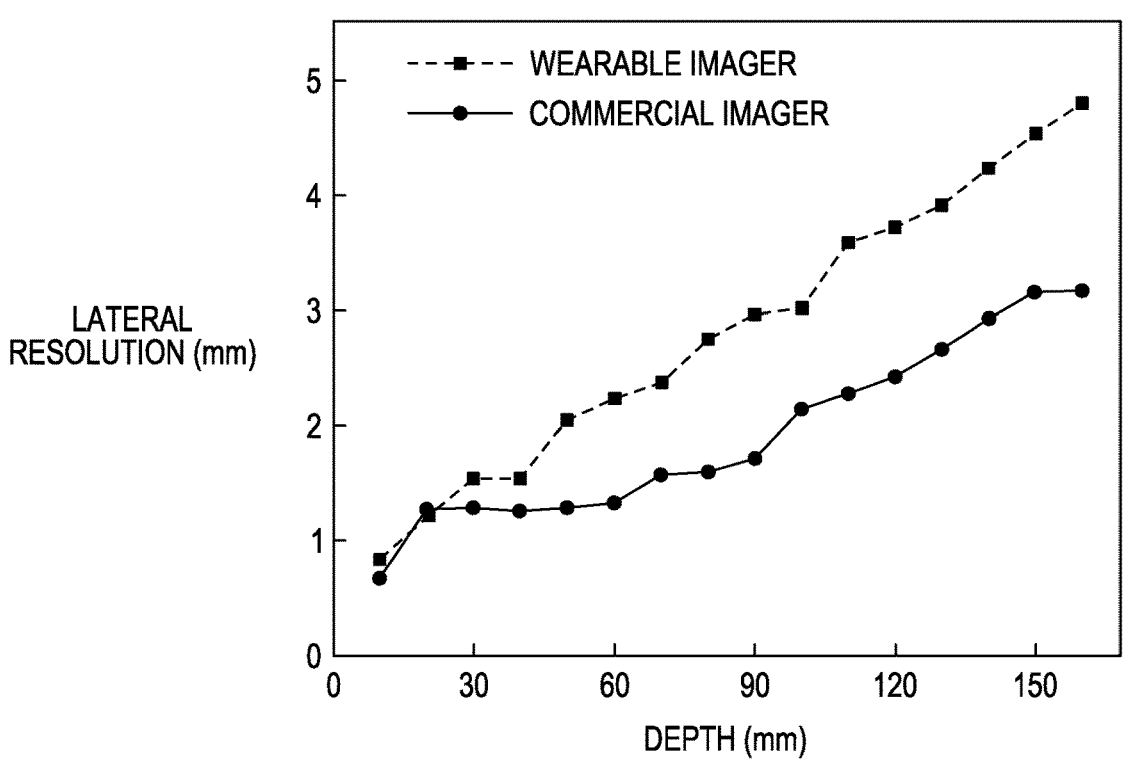
Figure 22D:
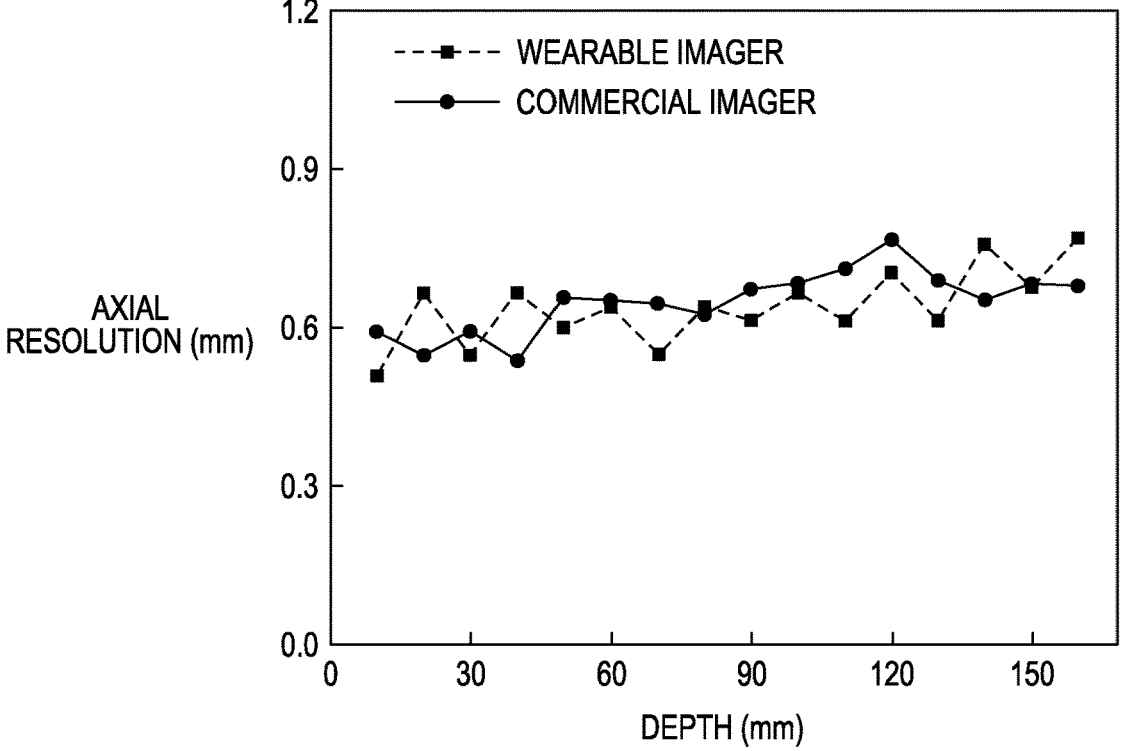
Figures 23A, 23B:
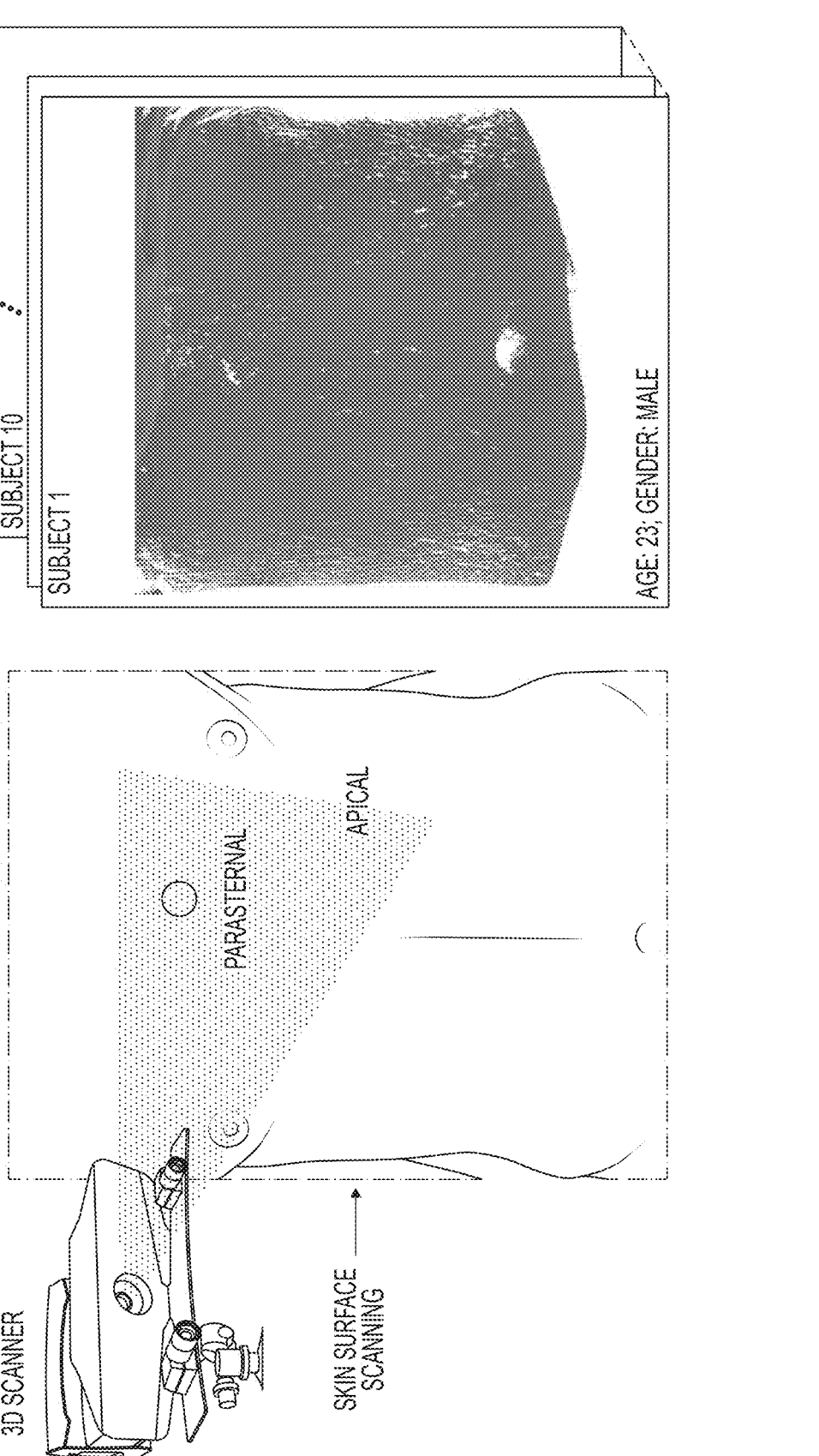
FIGS. 23(A)-23(F) illustrate processes of evaluating the surface curvature for phase correction.
Figure 23D:
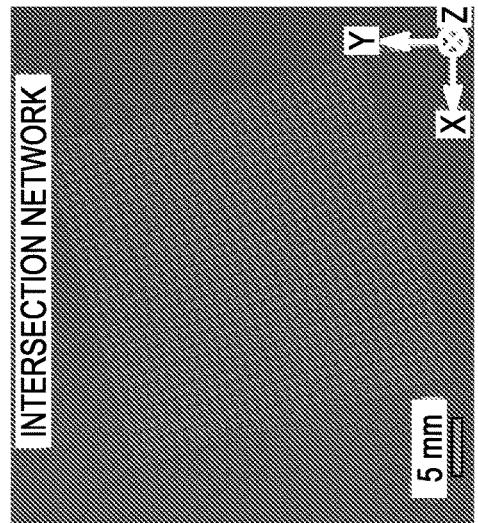
Figure 23D:
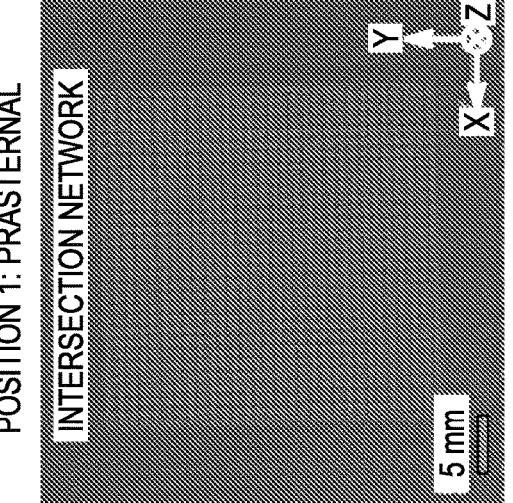
Figure 23C:
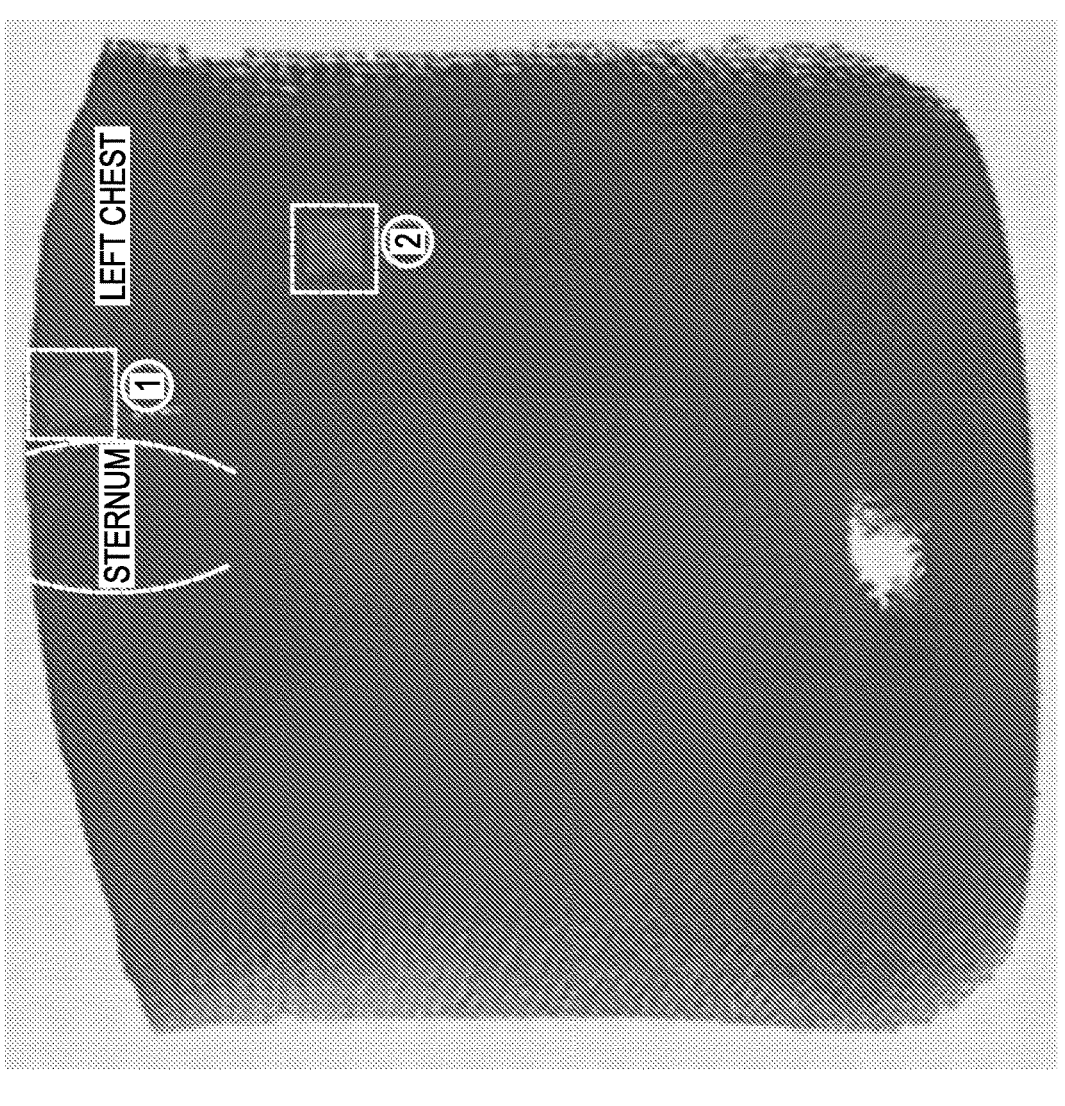
Figure 23E:
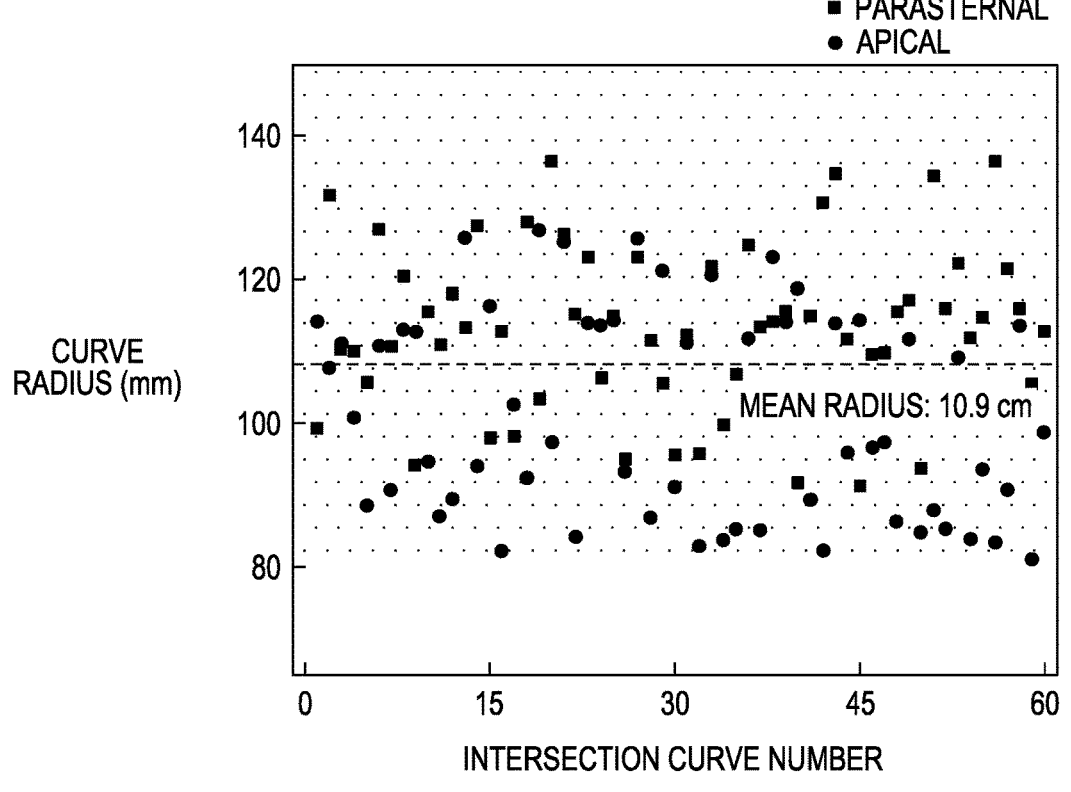
Figure 23F:
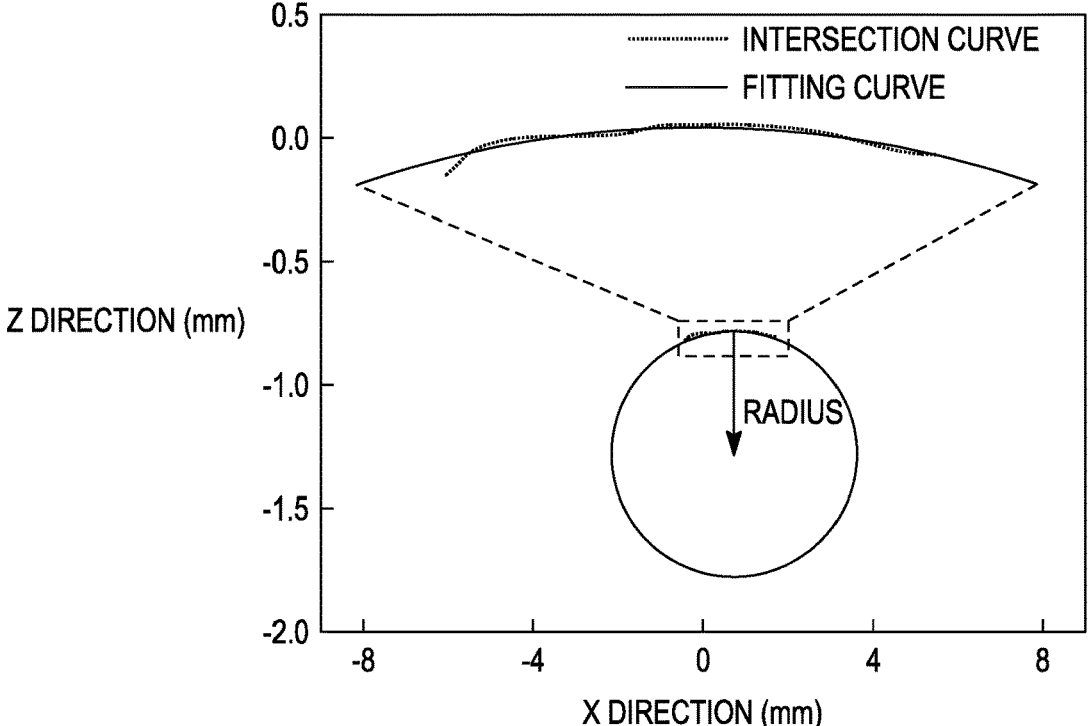

FIG. 21 shows gray scale B-mode images of phantoms and selected windows for calculating the dynamic range. Red: The +15 dB contrast gives an average pixel value of 159.8. Orange: The +6 dB contrast gives an average pixel value of 127.3. Yellow: The +3 dB contrast gives an average pixel value of 110.1. Green: The −15 dB contrast gives an average pixel value of 38.7. Cyan: The −6 dB contrast gives an average pixel value of 68.5. Blue: The −3 dB contrast gives an average pixel value of 80.9. These pixel values are labelled on the pixel scale bar at the bottom. The dynamic range of 63.2 dB is well above the 60 dB threshold usually used in medical diagnosis to give adequate details of the echo patterns in the images.

FIG. 22 presents detailed comparison data of the imaging metrics between the wearable and the commercial imagers. In particular, FIG. 22(A) illustrates the accuracy of the detected scatter positions as a function of the scatter depth. FIG. 22(B) illustrates the elevational resolution as a function of depth. FIG. 22(C) illustrates the lateral resolution as a function of depth. FIG. 22(D) illustrates the axial resolution as a function of depth.

FIG. 23 illustrates processes for evaluating the surface curvature for phase correction. In particular, FIG. 23(A) shows the scanning of the imaging sites on the subject using a 3D scanner. FIG. 23(B) shows obtaining a 3D surface reconstruction from the scanning. FIG. 23(C) shows the selection of the two sites of interest used in this analysis and the build intersection networks in the Catia software. FIG. 23(D) shows zoomed-in schematics of the two intersection networks from one subject. FIG. 23(E) is a graph collecting the average curve radii from curves in the intersection networks. FIG. 23(F) is a graph fitting every intersection curve with a smooth curve. Select the intersection curve whose fitting radius is the closest to the mean radius of all curves from the site. The fitting curve is then used to correct the phased distortion induced by the surface curvature of human body.

Figure 24A:
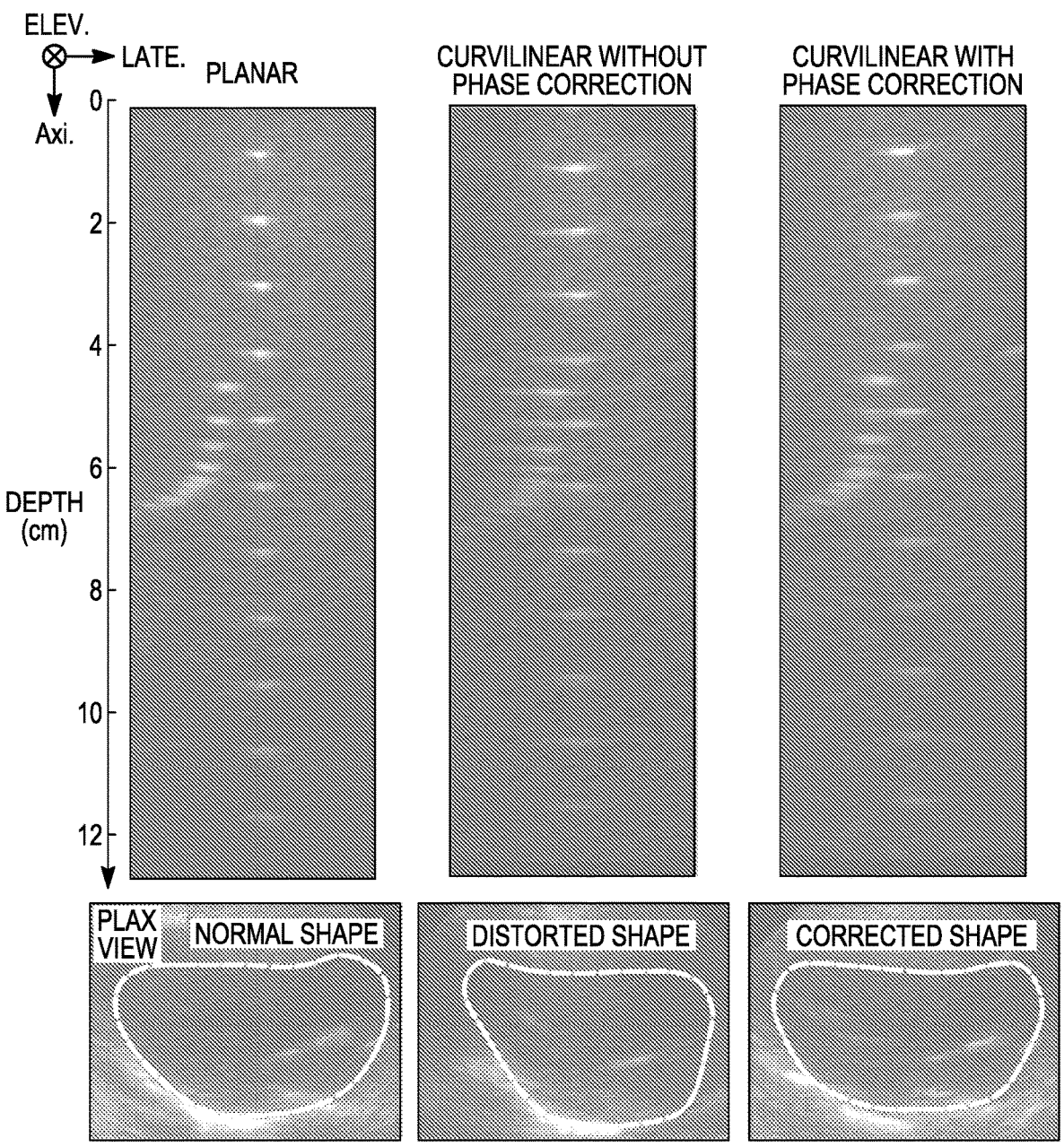
FIGS. 24(A)-24(C) present characterization data showing the effects of phase correction on imaging quality.
Figure 24B:
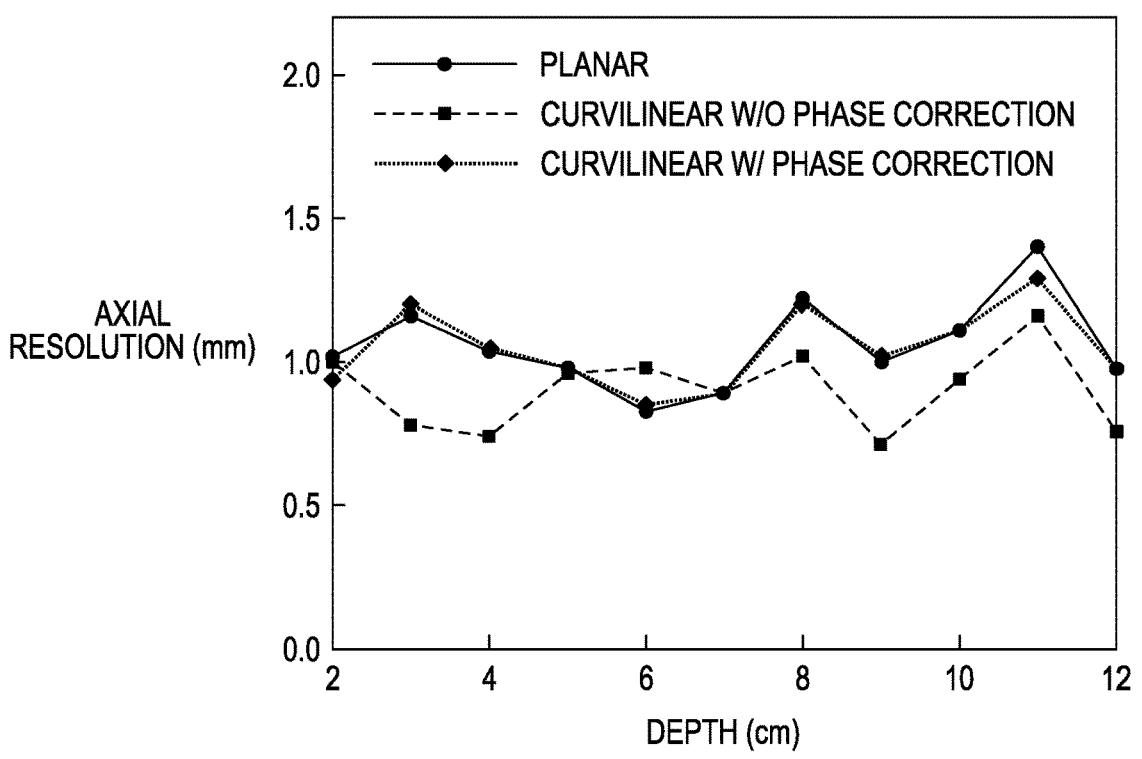
Figure 24C:
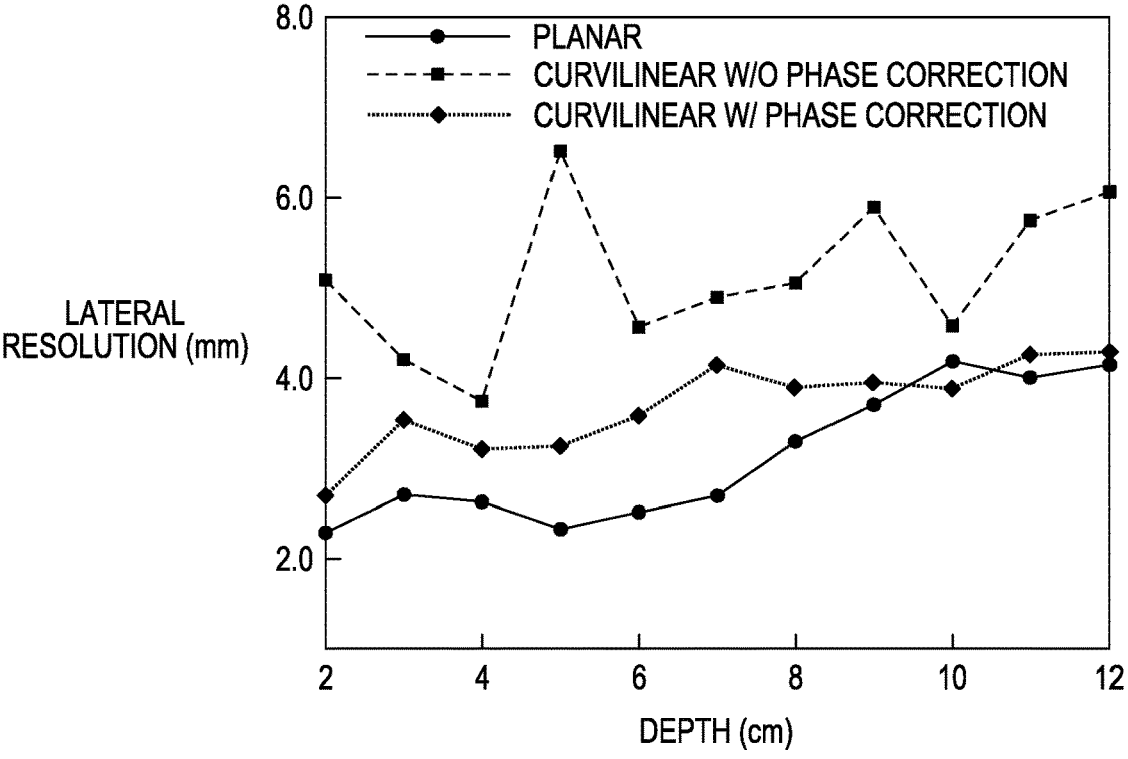
Figure 25A:
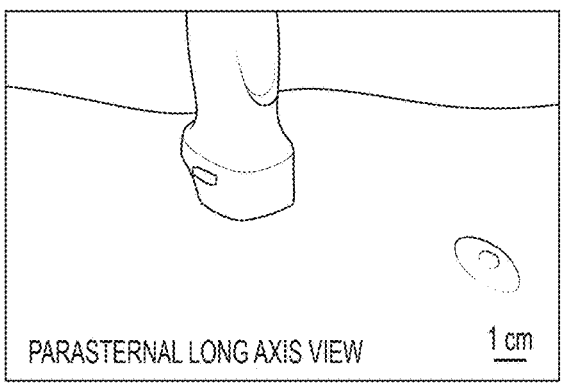
FIGS. 25(A)-25(F) are optical images showing positions and orientations for ultrasound heart imaging.
Figure 25B:
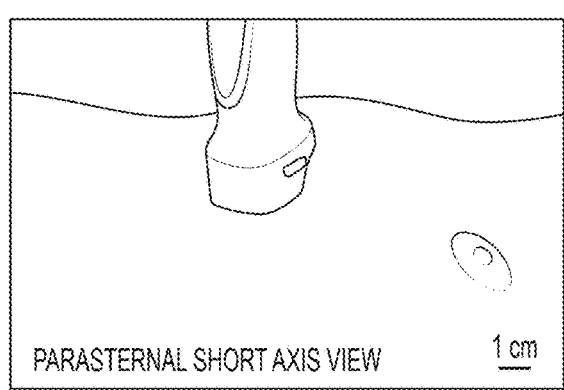
Figure 25C:
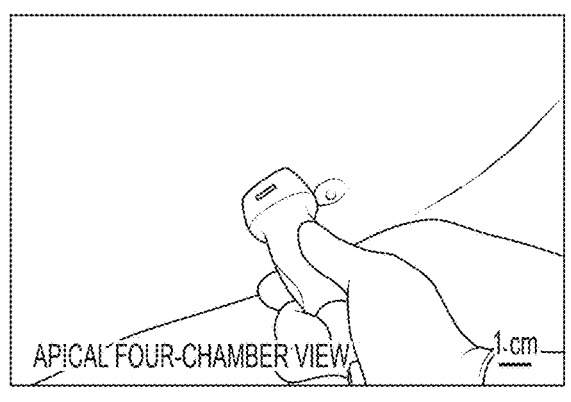
Figure 25D:
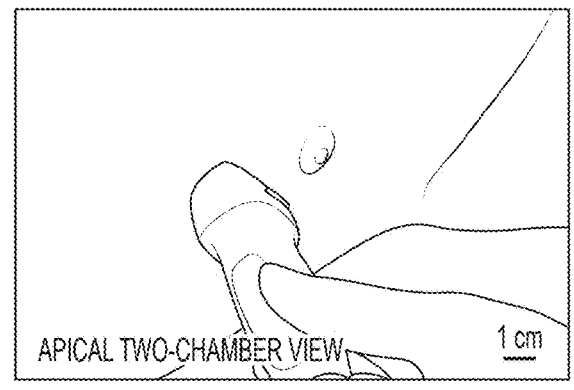
Figure 25E:
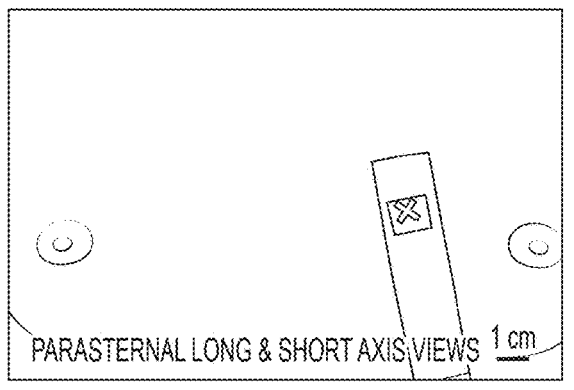
Figure 25F:
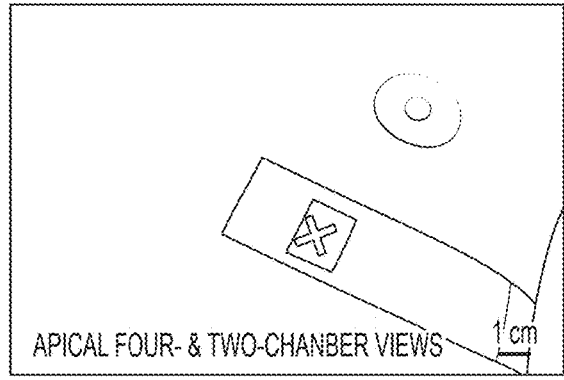

FIG. 24 presents characterization data of the effects of phase correction on imaging quality. In particular, FIG. 25(A) shows B-mode images of a line phantom and parasternal long axis view of the heart obtained from different situations. Left: from a planar surface. Middle: from a curvilinear surface without phase correction. Right: from a curvilinear surface with phase correction. FIG. 24(B) shows the axial and lateral resolutions at different depths under these three situations. No obvious difference in axial resolution was found because it is mainly dependent on the transducer frequency. The lateral resolution of the wearable imager was restored after phase correction.

FIG. 25 are optical images showing positions and orientations for ultrasound heart imaging. In particular, FIG. 25(A) shows a parasternal long axis view, FIG. 25(B) shows a parasternal short axis view, FIG. 25(C) shows a napical four chamber view, and FIG. 25(D) shows an apical two chamber view. The orthogonal wearable cardiac imager combines parasternal long axis and short axis views together (FIG. 25E), and apical four-chamber and apical two-chamber views together (FIG. 25F) without rotation.

Figures 26A, 26B, 26C:
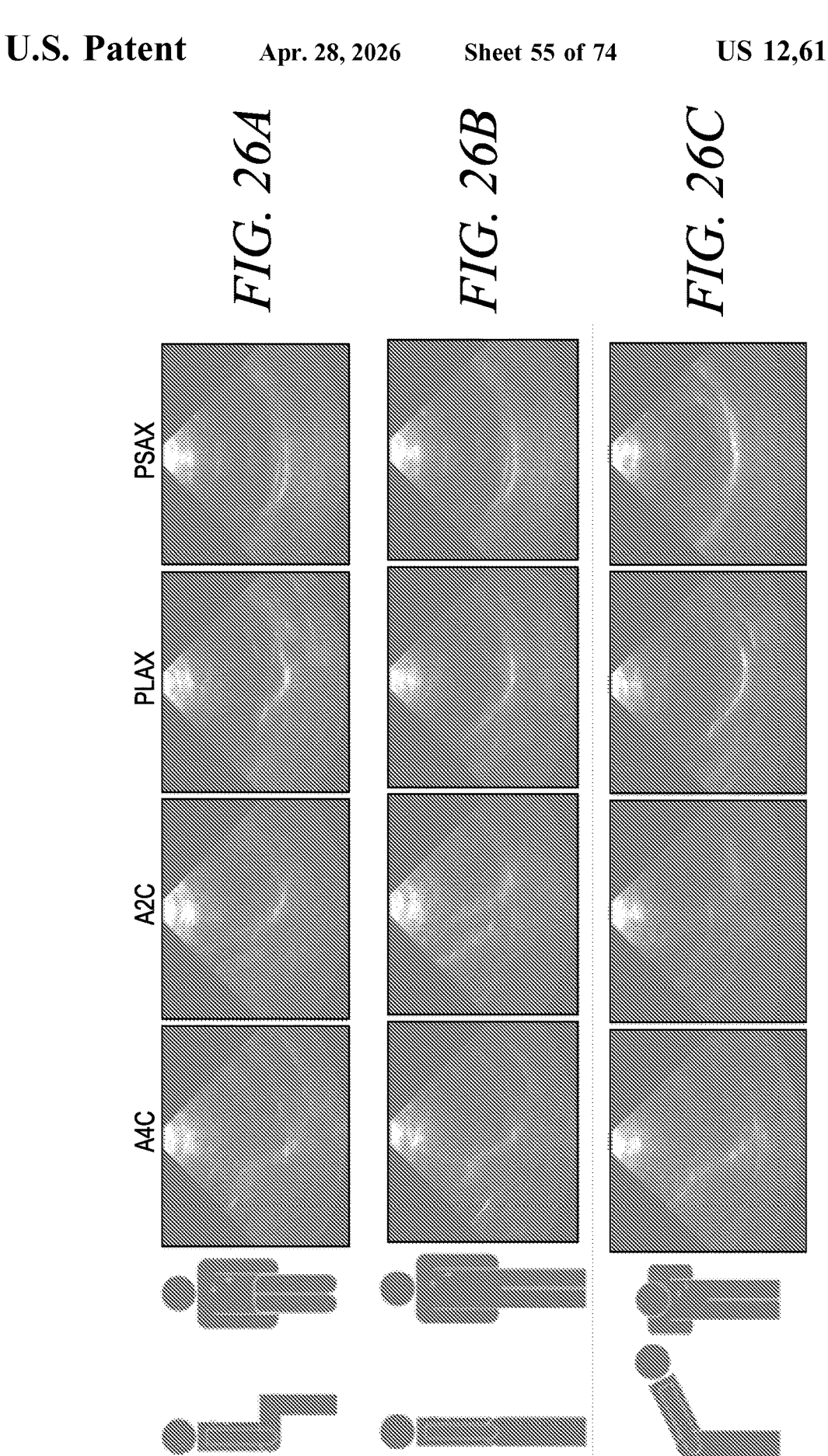

FIG. 26 shows B-mode images collected from a subject with different postures. The four views collected when sitting (FIG. 26A), standing (FIG. 26B), bending over (FIG. 26C), lying flat (FIG. 26D), and lying side (FIG. 26E). The PLAX and PSAX views can keep their quality at different postures while the quality of A4C and A2C views can only be achieved when lying side. A4C: apical four-chamber view; A2C: apical two-chamber view; PLAX: parasternal long axis view; PSAX: parasternal short axis view.

FIG. 27 shows B-mode images collected with different couplants. FIG. 27(A)-FIG. 27(D) respectively show the PSAX, PLAX, A2C and A4C views collected with ultrasound gel. FIG. 27(E)-FIG. 27(H) respectively show the PSAX, PLAX, A2C and A4C views collected with silicone. No obvious structural differences are found in the comparison. PSAX: parasternal short axis view; PLAX: parasternal long axis view; A2C: apical two-chamber view; A4C: apical four-chamber view.

Figure 28:
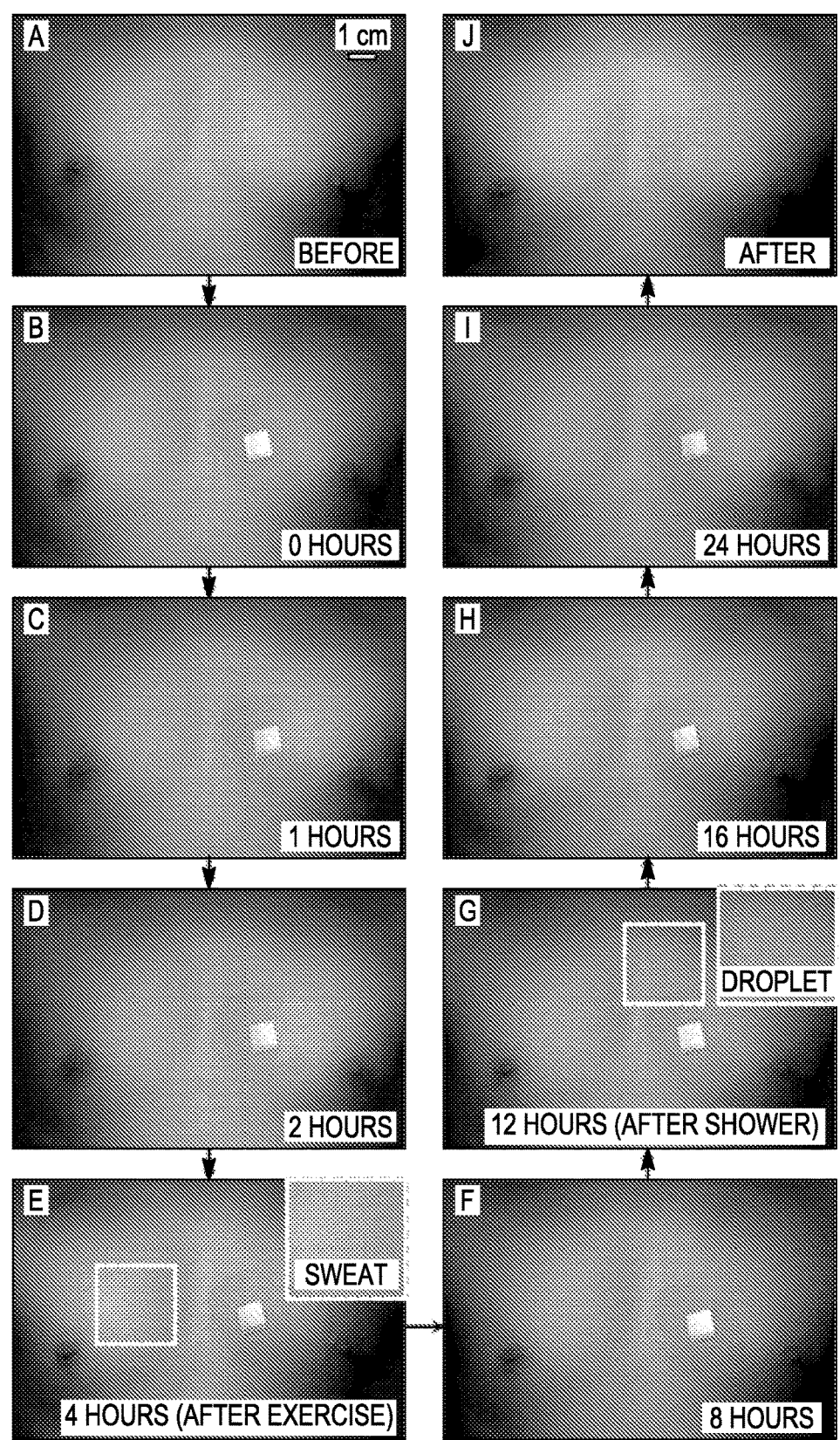
FIGS. 28(A)-28(J) show optical images of attaching the wearable imager to the chest for long-term.

FIG. 28 shows optical images of attaching the wearable imager to the chest for long-term. Optical images of the chest before attaching the probe (FIG. 28A), 0, 1, 2, 4, 8, 12, 16, and 24 hours after the attachment (FIG. 28B-FIG. 28I), and after detaching the imager from human body (FIG. 28J). Sweat droplets can be seen in the zoomed-in inset in FIG. 28(E) after the subject finished working out. Water droplets can be seen in the zoomed-in inset in FIG. 28(G) after the subject finished showering.

Figure 29A:
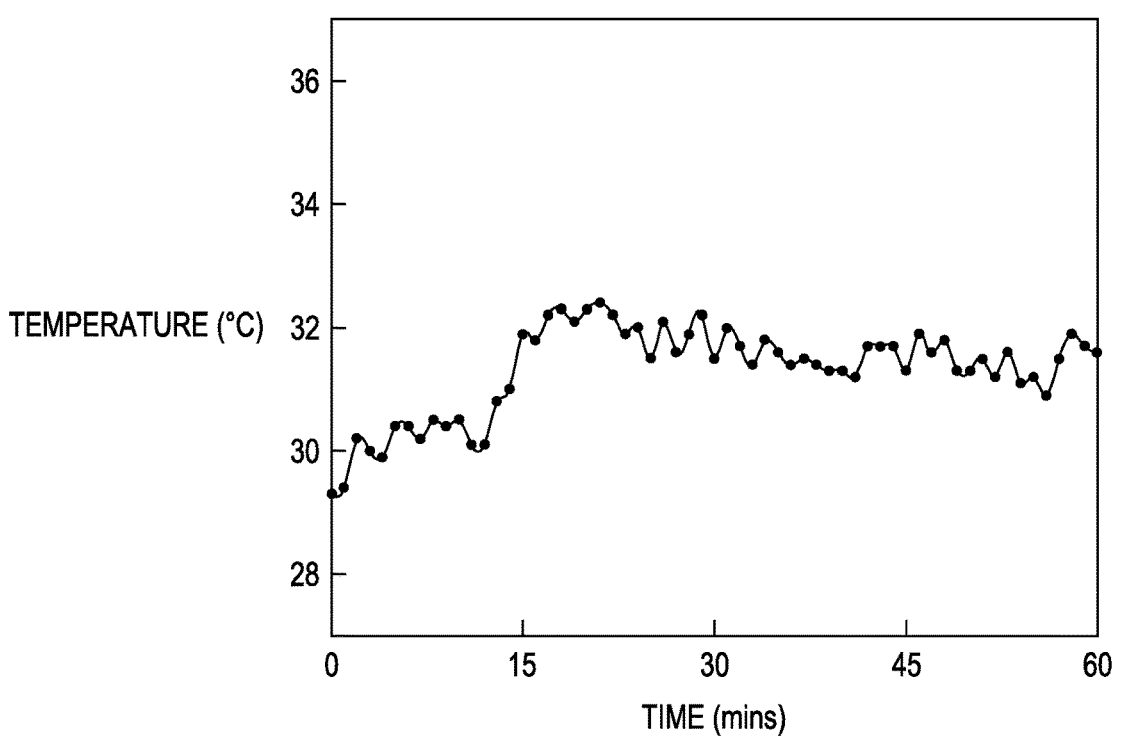
FIGS. 29(A)-29(B) show continuous surface temperature and heart rate monitoring data for 1 hour.
Figure 29B:
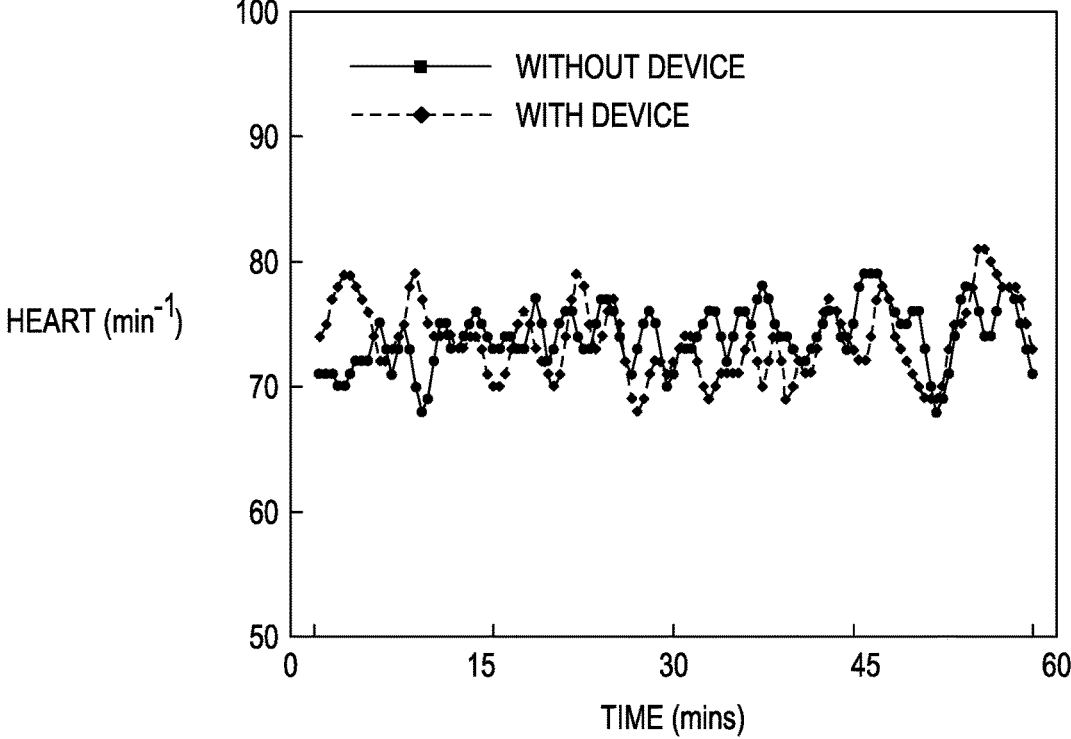

FIG. 29 shows continuous surface temperature and heart rate monitoring results for 1 hour. FIG. 29(A) shows the results of recording the surface temperature of the device by a thermal camera every minute for 1 hour. The highest temperature is ~33° C., which is harmless to the human body. FIG. 29(B) shows the results of monitoring the heart rate using a thermal camera every minute with and without the device attachment. No obvious difference is observed, showing the safety of the wearable cardiac imager for long-term monitoring.

Figure 30:
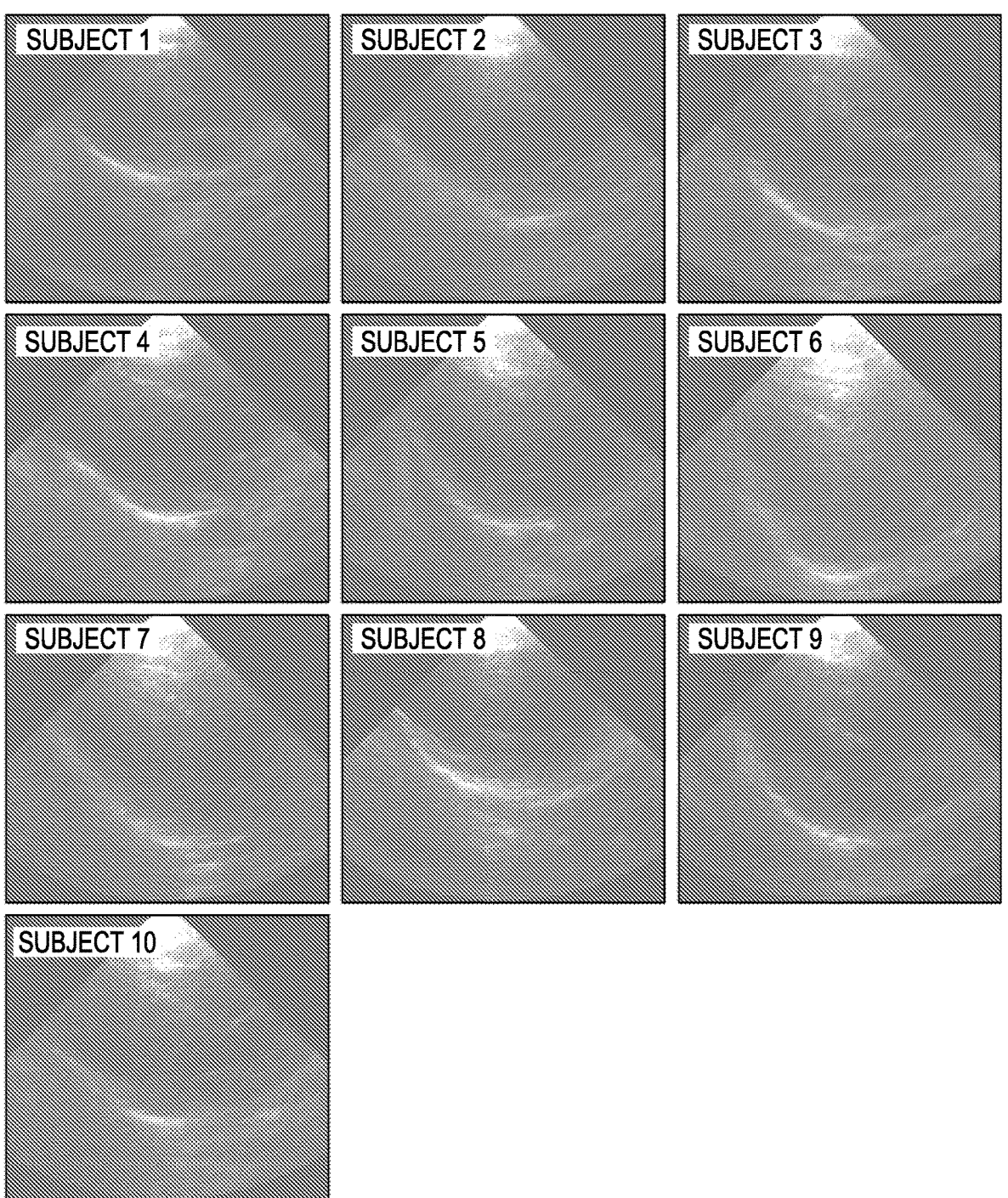
FIG. 30 shows images of the parasternal long axis view from 10 subjects.

FIG. 30 shows images of the parasternal long axis view from 10 subjects. Expanding the testing cohort size validates the reproducibility and reliability of the wearable imager.

FIG. 31 shows the structure of the FCN-32 neural network. The FCN-32's structure includes a series of fully-connected convolutional neural network (CNN) layers and an upsampling layer at the end. We used the AlexNet structure for the downsampling process. The input layer is first connected to 5 groups of connected CNN layers, then connected to 2 additional CNN-dropout bilayers, and finally connected to an upsampling layer to restore to its original size. Specifically, the 5 CNN groups have similar structures but different dimensions. Input of each group is first zero-padded and sent into a 2D convolutional layer. Then, we used batch normalization to standardize the CNN's output and activate it with a Rectified Linear Unit and downsample it with max-pooling.

Figure 32:
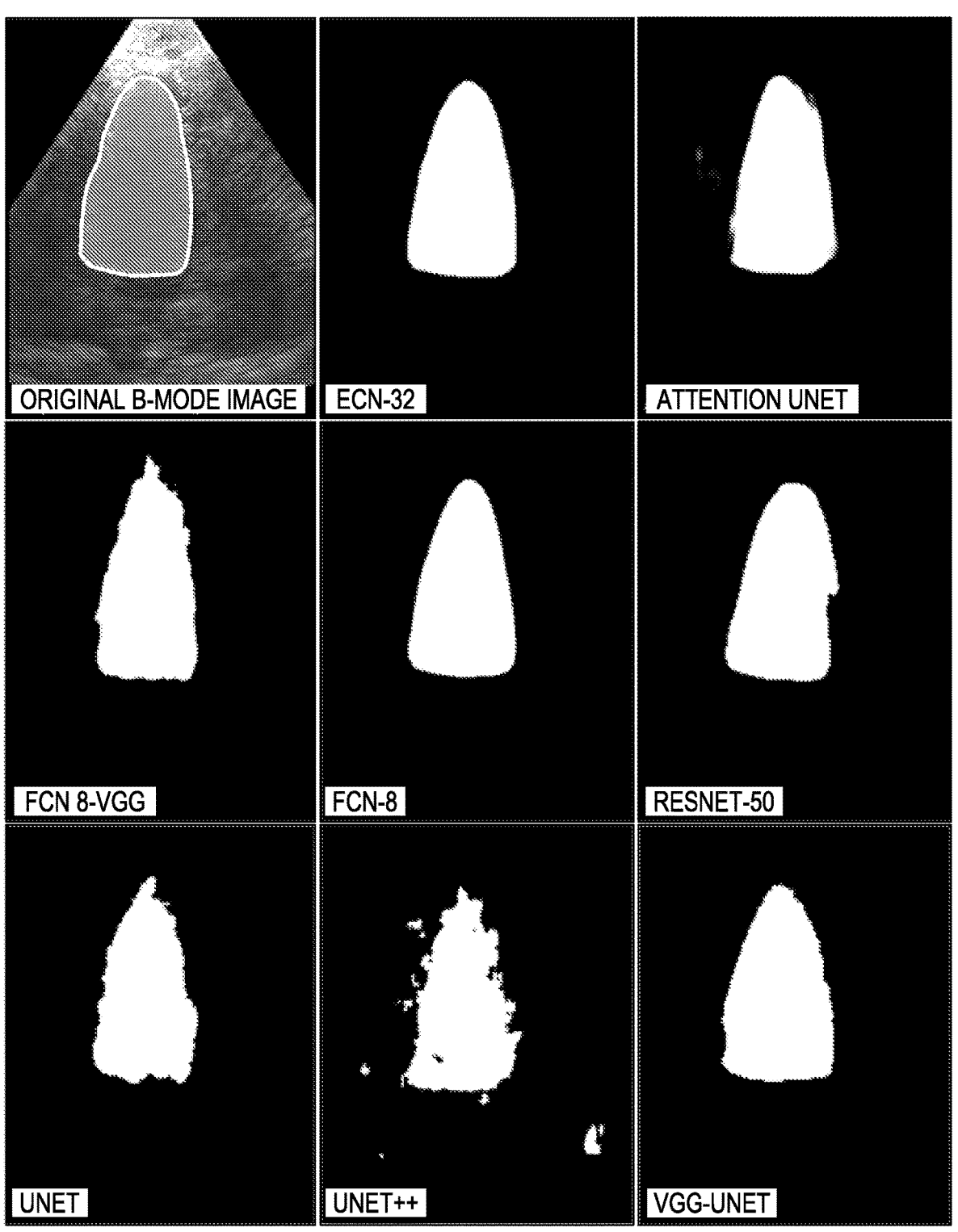
FIG. 32 shows the segmentation results of the left ventricle with different deep learning models.
Figure 33A:
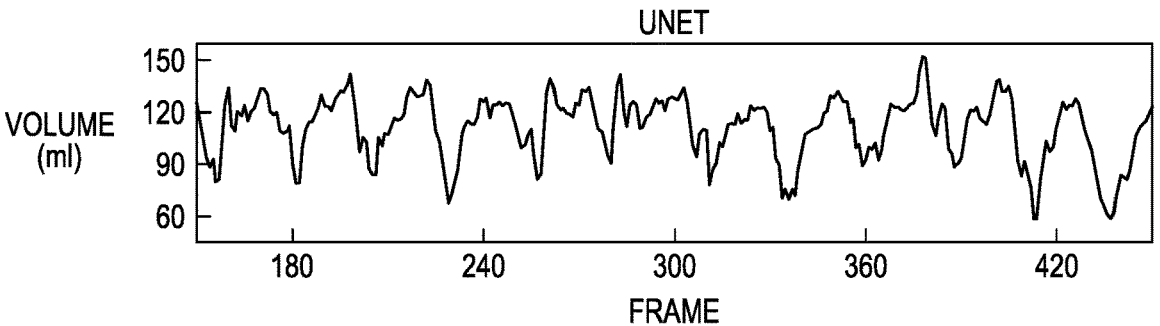
FIG. 33 shows waveforms of the left ventricular volume obtained with different deep learning models.
Figure 33B:
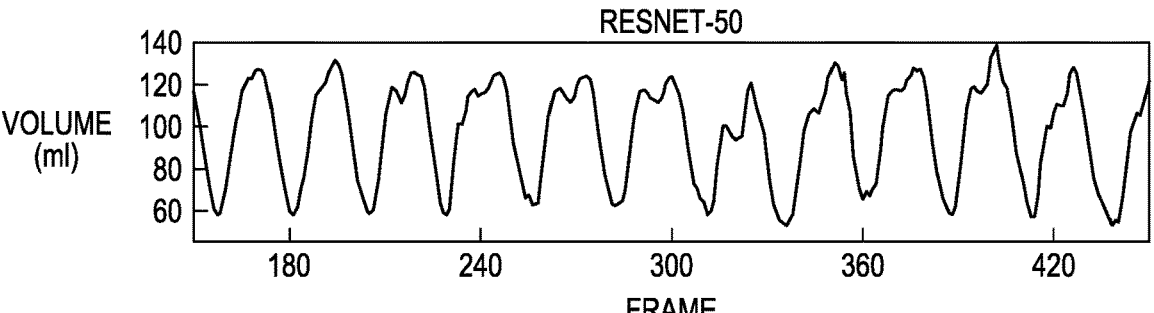
Figure 33C:
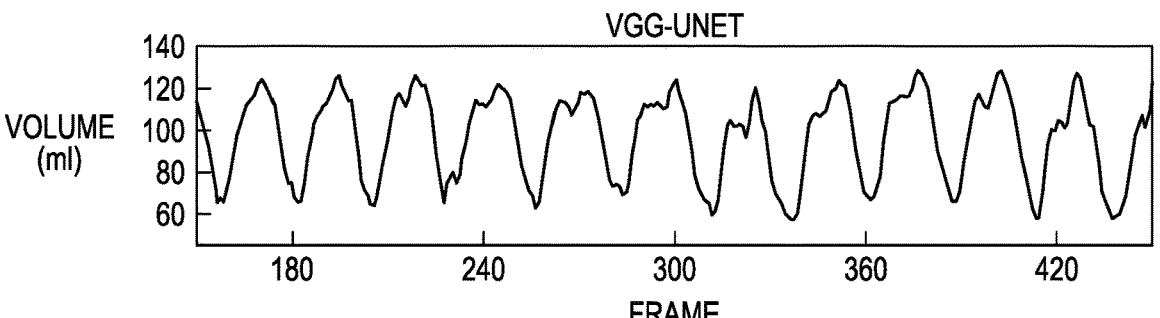
Figure 33D:
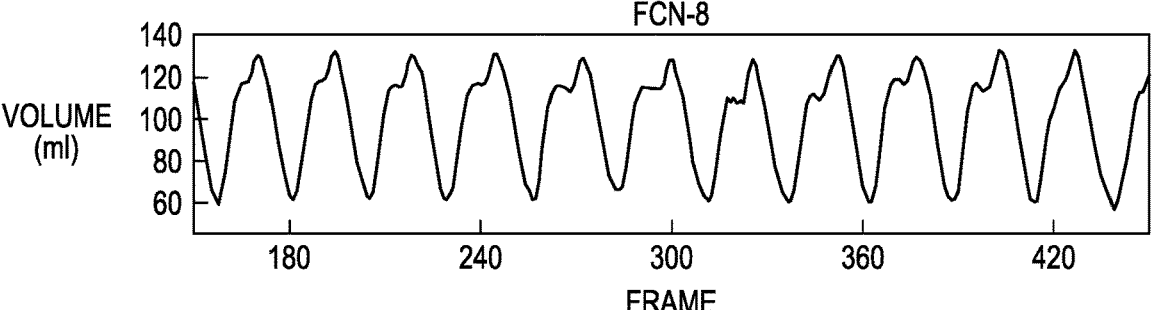
Figure 33E:
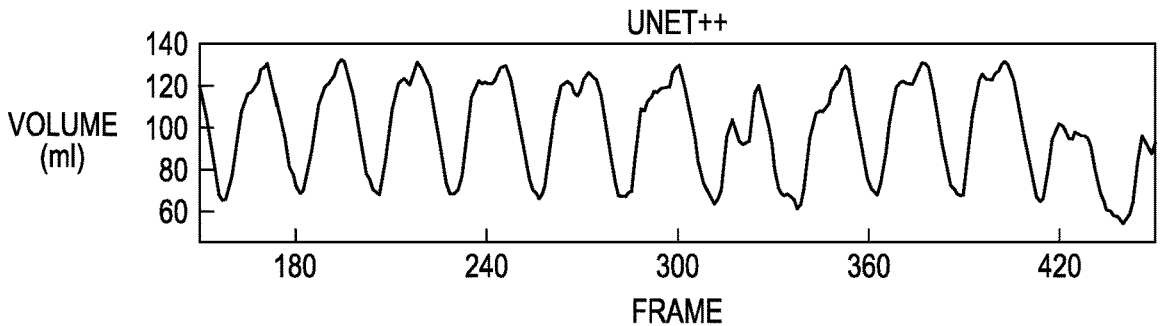
Figure 33F:
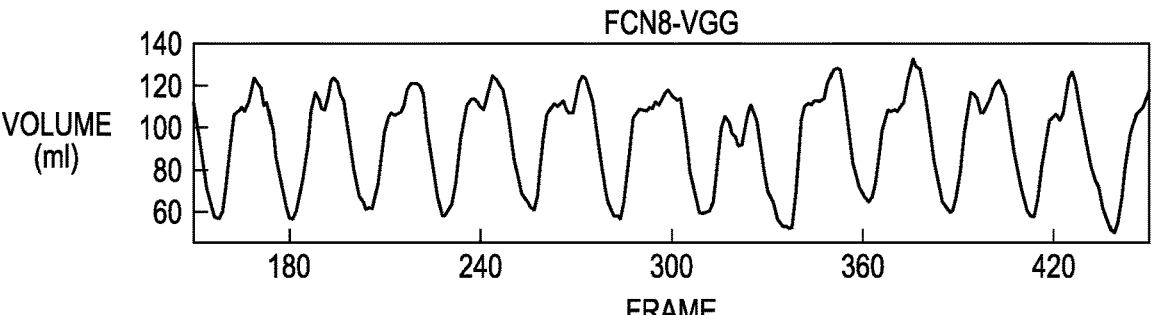
Figure 33G:
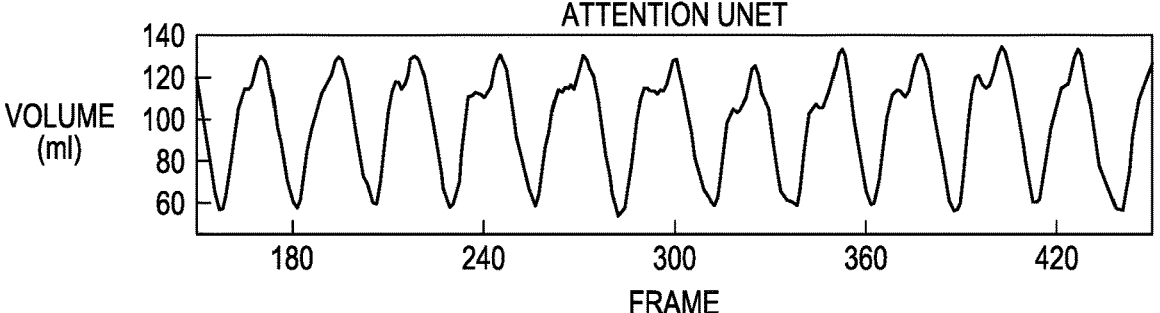
Figure 33H:
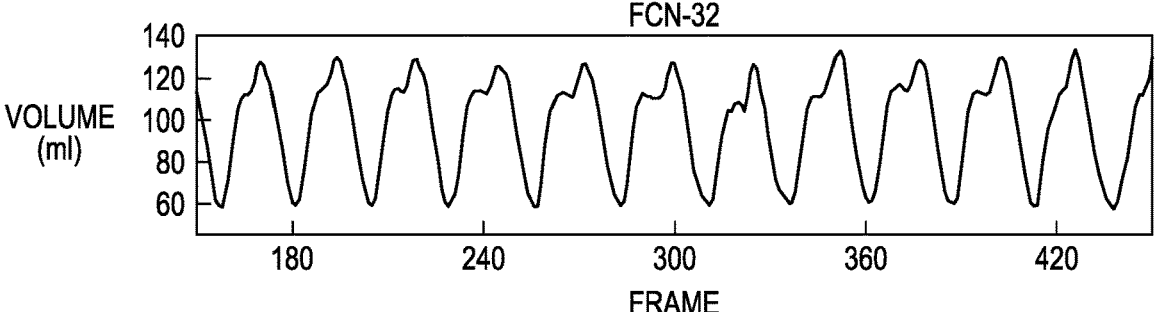

FIG. 32 shows the segmentation results of the left ventricle with different deep learning models. By qualitatively evaluating the result, we found FCN-32 had much smoother edges with the highest fidelity. Compared with the original B-mode image, FCN-32 has the best agreement among all models used in this study.

FIG. 33 shows waveforms of the left ventricular volume obtained with different deep learning models. Those waveforms are from segmenting the same B-mode video. Qualitatively, the waveform generated by the FCN-32 gains better stability and less noise, and the waveform morphology is more constant from cycle to cycle. Quantitatively, the comparison results of those models with mean intersection over union is in FIG. 31, which shows that the FCN-32 has the highest value, showing the best performance in this study.

Figure 34A:
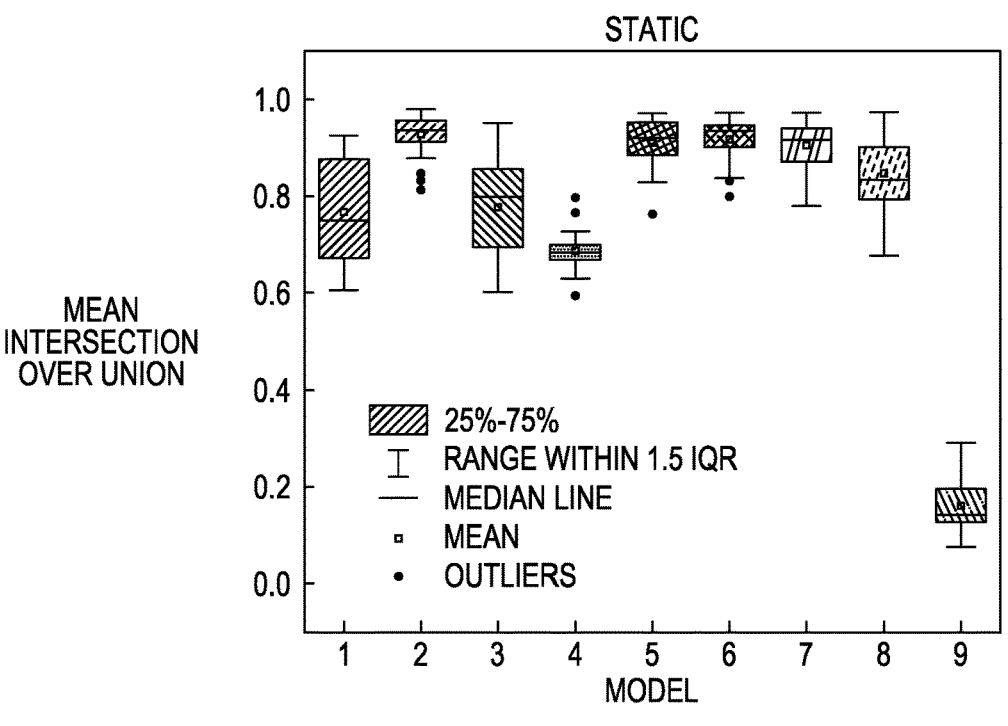
FIGS. 34(A)-34(B) show a comparison of the mean intersection over union among different models used in this study.
Figure 34B:
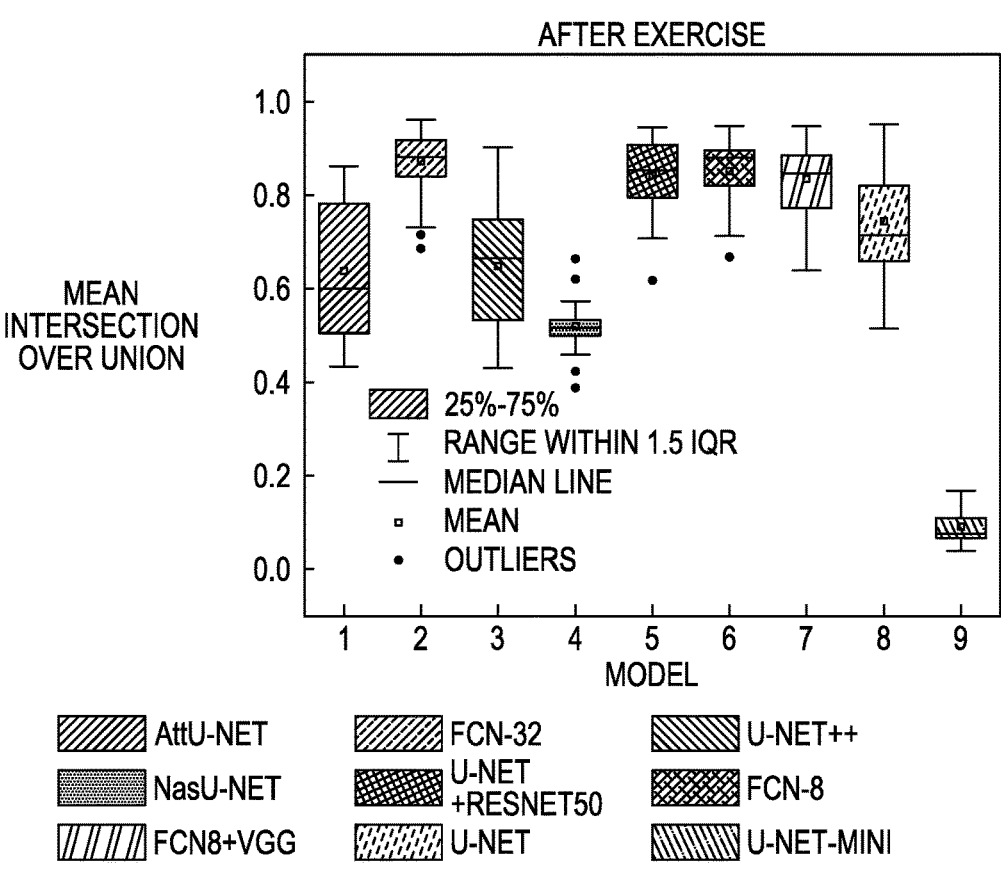

FIG. 34 shows a comparison of the mean intersection over union among different models used in this study. The comparison is made before (FIG. 34A) and after exercise (FIG. 34B). For a pair of predicted images and manually-labelled ground truth image, its intersection over union equals to the number of pixels that are classified as within the left ventricle in both images divided by the total number of unique pixels that are classified as within the left ventricle by either of the two images. The mean intersection over union takes results of all images into account. The FCN-32 performs the best with the highest mean intersection over union and among the lowest variation. 1.5 IQR is a common rule in statistics to differentiate the outliers. Data points outside of this range are regarded as outliers. IQR: interquartile range.

FIG. 36 shows different phases in a cardiac cycle obtained from B-mode imaging. The rows are B-mode images of A4C, A2C, PLAX, and PSAX views in the same phase. The columns are B-mode images of the same view during ventricular filling, atrial contraction, isovolumetric contraction, end of ejection, and isovolumetric relaxation. The dashed lines highlight the major features of the current phase. Bluish lines mean shrinking in volume of the labelled chamber. Reddish lines mean expansion in volume of the labelled chamber. Yellowish lines mean retention in volume of the labelled chamber. A4C: apical four-chamber view; A2C: apical two-chamber view; PLAX: parasternal long axis view; PSAX: parasternal short axis view; LV: left ventricle; RV: right ventricle; LA: left atrium; RA: right atrium; LVOT: left ventricular outflow tract.

Figure 38A:
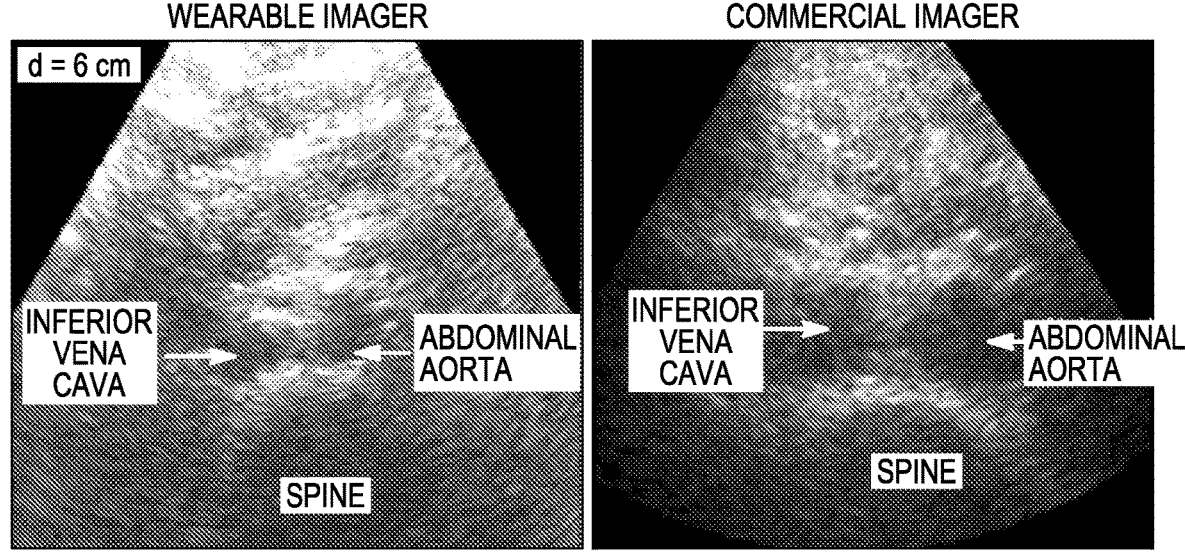
FIGS. 38(A)-38(B) show B-mode images of the abdominal area and liver from the wearable and the commercial imagers.
Figure 38B:
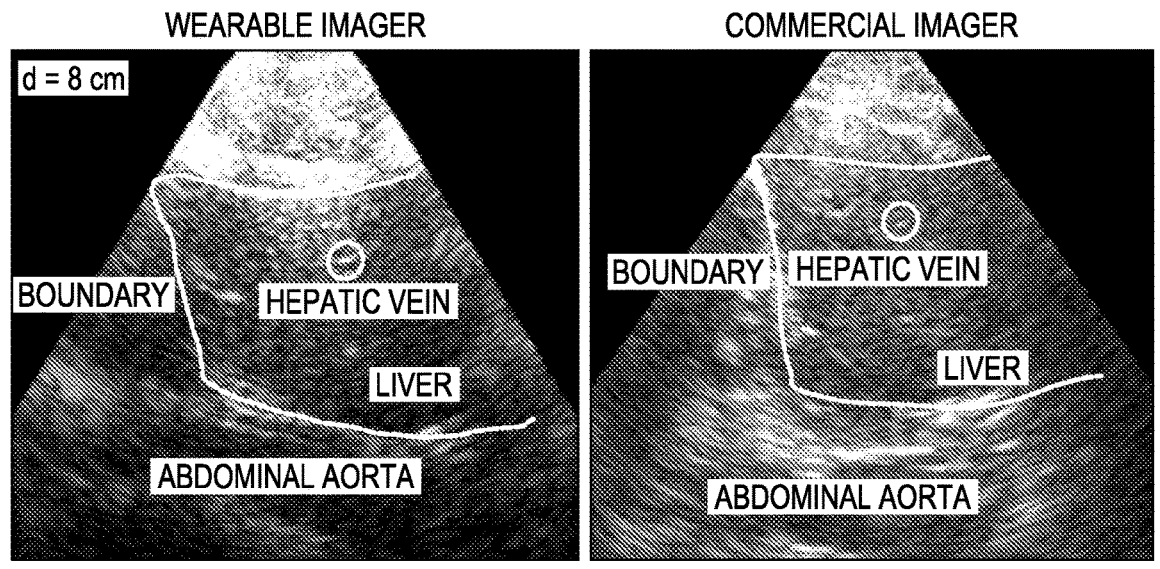

FIG. 38 shows B-mode images of the abdominal area and liver from the wearable and the commercial imagers. In particular, FIG. 38(A) shows B-mode images of the abdominal area. Similar structures including the inferior vena cava and abdominal aorta can be recognized in both images. FIG. 38(B) shows B-mode images of the liver. The complete boundary and fine structures such as the hepatic vein can be observed in both images.

FIG. 39 shows B-mode images of biopsy tests on a commercial phantom (CIRS 052). FIG. 39(A) shows an image of the cross section and longitudinal section of the area of interest before inserting the biopsy needle. FIG. 39(B) shows an image of the cross section and longitudinal section of the area of interest after inserting the biopsy needle. FIG. 39(C) shows an image of the cross section and longitudinal section of the area of interest after releasing the inner stylet. FIG. 39(D) shows an image of the cross section and longitudinal section of the area of interest after removing the biopsy needle. The positions and the behaviors of the biopsy needle are clearly recorded in two orthogonal orientations simultaneously by the wearable imager.

Figure 40A:
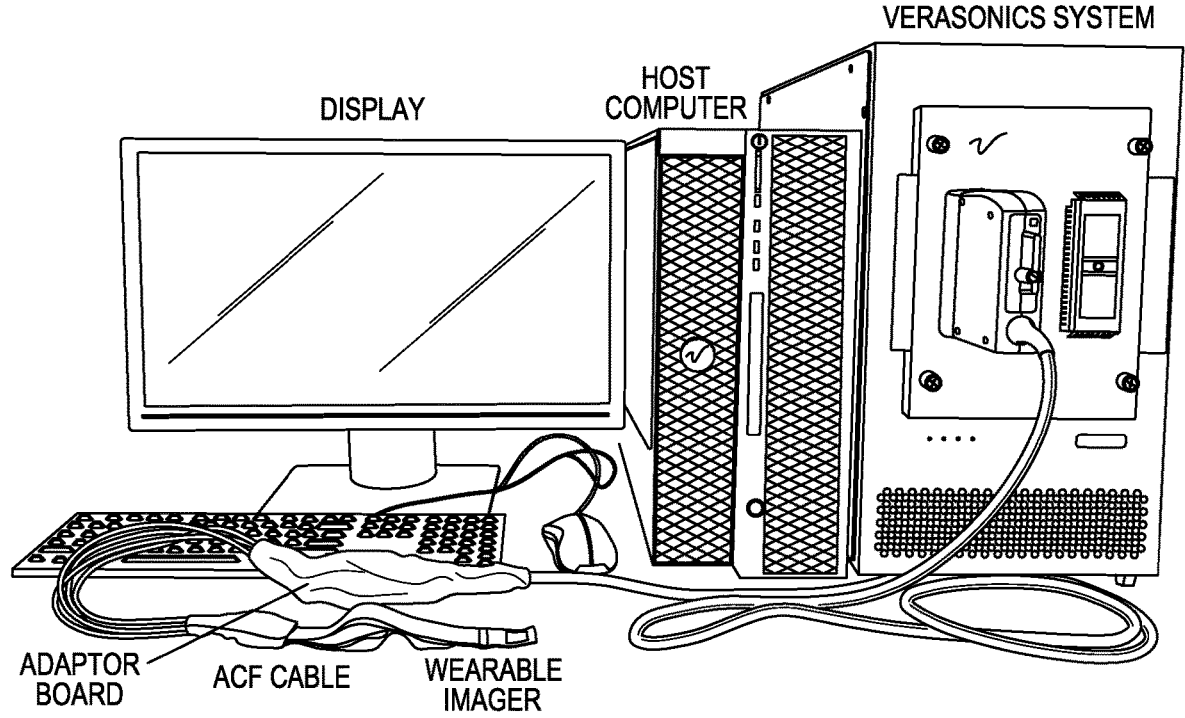
FIGS. 40(A)-40(B) show a photograph and schematic diagrams of the operating platform.
Figure 40B:
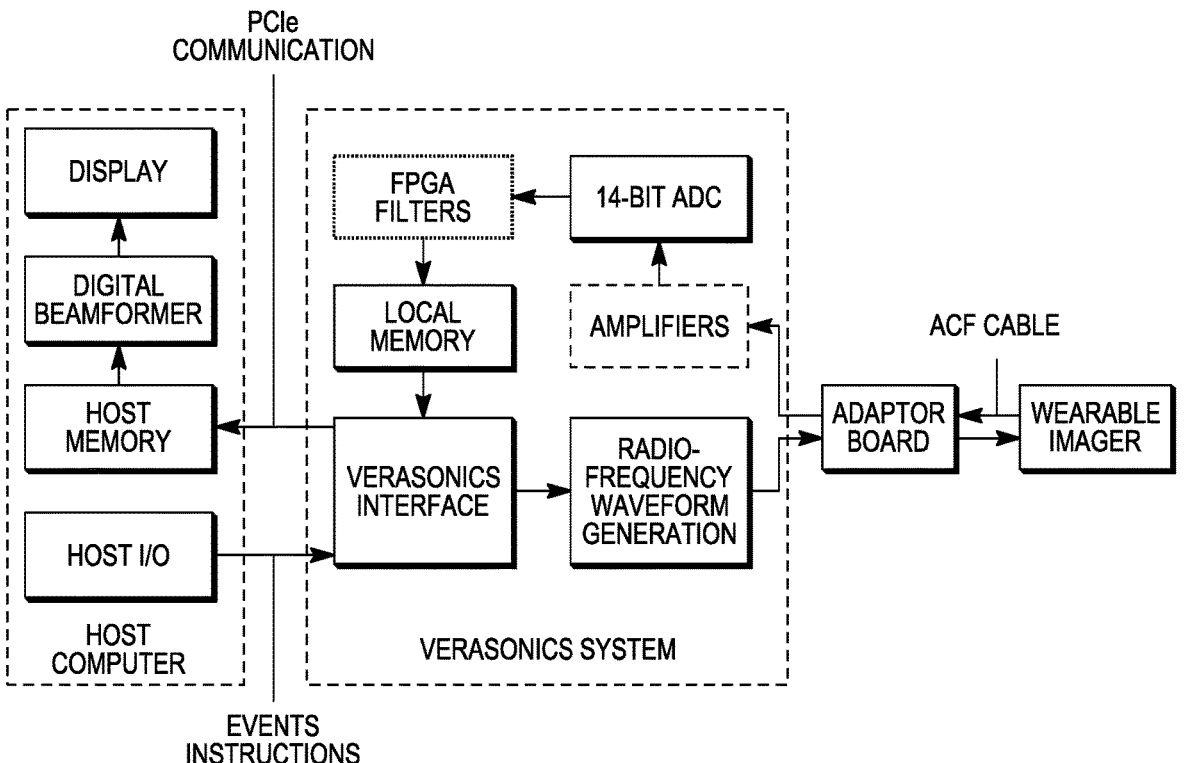
Figure 40B:
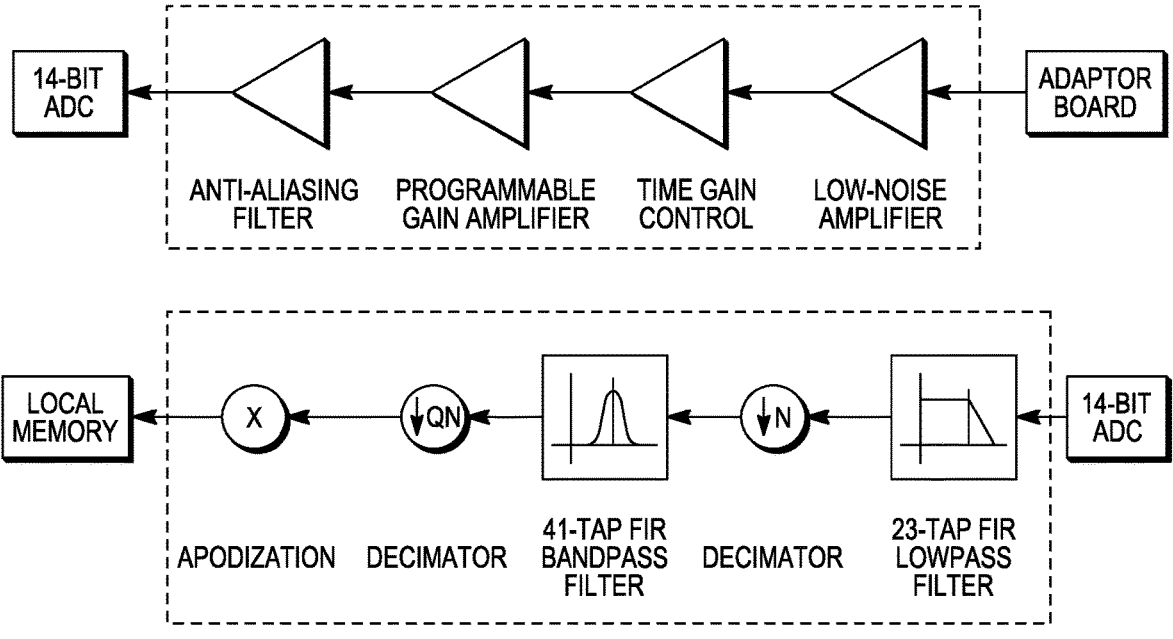

FIG. 40 shows a photograph and schematic diagrams of the operating platform. FIG. 40(A) shows the physical setup of the imaging platform. FIG. 40(B) shows a working schematic flow diagram of the platform, representing the wearable imager and its controller. The middle dashed box shows the analog signal conditioning path of the controller. The low-noise amplifier pre-amplifies the raw signal with high fidelity to facilitate the following conditioning. The time gain control is a programmable amplifier that can selectively amplify electrical signals induced by echoes from different depths. The intensity loss from deep regions is compensated in the time gain control. The programmable gain amplifier allows the overall pixel level to be instantly adjustable when imaging. The anti-aliasing filter is a low-pass filter that cuts off the high-frequency component beyond the Nyquist frequency to make unambiguous analog-to-digital sampling. The corner frequency of the anti-aliasing filter is determined before each run according to the sampling rate. The lower dashed box shows the digital signal conditioning path of the controller. The 23-tap FIR filter is programed based on the central frequency of imaging and filters out signals with frequencies over 4 times of the central frequency. The decimator decimates the signals by N times, where N depends on the central frequency and sampling rate to lower the required bandwidth for data transmission. The 41-tap FIR bandpass filter only allows data near the central frequency to pass, which refines the signals. Another decimator downsamples the data stream according to the setting of the bandpass filter and sampling rate to maximize the transmission efficiency. Finally, apodization is applied to the data in each channel to fulfill the requirement for gradual aperture tapering. Notation used in FIG. 40 includes: ACF: anisotropic conductive film; ADC: analog digital converter; FPGA: field-programmable gate array; PCIe: peripheral component interconnect express; FIR: finite impulse response; I/O: input/output.

Figures 35A, 35B:
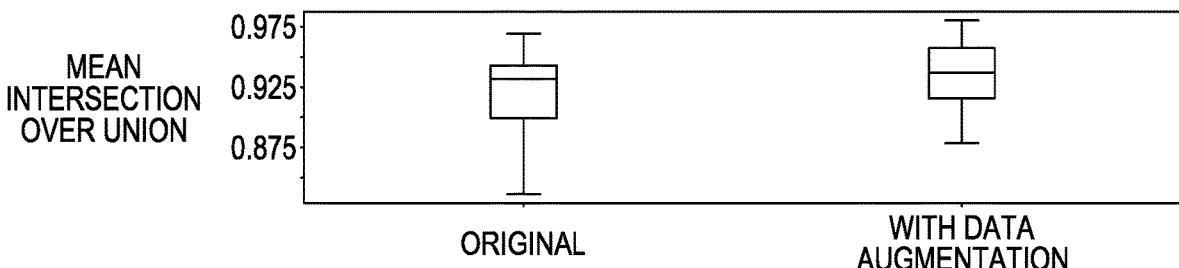
FIGS. 35(A)-35(B) show the types and results of data augmentation.

FIG. 35 shows the types and results of data augmentation. FIG. 35(A) shows the four types of data augmentation and corresponding segmentation results. We applied rotation, scaling, and gaussian noise to the data to augment the size of the dataset. FIG. 35(B) shows that the data augmentation increases the average and reduces the variation of mean intersection over union.

FIG. 37 presents data demonstrating validation of the imputation algorithm. To validate the reliability of this imputation algorithm, we manually erased three periods from FIG. 37(A) an originally continuous volume wave to get the erased result before imputation shown in FIG. 37(B). After imputation, shown in FIG. 37(C), the completed new wave has a good agreement with the original one with a 0.93 Pearson correlation coefficient. To define the hyperparameter N, we compared different imputation results with N=3 (FIG. 37D), N=4 (FIG. 37E), and N=5 (FIG. 37F). The results show the differences between the generated waves from various N numbers are negligible. We decide to use N=3 in practice for its simplicity and algorithm

TABLE 1

| Modality | Parameter | | | | | |
| | Spatial resolution | Temporal resolution | Radioactivity | Invasiveness | Mapping | Citation |
| --- | --- | --- | --- | --- | --- | --- |
| Magnetic resonance imaging | 1.6 mm | 33.3 ms | No | No | 3D | 10 |
| X-Ray computed tomography | 0.3 mm | 50 ms | Yes | No | 3D | 11 |
| Single photon emission computed tomography | 10 mm | 37.5 ms | Yes | No | 3D | 12 |
| Positron emission tomography | 2 mm | 2000 ms | Yes | No | 3D | 12 |
| Optical voltage map | 1 mm | 0.25 ms | No | No | 2D | 13 |
| Optical coherence tomography | 0.001 mm | 85 ms | No | No | 3D | 14 |
| Ultrasonography | 1 mm | <1 ms | No | No | 3D | 15, 16 |

Table 1 shows a summary of existing imaging methods for the heart. Spatial resolution, temporal resolution, radioactivity, invasiveness, and mapping capability are evaluation parameters in this study. Comprehensive analysis of these parameters of cardiac imaging technologies helps us understand standards of medical imaging technologies, which serve as guidance for developing the wearable cardia imager.

TABLE 2

| | Wearable imager | Commercial imager |
| --- | --- | --- |
| Depth of penetration (cm) | >16 | >16 |
| Axial accuracy (%) | 98.7 (40 mm) | 99.3 (40 mm) |
| | 96.6 (70 mm) | 95.6 (70 mm) |
| | 96.0 (110 mm) | 99.0 (110 mm) |
| Lateral accuracy (%) | 95.9 | 97.0 |
| Axial resolution (mm) | 0.57 (40 mm) | 0.54 (40 mm) |
| | 0.55 (70 mm) | 0.65 (70 mm) |
| | 0.62 (110 mm) | 0.71 (110 mm) |
| Lateral resolution (mm) | 0.87 (40 mm) | 1.26 (40 mm) |
| | 1.21 (70 mm) | 1.57 (70 mm) |
| | 1.35 (110 mm) | 2.28 (110 mm) |
| Elevational resolution (mm) | 3.75 (40 mm) | 3.87 (40 mm) |
| | 4.61 (70 mm) | 2.30 (70 mm) |
| | 6.71 (110 mm) | 3.14 (110 mm) |
| Contrast resolution (dB) | <3 | <3 |
| Dynamic range (dB) | 63.2 (−24.0-39.2) | 50.26 (−28.7-21.6) |
| Dead zone (mm) | 6 | <1 |
| Bandwidth (%) | 55 | 74 |
| Contrast-to-noise ratio | 1.51 (−15 dB) | 2.24 (−15 dB) |
| | 0.76 (−6 dB) | 0.90 (−6 dB) |
| | 0.63 (−3 dB) | 0.33 (−3 dB) |
| | 1.12 (+3 dB) | 0.59 (+3 dB) |
| | 1.53 (+6 dB) | 1.10 (+6 dB) |
| | 2.08 (+15 dB) | 1.82 (+15 dB) |
| Insertion loss (dB) | 24.98 | 16.68 |

Table 2 presents a full comparison of the imaging metrics between the wearable imager and a commercial ultrasound imager (Model P4-2v). The performance of wearable imager is comparable to that of the commercial one.

Certain aspects of the imaging device described herein are presented in the foregoing description and illustrated in the accompanying drawing using electronic hardware, computer software, or any combination thereof. Whether such elements are implemented as hardware or software depends upon the particular application and design constraints imposed on the overall system. By way of example, such elements, or any portion of such elements, or any combination of such elements may be implemented with one or more processors or controllers. Examples of processors or controllers include microprocessors, microcontrollers, digital signal processors (DSPs), field programmable gate arrays (FPGAs), programmable logic devices (PLDs), state machines, gated logic, discrete hardware circuits, and any other suitable hardware configured to perform the various functionalities described throughout this disclosure. Examples of processors or controllers may also include general-purpose computers or computing platforms selectively activated or reconfigured by code to provide the necessary functionality.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

The invention claimed is:

1. A stretchable and flexible imaging device that conforms to a shape of patient tissue to which it is attached, comprising:

a stretchable and flexible encapsulation substrate and superstrate, the stretchable and flexible encapsulation substrate being configured to be removably attachable to tissue of a patient;

an ultrasound transducer array having a plurality of transducer elements disposed between the substrate and superstrate for transmitting and receiving ultrasound waves, the transducer elements being arranged so that data from the received ultrasound waves is processable into an ultrasound image of specified tissue of a patient;

a stretchable and flexible electrical interconnect layered structure disposed between the superstrate or substrate and the ultrasound transducer array and being operatively coupled to the transducer elements such that the stretchable and flexible electrical interconnect layered structure is configured to address the transducer elements;

an electromagnetic shielding layer located between the superstrate and the stretchable electrical interconnect layered structure, the electromagnetic shielding layer being stretchable and including a liquid metal; and a controller configured to implement a beamforming algorithm, the controller being in operative communication with the stretchable and flexible electrical interconnect layered structure for generating the ultrasound images of the specified tissue of the patient.

2. The stretchable and flexible imaging device of claim 1, wherein the beamforming algorithm includes at least one algorithm selected from a group including a plane-wave algorithm, a mono-focus algorithm, a plane-wave compounding algorithm and a wide-beam compounding algorithm.

3. The stretchable and flexible imaging device of claim 1, wherein the transducer elements in the ultrasound transducer array are arranged into a plurality of linear arrays that overlap and cross one another.

4. The stretchable and flexible imaging device of claim 3, wherein the plurality of linear arrays includes two linear arrays for generating simultaneous bi-plane ultrasound images.

5. The stretchable and flexible imaging device of claim 3, wherein the plurality of linear arrays includes three or more linear arrays for generating three or more simultaneous ultrasound images representing different image planes.

6. The stretchable and flexible imaging device of claim 4, wherein the two linear arrays are orthogonal to one another.

7. The stretchable and flexible imaging device of claim 3, wherein each of the plurality of linear arrays has a length and width each defined by at least two transducer elements.

8. The stretchable and flexible imaging device of claim 3, wherein the transducer elements in the plurality of linear arrays have a pitch between 0.01 mm and 2 cm.

9. The stretchable and flexible imaging device of claim 8, wherein the plurality of linear arrays each have a length between 0.5 mm and 50 cm.

10. The stretchable and flexible imaging device of claim 1, wherein the transducer array has an aperture-to-pitch ratio of 30-60.

11. The stretchable and flexible imaging device of claim 1, wherein the ultrasound transducer array is a two-dimensional array configured to generate three-dimensional volumetric ultrasound images.

12. The stretchable and flexible imaging device of claim 1, wherein the transducer elements in the ultrasound transducer array are arranged periodically or nonperiodically.

13. The stretchable and flexible imaging device of claim 1, wherein the stretchable and flexible electrical interconnect layered structure comprises liquid-metal electrodes that include a multilayered liquid metal in a polymer matrix.

14. The stretchable and flexible imaging device of claim 1, wherein the stretchable and flexible electrical interconnect layered structure comprises carbon nanotubes.

15. The stretchable and flexible imaging device of claim 1, wherein the transducer elements are piezoelectric transducer elements.

16. The stretchable and flexible imaging device of claim 15, wherein the piezoelectric transducer elements comprise a 1-3 composite material.

17. The stretchable and flexible imaging device of claim 15, wherein the piezoelectric transducer elements comprise a PMN-PT single crystal.

18. The stretchable and flexible imaging device of claim 1, wherein the transducer elements are piezoelectric micromachined ultrasonic (PMUT) or capacitive micromachined ultrasonic (CMUT) transducer elements.

19. The stretchable and flexible imaging device of claim 1, wherein the stretchable and flexible encapsulation substrate and superstrate comprises a triblock copolymer.

20. The stretchable and flexible imaging device of claim 1, wherein the specified tissue of the patient is an internal organ of the patient, the internal organ being imaged while the patient undergoes body movement.

21. The stretchable and flexible imaging device of claim 1, wherein the patient tissue to which the stretchable and flexible encapsulation substrate is configured to be removably attachable is an epidermis of the patient.

22. The stretchable and flexible imaging device of claim 1, wherein the controller is electrically and operatively coupled to the stretchable and flexible electrical interconnect layered structure through an electrical impedance matching circuit.

23. A method of generating an ultrasound image of patient tissue of a patient, comprising:

attaching in a removable manner a stretchable and flexible ultrasound imaging device to the patient tissue of the patient, the stretchable and flexible ultrasound imaging device including a stretchable and flexible encapsulation substrate and superstrate;

an ultrasound transducer array having a plurality of transducer elements disposed between the substrate and superstrate; and a stretchable electrical interconnect layered structure disposed between the superstrate and the ultrasound transducer array and being in operative communication with the transducer elements such that the stretchable electrical interconnect layered structure is configured to address each of the transducer elements;

an electromagnetic shielding layer located between the superstrate and the stretchable electrical interconnect layered structure, the electromagnetic shielding layer being stretchable and including a liquid metal;

transmitting ultrasound waves into the patient using the transducer elements;

receiving ultrasound waves from the patient using the transducer elements; and generating and displaying an ultrasound image of the specified tissue of the patient using the received ultrasound waves.

24. The method of claim 23, wherein the specified tissue is an internal organ of the patient, the internal organ being imaged while the patient undergoes body movement.

25. The method of claim 24, wherein the internal organ is the heart and the ultrasound image is an echocardiogram.

26. The method of claim 23, wherein the specified tissue is at least one tissue selected from a group consisting of an inferior vena cava, abdominal aorta, spine, and liver.

27. The method of claim 23, wherein the transmitting employs a beamforming scheme selected from a group including a plane-wave algorithm, a mono-focus algorithm, a plane-wave compounding algorithm and a wide-beam compounding algorithm.

28. The method of claim 27, wherein the receiving employs at least one beamforming scheme selected from group including a delay and sum algorithm, a delay multiply and sum algorithm, and a filtered-delay multiply and sum algorithm.

29. The method of claim 25, wherein the echocardiogram of the heart is based on four standard views that include an apical four-chamber view, an apical two-chamber view, a parasternal long axis view and a parasternal short axis view.

30. The method of claim 27, wherein the beamforming scheme employs a phase correction algorithm to compensate for deformation of the transducer array when attached to the patient tissue.

31. The stretchable and flexible imaging device of claim 1, wherein the ultrasound transducer array is configured to generate B-mode and M-mode images.

* * * * *